US007655405B2

(12) United States Patent
Sorge

(10) Patent No.: US 7,655,405 B2
(45) Date of Patent: *Feb. 2, 2010

(54) COMPOSITIONS AND KITS FOR DETECTION OF A TARGET NUCLEIC ACID

(75) Inventor: Joseph A. Sorge, Wilson, WY (US)

(73) Assignee: Hologic, Inc, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/606,531

(22) Filed: Nov. 29, 2006

(65) Prior Publication Data

US 2007/0231815 A1    Oct. 4, 2007

Related U.S. Application Data

(60) Division of application No. 11/106,237, filed on Apr. 14, 2005, now Pat. No. 7,482,121, which is a division of application No. 09/728,574, filed on Nov. 30, 2000, now Pat. No. 7,118,860, which is a continuation-in-part of application No. 09/650,888, filed on Aug. 30, 2000, now Pat. No. 6,548,250, which is a continuation-in-part of application No. 09/430,692, filed on Oct. 29, 1999, now Pat. No. 6,528,254.

(51) Int. Cl.
C12Q 1/68 (2006.01)
C07H 21/02 (2006.01)
C07H 21/04 (2006.01)

(52) U.S. Cl. .................. 435/6; 536/23.1; 536/24.3

(58) Field of Classification Search ............ 435/6; 536/23.1, 24.3
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | 435/6 |
| 4,683,202 A | 7/1987 | Mullis | 435/91 |
| 4,800,159 A | 1/1989 | Mullis et al. | 435/172.3 |
| 4,889,818 A | 12/1989 | Gelfand et al. | |
| 5,210,015 A | 5/1993 | Gelfand et al. | 435/6 |
| 5,312,728 A | 5/1994 | Lizardi et al. | |
| 5,424,413 A | 6/1995 | Hogan et al. | 536/24.31 |
| 5,466,591 A | 11/1995 | Abramson et al. | |
| 5,487,972 A | 1/1996 | Gelfand et al. | 435/6 |
| 5,538,848 A | 7/1996 | Livak et al. | 435/5 |
| 5,556,772 A | 9/1996 | Sorge et al. | |
| 5,719,028 A | 2/1998 | Dahlberg et al. | 435/6 |
| 5,804,375 A | 9/1998 | Gelfand et al. | |
| 5,837,450 A | 11/1998 | Dahlberg et al. | 435/6 |
| 5,837,464 A | 11/1998 | Capon et al. | |
| 5,843,669 A | 12/1998 | Kaiser et al. | |
| 5,846,717 A | 12/1998 | Brow et al. | 435/6 |
| 5,853,990 A | 12/1998 | Winger et al. | |
| 5,854,033 A | 12/1998 | Lizardi | |
| 5,874,283 A | 2/1999 | Harrington et al. | |
| 5,874,293 A | 2/1999 | Miettinin-Oinonen et al. | |
| 5,888,780 A | 3/1999 | Dahlberg et al. | 435/91.53 |
| 5,925,517 A | 7/1999 | Tyagi et al. | |
| 5,942,391 A | 8/1999 | Zhang et al. | |
| 5,948,649 A | 9/1999 | Stewart et al. | |
| 5,985,557 A | 11/1999 | Prudent et al. | |
| 5,994,069 A | 11/1999 | Hall et al. | |
| 6,150,097 A | 11/2000 | Tyagi et al. | 435/6 |
| 6,350,580 B1 * | 2/2002 | Sorge | 435/6 |
| 6,528,254 B1 * | 3/2003 | Sorge | 435/6 |
| 6,548,250 B1 * | 4/2003 | Sorge | 435/6 |
| 6,589,743 B2 * | 7/2003 | Sorge | 435/6 |
| 6,803,201 B2 * | 10/2004 | Sorge et al. | 435/6 |
| 6,893,819 B1 * | 5/2005 | Sorge | 435/6 |
| 7,118,860 B2 * | 10/2006 | Sorge et al. | 435/6 |
| 7,148,339 B2 * | 12/2006 | Greener et al. | 536/23.2 |
| 7,183,052 B2 * | 2/2007 | Sorge | 435/6 |
| 7,276,597 B2 * | 10/2007 | Sorge | 536/24.3 |
| 7,297,519 B2 * | 11/2007 | Sorge et al. | 435/91.2 |
| 7,309,573 B2 * | 12/2007 | Sorge | 435/6 |
| 7,361,467 B2 * | 4/2008 | Sorge et al. | 435/6 |
| 7,361,469 B2 * | 4/2008 | Sorge et al. | 435/6 |
| 7,381,532 B2 * | 6/2008 | Sorge | 435/6 |
| 2005/0255512 A1 * | 11/2005 | Sorge et al. | 435/6 |
| 2006/0094036 A1 * | 5/2006 | Sorge et al. | 435/6 |
| 2006/0246469 A1 * | 11/2006 | Sorge | 435/6 |
| 2007/0099206 A1 * | 5/2007 | Sorge | 435/6 |
| 2007/0105138 A1 * | 5/2007 | Sorge | 435/6 |
| 2008/0008995 A1 * | 1/2008 | Sorge | 435/6 |

FOREIGN PATENT DOCUMENTS

WO    WO98/23774    6/1998

OTHER PUBLICATIONS

The Stratagene Castalog p. 39 (1988).*
A Practical Guide to Molecular Cloning (B. Perbal, 1984).
Ausubel et al., 1995, Short Protocols in Molecular biology, 3rd Edition, John Wiley & Sons.
Barany, PCR Methods and Applications 1:5-16 (1991).
Beaucage et al., 1981, Tetrahedron Letters, 22:1859.
Brown et al., 1979, Methods in Enzymology, 68:109.
Chirgwin et al., 1979, Biochemistry, 18:5294.
International search report. (PCT/US00/29663).
International Search Report. (PCT/US01/31670).
Derbershire et al., 1995, Methods. Enzymolo. 262:363.
Ehricht R., et al., Nucleic Acids Res. 25L4697-4699 (1997).
Fahy et al, PCR MEthods and Applications 1:25-33 (1991).

(Continued)

*Primary Examiner*—Ethan Whisenant
(74) *Attorney, Agent, or Firm*—Theodore Allen; Paul Nuzzi

(57) ABSTRACT

The present invention is directed to kits and compositions for generating a signal indicative of the presence of a target nucleic acid sequence in a sample, comprising a nucleic acid polymerase lacking 5' to 3' exonuclease activity and a thermostable FEN nuclease consisting of a 5' to 3' exonuclease and/or endonuclease activity.

32 Claims, 13 Drawing Sheets

OTHER PUBLICATIONS

Hosfield et al., 1998a, Cell., 95:135.
Hosfield et al., 1998b, J. Biol. Chem., 273:27154.
Hosfield, et al. (1998), Cell., 95:135-145.
International Search Report, PCT/US01/44215.
Kaiser et al., 1999, J. Biol. Chem. 274:21387-21394.
Kanehisa, M., 1984, Nucleic Acids Res. 12:203.
Kim et al., 1997, Mol. Cells, 7:468.
Kim et al., 1998, J. Biol. Chem. 273:8842-8.
Klenow et al., 1970, Proc. Natl. Acad. Sci., USA, 65:168.
Klenow et al., 1971, Eur. J. Biochem., 22:371.
Landegren et al., 1988, Science, 241: 1077.
Lawyer et al., 1993, PCR Methods Appl., 2:275.
Leone, et al., 1998, Nucleic Acids Res., 26:2150.
Lieber, 1997, BioEssays, 19:233.
Livak, et al, Oligonucleotides with Fluorescent Dyes at Opposite Ends Provide a Quenched Probe System Useful for Detecting PCR Product and Nucleic Acid Hybridization, PCR Methods and Applications, Cold Harbor Laboratory Press, 1995, p. 357-362.
Lundberg et al., 1991 Gene, 108:1-6.
Lyamichev et al. Nature Biotechnology. vol. 17. Mar. 1999. pp. 292-296.
Lyamichev, et al, Polymorphism Identification And Quantitative Detection Of Genomic DNA by Invasive Cleavage Of Oligonucleotide Probes, Nature Biotechnology, vol. 17, 1999, p. 292-296.
Lyamichev, et al, Structure-Specific Endonucleolytic Cleavage of Nucleic Acids by Eubacterial DNA Polymerases, Science, vol. 260, 1993, p. 778-783.
Lyamichev, et al. (1999), Nature Biotechnology, 17L292-296.
Matsui et al., Thermostable Flap Endonuckease from the Archaeon, Pyrococcus horeikoshii, Cleaves the Replication Fork-like Structure Endo/Exonucleolytically, The Journal of Biological Chemistry, 1999, vol. 274, No. 26. pp. 18297-18309.
McHenry et al., 1997 J. Mol. biol, 272:178.
Mullis and Faloona, 1987. Methods Enzymol., 155:335.
Narang et al., 1979, Methods in Enzymology, 68:90.
Nucleic Acid Hybridization (B.d. Harnes & S.J. Higgins, eds., 1984.
Oligonucleotide Synthesis (M.J. Gait, ed., 1984).
Rumbaugh et al., 1999, J. Biol. Chem., 274:14602.
Sacchi et al, 1987, Anal. Biochem., 162: 156).
Saiki et al, 1985, Science 230:1350.
Saiki et al, 1986, Nature 324:163.
Saiki, et al. (1985), Science, 230:1350-1354.
Sambrook, Fritsch & Maniatis, 1989, Molecular cloning: A Laboratory Manual, Second Edition.
Tabor and Richardson, 1985, Proc. Natl. Acad. Sci, USA, 82:1074.
Tyagi S and Kramer FR, Nature Biotechnology 14: 303-308 (1996).
Walker, 1992, Proc. Natl. Acad. Sci, USA, 89:392.
Wu et al., 1996, Nuc. Acids Res., 24:2036-2043.
Wyborski et al, 1997, Strategies, 10:1.
Xu et al., 1997, J. Mol. Biol, 268:294.
Yi-Ping et al., 1999, J. Mol. Evol., 48:756.

* cited by examiner

OPEN CIRCLE PROBE

= TARGET PROBE (LEFT AND RIGHT TARGET PROBES)

= PROMOTER

= PRIMER COMPLEMENT

= DETECTION TAGS (OR SECONDARY TARGETS)

= GAP OLIGONUCLEOTIDE

FIG. 10

COMPOSITIONS AND KITS FOR DETECTION OF A TARGET NUCLEIC ACID

RELATED APPLICATIONS

This application is a continuation-in-part application of U.S. application Ser. No. 11/106,237, filed Apr. 14, 2005, now U.S. Pat. No. 7,482,121 which is a divisional application of U.S. application Ser. No. 09/728,574, now U.S. Pat. No. 7,118,860, which was filed on Nov. 30, 2000. U.S. application Ser. No. 09/728,574 is a continuation-in-part of U.S. application Ser. No. 09/650,888, filed Aug. 30, 2000, now U.S. Pat. No. 6,548,250, which is a continuation-in-part of U.S. application Ser. No. 09/430,692, filed Oct. 29, 1999, now U.S. Pat. No. 6,528,254. The entire teachings of the above applications are incorporated herein by reference.

FIELD OF THE INVENTION

The invention relates in general to methods of detecting or measuring a target-nucleic acid sequence.

BACKGROUND OF THE INVENTION

The fidelity of DNA replication, recombination, and repair is essential for maintaining genome stability, and all of these processes depend on 5'→3' exonuclease enzymes which are present in all organisms. For DNA repair, these enzymes are required for damaged fragment excision and recombinational mismatch correction. For replication, these nucleases are critical for the efficient processing of Okazaki fragments during lagging strand DNA synthesis. In *Escherichia coli*, this latter activity is provided by DNA polymerase I (PolI); *E. coli* strains with inactivating mutations in the PolI 5'→3'→ exonuclease domain are not viable due to an inability to process Okazaki fragments. Eukaryotic DNA polymerases, however, lack an intrinsic 5'→3' exonuclease domain, and this critical activity is provided by the multifunctional, structure-specific metallonuclease FEN-1 (five' exonuclease-1 or flap endonuclease-1), which also acts as an endonuclease for 5' DNA flaps (Reviewed in Hosfield et al., 1998a, *Cell*, 95:135).

Methods of detecting and/or measuring a nucleic acid wherein, an enzyme produces a labeled nucleic acid fragment are known in the art.

U.S. Pat. Nos. 5,843,669, 5,719,028, 5,837,450, 5,846,717 and 5,888,780 disclose a method of cleaving a target DNA molecule by incubating a 5' labeled target DNA with a DNA polymerase isolated from *Thermus aquaticus* (Taq polymerase) and a partially complementary oligonucleotide capable of hybridizing to sequences at the desired point of cleavage. The partially complementary oligonucleotide directs the Taq polymerase to the target DNA through formation of a substrate structure containing a duplex with a 3' extension opposite the desired site of cleavage wherein the non-complementary region of the oligonucleotide provides a 3' arm and the unannealed 5' region of the substrate molecule provides a 5' arm. The partially complementary oligonticleotide includes a 3' nucleotide extension capable of forming a short hairpin. The release of labeled fragment is detected following cleavage by Taq polymerase.

U.S. Pat. Nos. 5,843,669, 5,719,028, 5,837,450, 5,846,717 and 5,888,780 disclose the generation of mutant, thermostable DNA polymerases that have very little or no detectable synthetic activity, and wild type thermostable nuclease activity. The mutant polymerases are said to be useful because they lack 5' to 3' synthetic activity; thus synthetic activity is an undesirable side reaction in combination with a DNA cleavage step in a detection assay.

U.S. Pat. Nos. 5,843,669, 5,719,028, 5,837,450, 5,846,717 and 5,888,780 disclose that wild type Taq polymerase or mutant Taq polymerases that lack synthetic activity can release a labeled fragment by cleaving a 5' end labeled hairpin structure formed by heat denaturation followed by cooling in the presence of a primer that binds to the 3' arm of the hairpin structure. Further, U.S. Pat. Nos. 5,843,669, 5,719,028, 5,837,450, 5,846,717 and 5,888,780 teach that the mutant Taq polymerases lacking synthetic activity can also cleave this hairpin structure in the absence of a primer that binds to the 3' arm of the hairpin structure.

U.S. Pat. Nos. 5,843,669, 5,719,028, 5,837,450, 5,846,717 and 5,888,780 also disclose that cleavage of this hairpin structure in the presence of a primer that binds to the 3' arm of the hairpin structure by mutant Taq polymerases lacking synthetic activity yields a single species of labeled cleaved product, while wild type Taq polymerase produces multiple cleavage products and converts the hairpin structure to a double stranded form in the presence of dNTPs, due to the high level of synthetic activity of the wild type Taq enzyme.

The 5' to 3' exonuclease activity of a nucleic acid polymerase can impair the amplification of certain nucleic acids. There is also a need in the art for a method of generating a signal using a nucleic acid cleavage reaction in the absence of a 5' to 3' exonuclease activity of a nucleic acid polymerase.

U.S. Pat. Nos. 5,843,669, 5,719,028, 5,837,450, 5,846,717 and 5,888,780 also disclose that mutant Taq polymerases exhibiting reduced synthetic activity, but not wild type Taq polymerase, can release a single labeled fragment by cleaving a linear nucleic acid substrate comprising a 5' end labeled target nucleic acid and a complementary oligonucleotide wherein the complementary oligonucleotide hybridizes to a portion of the target nucleic acid such that 5' and 3' regions of the target nucleic acid are not annealed to the oligonucleotide and remain single stranded.

There is a need in the art for a method of generating a signal of a discrete size that can be easily distinguished from oligonucleotide fragments that may arise from nuclease contaminants, using a nucleic acid cleavage reaction in the absence of 5' to 3' exonuclease activity of a nucleic acid polymerase.

U.S. Pat. Nos. 5,843,669, 5,719,028, 5,837,450, 5,846,717 and 5,888,780 also disclose a method of cleaving a labeled nucleic acid substrate at naturally occurring areas of secondary structure. According to this method, biotin labeled DNA substrates are prepared by PCR, mixed with wild type Taq polymerase or CleavaseBN (a mutant Taq polymerase with reduced synthetic activity and wild type 5' to 3' nuclease activity), incubated at 95° C. for 5 seconds to denature the substrate and then quickly cooled to 65° C. to allow the DNA to assume its unique secondary structure by allowing the formation of intra-strand hydrogen bonds between the complementary bases. The reaction mixture is incubated at 65° C. to allow cleavage to occur and biotinylated cleavage products are detected.

There is a need in the art for a method of generating a signal using a nucleic acid cleavage reaction in the absence of a 5' to 3' exonuclease activity of a nucleic acid polymerase wherein the cleavage structure is not required to contain areas of secondary structure.

Methods of detecting and/or measuring a nucleic acid wherein a FEN-1 enzyme is used to generate a labeled nucleic acid fragment are known in the art.

U.S. Pat. No. 5,843,669 discloses a method of detecting polymorphisms by cleavase fragment length polymorphism analysis using a thermostable FEN-1 nuclease in the presence or absence of a mutant Taq polymerase exhibiting reduced synthetic activity. According to this method, double stranded Hepatitis C virus (HCV) DNA fragments are labeled by using 5' end labeled primers (labeled with TMR fluorescent dye) in a PCR reaction. The TMR labeled PCR products are denatured by heating to 95° C. and cooled to 55° C. to generate a cleavage structure. U.S. Pat. No. 5,843,669 discloses that a cleavage structure comprises a region of a single stranded nucleic acid substrate containing secondary structure. Cleavage is carried out in the presence of CleavaseBN nuclease, FEN-1 nuclease derived from the archaebacteria *Methanococcus jannaschii* or both enzymes. Labeled reaction products are visualized by gel electrophoresis followed by fluoroimaging. U.S. Pat. No. 5,843,669 discloses that CleavaseBN nuclease and *Methanococcus jannaschii* FEN-1 nuclease produce cleavage patterns that are easily distinguished from each other, and that the cleavage patterns from a reaction containing both enzymes include elements of the patterns produced by cleavage with each individual enzyme but are not merely a composite of the cleavage patterns produced by each individual enzyme. This indicates that some of the fragments that are not cleaved by one enzyme (and which appear as a band in that enzyme's pattern) can be cleaved by a second enzyme in the same reaction mixture.

Lyamichev et al. disclose a method for detecting DNAs wherein overlapping pairs of oligonucleotide probes that are partially complementary to a region of target DNA are mixed with the target DNA to form a 5' flap region, and wherein cleavage of the labeled downstream probe by a thermostable FEN-1 nuclease produces a labeled cleavage product. Lyamichev et al. also disclose reaction conditions wherein multiple copies of the downstream oligonucleotide probe can be cleaved for a single target sequence in the absence of temperature cycling, so as to amplify the cleavage signal and allow quantitative detection of target DNA at sub-attomole levels (Lyamichev et al., 1999, *Nat. Biotechnol.*, 17:292).

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science*, 230:1350.

While the PCR technique is an extremely powerful method for amplifying nucleic acid sequences, the detection of the amplified material requires additional manipulation and subsequent handling of the PCR products to determine whether the target DNA is present. It is desirable to decrease the number of subsequent handling steps currently required for the detection of amplified material. An assay system, wherein a signal is generated while the target sequence is amplified, requires fewer handling steps for the detection of amplified material, as compared to a PCR method that does not generate a signal during the amplification step.

U.S. Pat. Nos. 5,210,015 and 5,487,972 disclose a PCR based assay for releasing labeled probe comprising generating a signal during the amplification step of a PCR reaction in the presence of a nucleic acid to be amplified, Taq polymerase that has 5' to 3' exonuclease activity and a 5', 3' or 5' and 3' end-labeled probe comprising a region complementary to the amplified region and an additional non-complementary 5' tail region. U.S. Pat. Nos. 5,210,015 and 5,487,972 disclose further that this PCR based assay can liberate the 5' labeled end of a hybridized probe when the Taq polymerase is positioned near the labeled probe by an upstream probe in a polymerization independent manner, e.g. in the absence of dNTPs.

There is a need in the art for a method of detecting or measuring a target nucleic acid sequence that does not require multiple steps.

There is also a need in the art for a PCR process for detecting or measuring a target nucleic acid sequence that does not require multiple steps subsequent to the amplification process.

There is also a need in the art for a PCR process for detecting or measuring a target nucleic acid sequence that allows for concurrent amplification and detection of a target nucleic acid sequence in a sample.

There is also a need in the art for a PCR process for detecting or measuring a target nucleic acid sequence wherein the PCR process occurs in the presence of a nucleic acid polymerase that lacks 5' to 3' exonuclease activity.

SUMMARY OF THE INVENTION

The invention provides a method of generating a signal indicative of the presence of a target nucleic acid sequence in a sample comprising forming a cleavage structure by incubating a sample comprising a target nucleic acid sequence with a nucleic acid polymerase, and cleaving the cleavage structure with a FEN nuclease to generate a signal, wherein generation of the signal is indicative of the presence of a target nucleic acid sequence in the sample.

As used herein a "FEN nuclease" refers to an enzyme that cleaves a cleavage structure according to the invention. The term "FEN nuclease" encompasses an enzyme that consists essentially of a 5' exonuclease and/or an endonuclease activity. As used herein, "consists essentially of" refers to an enzyme wherein the predominant activity of the enzyme is a 5' exonucleolytic and/or endonucleolytic activity, such that one or both of 5' to 3' synthetic activity and 3' single-stranded flap cleavage activity (i.e., 3' endonucleolytic and/or 3' exonucleolytic activity) are substantially lacking. "Substantially lacks" means that the FEN nuclease possesses no more than 5% or 10% and preferably less than 0.1%, 0.5%, or 1% of the activity of a wild type enzyme (e.g. for 5' to 3' synthetic activity and the 3' endonucleolytic and/or '3 exonucleolytic activities, the enzyme may be a wild type DNA polymerase having these activities). 5' to 3' synthetic activity can be measured, for example, in a nick translation assay or an enzymatic sequencing reaction which involve the formation of a phosphodiester bridge between the 3'-hydroxyl group at the growing end of an oligonucleotide primer and the 5'-phosphate group of an incoming deoxynucleotide, such that the overall direction of synthesis is in the 5' to 3' direction. 3' flap cleavage ma measured in a DNA synthesis reaction in which, because the (labeled) 3' end of a DNA duplex is unpaired, it is cleaved from the duplex. A FEN nuclease that "consists of" a 5' exonuclease and/or endonuclease activity refers to an enzyme that "lacks" 5' to 3' synthetic activity and/or 3' single-stranded flap cleavage activity. "Lacks" means that the Fen nuclease has no detectable activity or has only "minor" activity, i.e., less than 1.0%, 0.5%, 0.1% or 0.01% of the activity of a wild type enzyme. As used herein, "FEN nuclease" encompasses a 5' flap-specific nuclease.

As used herein, "wild type" refers to a gene or gene product which has the characteristics of (i.e., either has the sequence of or encodes, for the gene, or possesses the sequence or activity of, for an enzyme) that gene or gene product when isolated from a naturally occurring source.

A "5' flap-specific nuclease" (also referred to herein as a "flap-specific nuclease") according to the invention is an endonuclease which can remove a single stranded flap that protrudes as a 5' single strand. A flap-specific nuclease according to the invention can also cleave a pseudo-Y structure. A substrate of a flap-specific nuclease according to the invention, comprises a target nucleic acid, a second nucleic acid, a portion of which specifically hybridizes with a target nucleic acid, and a primer extension product from a third nucleic acid that specifically hybridizes with a target nucleic acid sequence.

As used herein, a "cleavage structure" refers to a polynucleotide structure (for example as illustrated in FIG. 1) comprising at least a duplex nucleic acid having a single stranded region comprising a flap, a loop, a single-stranded bubble, a D-loop, a nick or a gap. A cleavage structure according to the invention thus includes a polynucleotide structure comprising a flap strand of a branched DNA wherein a 5' single-stranded polynucleotide flap extends from a position near its junction to the double stranded portion of the structure and preferably the flap is labeled with a detectable label. A flap of a cleavage structure according to the invention is preferably about 1-500 nucleotides, more preferably about 5-25 nucleotides and most preferably about 10-20 nucleotides and is preferably cleaved at a position located either one nucleotide proximal and/or one nucleotide distal from the elbow of the flap strand.

A cleavage structure according to the invention preferably comprises a target nucleic acid sequence, and also may include an oligonucleotide that specifically hybridizes with the target nucleic acid sequence, and a flap extending from the hybridizing oligonucleotide. For example, a cleavage structure according to the invention may comprise a target nucleic acid sequence (for example B in FIG. 3), an upstream oligonucleotide that is complementary to the target sequence (for example A in FIG. 3), and a downstream oligonucleotide that is complementary to the target sequence (for example C in FIG. 3). In such a cleavage structure, the downstream oligonucleotide may be blocked at the 3' terminus to prevent extension of the 3' end of the downstream oligonucleotide.

A cleavage structure according to the invention may be a polynucleotide structure& comprising a flap extending from the downstream oligonucleotide, wherein the flap is formed by extension of the upstream oligonucleotide by the synthetic activity of a nucleic acid polymerase, and subsequent, partial, displacement of the 5' end of the downstream oligonucleotide.

A cleavage structure according to the invention may be formed by hybridizing a target nucleic acid sequence with an oligonucleotide wherein the oligonucleotide comprises a complementary region that anneals to the target nucleic acid sequence, and a non-complementary region that does not anneal to the target nucleic acid sequence and forms a 5' flap.

A cleavage structure also may be a pseudo-Y structure wherein a pseudo Y-structure is formed if the strand upstream of a flap (referred to herein as a flap adjacent strand or primer strand) is removed, and double stranded DNA substrates containing a gap or nick. A "cleavage structure", as used herein does not include a double stranded nucleic acid structure with only a 3' single-stranded flap. As used herein, a "cleavage structure" comprises ribonucleotides or deoxyribonucleotides and thus can be RNA or DNA.

A cleavage structure according to the invention may be an overlapping flap wherein the 3' end of an upstream oligonucleotide capable of hybridizing to a target nucleic acid sequence (for example A in FIG. 3) is complementary to 1 base pair of the downstream oligonucleotide (for example C in FIG. 3) that is annealed to a target nucleic acid sequence and wherein the overlap is directly downstream of the point of extension of the single stranded flap.

A cleavage structure according to the invention is formed by the steps of 1. incubating a) an upstream extendable 3' end, preferably an oligonucleotide primer, b) an oligonucleotide primer probe located not more than 5000 nucleotides downstream of the upstream primer and c) an appropriate target nucleic acid sequence wherein the target sequence is complementary to both the upstream primer and downstream probe and d) a suitable buffer, under conditions that allow the nucleic acid sequence to hybridize to the oligonucleotide primers, and 2. extending the 3' end of the upstream oligonucleotide primer by the synthetic activity of a polymerase such that the newly synthesized 3' end of the upstream oligonucleotide primer becomes adjacent to and/or displaces at least a portion of (i.e., at least 5-10 nucleotides of) the 5' end of the downstream oligonucleotide probe. According to the method of the invention, buffers and extension temperatures are favorable for strand displacement by a particular nucleic acid polymerase according to the invention. Preferably, the downstream oligonucleotide is blocked at the 3' terminus to prevent extension of the 3' end of the downstream oligonucleotide. In another embodiment of the invention, a cleavage structure according to the invention can be prepared by incubating a target nucleic acid sequence with an oligonucleotide primer comprising a non-complementary 5' region that does not anneal to the target nucleic acid sequence and forms a 5' flap, and a complementary 3' region that anneals to the target nucleic acid sequence.

In a preferred embodiment of the invention a cleavage structure is labeled. A labeled cleavage structure according to the invention is formed by the steps of 1. incubating a) an upstream extendable 3' end, preferably an oligonucleotide primer, b) a labeled probe preferably located not more than 5000 and more preferably located not more than 500 nucleotides downstream of the upstream primer and c) an appropriate target nucleic acid sequence wherein the target sequence is complementary to both the primer and the labeled probe and d) a suitable buffer, under conditions that allow the nucleic acid sequence to hybridize to the primers, and 2. extending the 3' end of the upstream primer by the synthetic activity of a polymerase such that the newly synthesized 3' end of the upstream primer partially displaces the 5' end of the downstream probe. According to the method of the invention, buffers and extension temperatures are favorable for strand displacement by a particular nucleic acid polymerase according to the invention. Preferably, the downstream oligonucleotide is blocked at the 3' terminus to prevent extension of the 3' end of the downstream oligonucleotide. In another embodiment, a cleavage structure according to the invention can be prepared by incubating a target nucleic acid sequence with a probe comprising a non-complementary labeled, 5' region that does not anneal to the target nucleic acid sequence and forms a 5' flap, and a complementary 3' region that anneals to the target, nucleic acid sequence.

As used herein, "label" or "labeled moiety capable of providing a signal" refers to any atom or molecule which can be used to provide a detectable (preferably quantifiable) signal, and which can be operatively linked to a nucleic acid. Labels may provide signals detectable by fluorescence, radioactivity, colorimetry, gravimetry, X-ray diffraction or absorption, magnetism, enzymatic activity, mass spectrometry, binding affinity, hybridization radiofrequency and the like.

As used herein, "generating a signal" refers to detecting and or measuring a released nucleic acid fragment as an indication of the presence of a target nucleic acid sequence in a sample.

As used herein, "sample" refers to any substance containing or presumed to contain a nucleic acid of interest (a target nucleic acid sequence) or which is itself a nucleic acid containing or presumed to contain a target nucleic acid sequence of interest. The term "sample" thus includes a sample of nucleic acid (genomic DNA, cDNA, RNA), cell, organism, tissue, fluid, or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials), microbial specimens, and objects or specimens that have been "marked" with nucleic acid tracer molecules.

As used herein, "target nucleic acid sequence" or "template nucleic acid sequence" refers to a region of a nucleic acid that is to be either replicated, amplified, and/or detected. In one embodiment, the "target nucleic acid sequence" or "template nucleic acid sequence" resides between two primer sequences used for amplification.

As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template, and if possessing a 5' to 3' nuclease activity, hydrolyzing intervening, annealed probe to release both labeled and unlabeled probe fragments, until synthesis terminates. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

As used herein, "5' to 3' exonuclease activity" or "5'→3' exonuclease activity" refers to that activity of a template-specific nucleic acid polymerase e.g. a 5'→3' exonuclease activity traditionally associated with some DNA polymerases whereby mononucleotides or oligonucleotides are removed from the 5' end of a polynucleotide in a sequential manner, (i.e., *E. coli* DNA polymerase I has this activity whereas the Klenow (Klenow et al., 1970, *Proc. Natl. Acad. Sci., USA*, 65:168) fragment does not, (Klenow et al., 1971, *Eur. J. Biochem.*, 22:371)), or polynucleotides are removed from the 5' end by an endonucleolytic activity that may be inherently present in a 5' to 3' exonuclease activity.

As used herein, the phrase "substantially lacks 5' to 3' exonuclease activity" or "substantially lacks 5'→3' exonuclease activity" means having less than 10%, 5%, 1%, 0.5%, or 0.1% of the activity of a wild type enzyme. The phrase "lacking 5' to 3' exonuclease activity" or "lacking 5'→3' exonuclease activity" means having undetectable 5' to 3' exonuclease activity or having less than about 1%, 0.5%, or 0.1% of the 5' to 3' exonuclease activity of a wild type enzyme. 5' to 3' exonuclease activity may be measured by an exonuclease assay which includes the steps of cleaving a nicked substrate in the presence of an appropriate buffer, for example 10 mM Tris-HCl (pH 8.0), 10 mM $MgCl_2$ and 50 μg/ml bovine serum albumin) for 30 minutes at 60° C., terminating the cleavage reaction by the addition of 95% formamide containing 10 mM EDTA and 1 mg/ml bromophenol blue, and detecting nicked or un-nicked product.

Nucleic acid polymerases useful according to the invention include but are not limited to Pfu, exo-Pfu (a mutant form of Pfu that lacks 3' to 5' exonuclease activity), the Stoffel fragment of Taq, N-truncated Bst, N-truncated Bca, Genta, JdF3 exo-, Vent, Vent exo- (a mutant form of Vent that lacks 3' to 5' exonuclease activity), Deep Vent, Deep Vent exo- (a mutant form of Deep Vent that lacks 3' to 5' exonuclease activity), U1Tma and Sequenase. Additional nucleic acid polymerases useful according to the invention are included below in the section entitled, "Nucleic Acid Polymerases".

As used herein, "cleaving" refers to enzymatically separating a cleavage structure into distinct (i.e. not physically linked to other fragments or nucleic acids by phosphodiester bonds) fragments or nucleotides and fragments that are released from the cleavage structure. For example, cleaving a labeled cleavage structure refers to separating a labeled cleavage structure according to the invention and defined below, into distinct fragments including fragments derived from an oligonucleotide that specifically hybridizes with a target nucleic acid sequence or wherein one of the distinct fragments is a labeled nucleic acid fragment derived from a target nucleic acid sequence and/or derived from an oligonucleotide that specifically hybridizes with a target nucleic acid sequence that can be detected and/or measured by methods well known in the art and described herein that are suitable for detecting the labeled moiety that is present on a labeled fragment.

As used herein, "endonuclease" refers to an enzyme that cleaves bonds, preferably phosphodiester bonds, within a nucleic acid molecule. An endonuclease according to the invention can be specific for single-stranded or double-stranded DNA or RNA.

As used herein, "exonuclease" refers to an enzyme that cleaves bonds, preferably phosphodiester bonds, between nucleotides one at a time from the end of a polynucleotide. An exonuclease according to the invention can be specific for the 5' or 3' end of a DNA or RNA molecule, and is referred to herein as a 5' exonuclease or a 3' exonuclease.

As used herein a "flap" refers to a region of single stranded DNA that extends from a double stranded nucleic acid molecule. A flap according to the invention is preferably between about 1-500 nucleotides, more preferably between about 5-25 nucleotides and most preferably between about 10-20 nucleotides.

In a preferred embodiment, the nucleic acid polymerase substantially lacks 5' to 3' exonuclease activity.

In a preferred embodiment, the cleavage structure comprises at least one oligonucleotide primer.

The invention also provides a method of detecting or measuring a target nucleic acid sequence comprising forming a cleavage structure by incubating a sample comprising a target nucleic acid sequence with a nucleic acid polymerase, cleaving the cleavage structure with a FEN nuclease to release a nucleic acid fragment, and detecting and/or measuring the release of the fragment as an indication of the presence of the target sequence in the sample.

As used herein, "detecting a target nucleic acid sequence" or "measuring a target nucleic acid sequence" refers to determining the presence of a particular target nucleic acid sequence in a sample or determining the amount of a particular target nucleic acid sequence in a sample as an indication of the presence of a target nucleic acid sequence in a sample. The amount of a target nucleic acid sequence that can be measured or detected is preferably about 1 molecule to $10^{20}$ molecules, more preferably about 100 molecules to $10^{17}$ molecules and most preferably about 1000 molecules to $10^{14}$ molecules. According to the invention, the detected nucleic acid is derived from the labeled 5' end of a downstream probe of a cleavage structure according to the invention (for example C in FIG. 3), that is displaced from the target nucleic acid sequence by the 3' extension of an upstream probe of a cleavage structure according to the invention (for example A of FIG. 3). According to the present invention, a label is attached to the 5' end of the downstream probe (for example C in FIG. 3) comprising a cleavage structure according to the invention. Alternatively, a label is attached to the 3' end of the downstream probe and a quencher is attached to the 5' flap of the downstream probe. According to the invention, a label may be attached to the 3' end of the downstream probe (for example C in FIG. 3) comprising a cleavage structure according to the invention.

According to the invention, the downstream probe (for example C in FIG. 3) may be labeled internally. In a preferred embodiment, a cleavage structure according to the invention can be prepared by incubating a target nucleic acid sequence with a probe comprising a non-complementary, labeled, 5' region that does not anneal to the target nucleic acid sequence and forms a 5' flap, and a complementary 3' region that anneals to the target nucleic acid sequence. According to this embodiment of the invention, the detected nucleic acid is derived from the labeled 5' flap region of the probe. Preferably there is a direct correlation between the amount of the target nucleic acid sequence and the signal generated by the cleaved, detected nucleic acid.

As used herein, "detecting release of labeled fragments" or "measuring release of labeled fragments" refers to determining the presence of a labeled fragment in a sample or determining the amount of a labeled fragment in a sample. Methods well known in the art and described herein can be used to detect or measure release of labeled fragments. A method of detecting or measuring release of labeled fragments will be appropriate for measuring or detecting the labeled moiety that is present on the labeled fragments. The amount of a released labeled fragment that can be measured or detected is preferably about 25%, more preferably about 50% and most preferably about 95% of the total starting amount of labeled probe.

As used herein, "labeled fragments" refer to cleaved mononucleotides or small oligonucleotides or oligonucleotides derived from the labeled cleavage structure according to the invention wherein the cleaved oligonucleotides are preferably between about 2-1000 nucleotides, more preferably between about 5-50 nucleotides and most preferably between about 16-18 nucleotides, which are cleaved from a cleavage structure by a FEN nuclease and can be detected by methods well known in the art and described herein.

In a preferred embodiment, the nucleic acid polymerase substantially lacks 5' to 3' exonuclease activity.

In another preferred embodiment, the nucleic acid polymerase is a DNA polymerase.

In another preferred embodiment, the nucleic acid polymerase is thermostable.

As used herein, "thermostable" refers to an enzyme which is stable and active at temperatures as great as preferably between about 90-100° C. and more preferably between about 70-98° C. to heat as compared, for example, to a non-thermostable form of an enzyme with a similar activity. For example, a thermostable nucleic acid polymerase or FEN nuclease derived from thermophilic organisms such as *P. furiosus, M jannaschii, A. fulgidus* or *P. horikoshii* are more stable and active at elevated temperatures as compared to a nucleic acid polymerase from *E. coli* or a mammalian FEN enzyme. A representative thermostable nucleic acid polymerase isolated from *Thermus aquaticus* (Taq) is described in U.S. Pat. No. 4,889,818 and a method for using it in conventional PCR is described in Saiki et al., 1988, *Science* 239:487. Another representative thermostable nucleic acid polymerase isolated from *P. furiosus* (Pfu) is described in Lundberg et al., 1991, *Gene*, 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus*.

Temperature stable polymerases and FEN nucleases are preferred in a thermocycling process wherein double stranded nucleic acids are denatured by exposure to a high temperature (about 95° C.) during the PCR cycle.

In another preferred embodiment, the FEN nuclease is a flap-specific nuclease.

In another preferred embodiment, the FEN nuclease is thermostable.

In another preferred embodiment, the cleavage structure is formed comprising at least one labeled moiety capable of providing a signal.

In another preferred embodiment, the cleavage structure is formed comprising a pair of interactive signal generating labeled moieties effectively positioned to quench the generation of a detectable signal, wherein the labeled moieties are separated by a site susceptible to FEN nuclease cleavage, thereby allowing the nuclease activity of the FEN nuclease to separate the first interactive signal generating labeled moiety from the second interactive signal generating labeled moiety by cleaving at the site susceptible to FEN nuclease, thereby generating a detectable signal.

In yet another preferred embodiment, the cleavage structure is formed comprising a hairpin-forming oligonucleotide probe having secondary structure.

As used herein, "secondary structure" refers to the conformation (for example a hairpin, a stem-loop structure, an internal loop, a bulge loop, a branched structure, or a pseudoknot) of a nucleic acid molecule wherein a sequence comprising a first single stranded sequence of bases followed by a second complementary sequence in the same molecule folds back on itself to generate an antiparallel duplex structure wherein the single stranded sequence and the complementary sequence anneal by the formation of hydrogen bonds. A "secondary structure" also refers to the conformation of a nucleic acid molecule comprising an affinity pair, wherein the affinity pair reversibly associates as a result of attractive forces that exist between the moieties. As used herein, "secondary structure" refers to a nucleic acid conformation which prevents probe binding to a capture element.

As used herein, a "hairpin structure" or a "stem" refers to a double-helical region formed by base pairing between adjacent, inverted, complementary sequences in a single strand of RNA of DNA.

As used herein, "stem loop" structure refers to a hairpin structure, further comprising a loop of unpaired bases at one end.

In another preferred embodiment, the pair of interactive signal generating moieties comprises a quencher moiety and a fluorescent moiety.

In another preferred embodiment, the cleavage structure comprises at least one oligonucleotide primer.

The invention also provides a polymerase chain reaction process for detecting a target nucleic acid sequence in a sample comprising providing a cleavage structure, providing a set of oligonucleotide primers wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand, and amplifying the target nucleic acid sequence employing a nucleic acid polymerase as a template-dependent polymerizing agent under conditions which are permissive for PCR cycling steps of (i) annealing of primers required for amplification to a template nucleic acid sequence contained within the target sequence and annealing primers required for formation of a cleavage structure to a target nucleic acid sequence; (ii) extending the primers wherein the nucleic acid polymerase synthesizes a primer extension product, and (iii) cleaving the cleavage structure employing a FEN nuclease as a cleavage agent for release of labeled fragments from the cleavage structure thereby creating detectable labeled fragments; and (d) detecting and/or measuring the release of labeled fragments as an indication of the presence of the target nucleic acid sequence in the sample.

The invention provides for a polymerase chain reaction process wherein amplification and detection of a target nucleic acid sequence occur concurrently (i.e. real time detection). The invention also provides for a polymerase chain reaction process wherein amplification of a target nucleic acid sequence occurs prior to detection of the target nucleic acid sequence (i.e. end point detection).

As used herein, an "oligonucleotide primer" refers to a single stranded DNA or RNA molecule that can hybridize to a nucleic acid template and primes enzymatic synthesis of a second nucleic acid strand. Oligonucleotide primers useful according to the invention are between about 10 to 100 nucleotides in length, preferably about 17-50 nucleotides in length and more preferably about 17-45 nucleotides in length. Oligonucleotide probes useful for the formation of a cleavage structure according to the invention are between about 17-40 nucleotides in length, preferably about 17-30 nucleotides in length and more preferably about 17-25 nucleotides in length. Oligonucleotide probes, as used in the present invention include oligonucleotides comprising secondary structure, including, but not limited to molecular beacons, safety pins (FIG. 10), scorpions (FIG. 11), and sunrise/amplifluor probes (FIG. 12), the details and structures of which are described below and in the corresponding figures.

As used herein, "template dependent polymerizing agent" refers to an enzyme capable of extending an oligonucleotide primer in the presence of adequate amounts of the four deoxyribonucleoside triphosphates (dATP, dGTP, dCTP and dTTP) or analogs as described herein, in a reaction medium comprising appropriate salts, metal cations, appropriate stabilizers and a pH buffering system. Template dependent polymerizing agents are enzymes known to catalyze primer- and template-dependent DNA synthesis, and possess 5' to 3' nuclease activity. Preferably, a template dependent polymerizing agent according to the invention lacks 5' to 3' nuclease activity.

As used herein, "amplifying" refers to producing additional copies of a nucleic acid sequence, including the method of the polymerase chain reaction.

In a preferred embodiment, the nucleic acid polymerase substantially lacks 5' to 3' exonuclease activity.

In a preferred embodiment, the oligonucleotide primers of step b of the polymerase chain reaction process described above are oriented such that the forward primer is located upstream of a cleavage structure according to the invention and the reverse primer is located downstream of a cleavage structure according to the invention. The reverse primer is complementary to the opposite strand of the forward primer which is complementary to a strand of the cleavage structure.

In another preferred embodiment, the nucleic acid polymerase is a DNA polymerase.

In another preferred embodiment, the nucleic acid, polymerase is thermostable.

In another preferred embodiment, the nucleic acid polymerase is selected from the group consisting of Taq polymerase and Pfu polymerase.

In another preferred embodiment the FEN nuclease is thermostable.

In another preferred embodiment the FEN nuclease is a flap-specific nuclease.

In another preferred embodiment the FEN nuclease is selected from the group consisting, of FEN nuclease enzyme derived from *Archaeglobus fulgidus*, *Methanococcus jannaschii*, *Pyrococcus furiosus*, human, mouse or *Xeniopus laevis*. A FEN nuclease according to the invention also includes *Saccharomyces cerevisiae* RAD27, and *Schizosaccharomyces pombe* RAD2, Pol I DNA polymerase associated 5' to 3' exonuclease domain, (e.g. *E. coli*, *Thermus aquaticus* (Taq), *Thermus flavus* (Tfl), *Bacillus caldotenax* (Bca), *Streptococcus pneumoniae*) and phage functional homologs of FEN including but not limited to T4 RnaseH, T5 5' to 3' exonuclease, T7 gene 6 exonuclease and T3 gene 6 exonuclease.

Preferably, only the 5' to 3' exonuclease domains of Taq, Tfl and Bca FEN nuclease are used.

In another preferred embodiment, the labeled cleavage structure is formed by the addition of at least one labeled moiety capable of providing a signal.

The invention also provides a polymerase chain reaction process for simultaneously forming a cleavage structure, amplifying a target nucleic acid sequence in a sample and cleaving the cleavage structure comprising: (a) providing an upstream oligonucleotide primer complementary to a region in one strand of the target nucleic acid sequence and a downstream labeled probe complementary to a region in the same strand of the target nucleic acid sequence, wherein the upstream primer contains a sequence complementary to a region in one strand of the target nucleic acid sequence and primes the synthesis of a complementary DNA strand, and the downstream probe contains a sequence complementary to a region in a second strand of the target nucleic acid sequence and primes the synthesis of a complementary DNA strand; and (b) detecting a nucleic acid which is produced in a reaction comprising amplification of the target nucleic acid sequence and cleavage thereof wherein a nucleic acid polymerase is a template-dependent polymerizing agent under conditions which are permissive for PCR cycling steps of (i) annealing of primers to a target nucleic acid sequence, (ii) extending the primers of step (a) wherein the nucleic acid polymerase synthesizes primer extension products, and wherein the primer extension product of the primer of step (a) partially displaces the downstream probe of step (a) to form a cleavage structure; and (iii) cleaving the cleavage structure employing a FEN nuclease as a cleavage agent for release of labeled fragments from the cleavage structure thereby creating detectable labeled fragments.

In a preferred embodiment, the nucleic acid polymerase substantially lacks 5' to 3' exonuclease activity.

The invention also provides a method of forming a cleavage structure comprising the steps of: (a) providing a target nucleic acid sequence, (b) providing an upstream primer complementary to said target nucleic acid sequence, (c) providing a downstream probe complementary to said target nucleic acid sequence, (d) extending the 3' end of the upstream primer with a nucleic acid polymerase; and (e) displacing the 5' end of the downstream probe.

Preferably the downstream probe is located not more than 500 nucleotides downstream of the upstream primer.

During the extension step, the 3' end of the upstream primer is extended by the synthetic activity of a polymerase such that the newly synthesized 3' end of the upstream primer partially displaces the 5' end of the downstream probe.

In a preferred embodiment, the nucleic acid polymerase substantially lacks 5' to 3' exonuclease activity.

In another embodiment of the invention, a cleavage structure according to the invention can be prepared by incubating a target nucleic acid sequence with a probe comprising a non-complementary 5' region that does not anneal to the target nucleic acid sequence and forms a 5' flap, and a complementary 3' region that anneals to the target nucleic acid sequence.

The invention also provides a method of forming a labeled cleavage structure comprising the steps of: (a) providing a target nucleic acid sequence, (b) providing an upstream primer complementary to said target nucleic acid sequence, (c) providing a downstream end labeled probe complementary to said target nucleic acid sequence, (d) extending the 3' end of the upstream primer with a nucleic acid polymerase; and (e) displacing the 5' end of the downstream probe.

Preferably the downstream end labeled probe is located not more than 500 nucleotides downstream of the upstream primer. Preferably, the downstream oligonucleotide is blocked at the 3' terminus to prevent extension of the 3' end of the downstream oligonucleotide. Such blockage can be achieved by placing a phosphate, or other moiety not readily removed, on the 3' terminal hydroxyl of the oligonucleotide.

During the extension step, the 3' end of the upstream primer is extended by the synthetic activity of a polymerase such that the newly synthesized 3' end of the upstream primer partially displaces the 5' end of the downstream probe. According to the method of the invention, buffers and extension temperatures are favorable for strand displacement by a particular nucleic acid polymerase according to the invention.

In one embodiment of the invention, a cleavage structure according to the invention can be prepared by incubating a target nucleic acid sequence with a probe comprising a non-complementary, labeled, 5' region that does not anneal to the target nucleic acid sequence and forms a 5' flap, and a complementary 3' region that anneals to the target nucleic acid sequence.

The invention also provides a kit for generating a signal indicative of the presence of a target nucleic acid sequence in a sample comprising a nucleic acid polymerase, a FEN nuclease and a suitable buffer. In a preferred embodiment, the invention also provides a kit for generating a signal indicative of the presence of a target nucleic acid sequence in a sample comprising one or more nucleic acid polymerases, a FEN nuclease and a suitable buffer.

In a preferred embodiment, the nucleic acid polymerase substantially lacks 5' to 3' exonuclease activity.

In a preferred embodiment the nucleic acid polymerase is thermostable.

In another preferred embodiment the FEN nuclease is thermostable.

In another preferred embodiment the kit further comprises a labeled nucleic acid complementary to the target nucleic acid sequence.

The invention also provides a composition comprising a nucleic acid polymerase and a FEN nuclease.

In a preferred embodiment, the nucleic acid polymerase substantially lacks a 5' to 3' exonuclease activity.

In another preferred embodiment the invention provides for a composition comprising one or more nucleic acid polymerases and a FEN nuclease.

Further features and advantages of the invention are as follows. The claimed invention provides a method of generating a signal to detect and/or measure a target nucleic acid wherein the generation of a signal is an indication of the presence of a target nucleic acid in a sample. The method of the claimed invention does not require multiple steps. The claimed invention also provides a PCR based method for detecting and/or measuring a target nucleic acid comprising generating a signal as an indication of the presence of a target nucleic acid. The claimed invention allows for simultaneous amplification and detection and/or measurement of a target nucleic acid sequence. The claimed invention also provides a PCR based method for detecting and/or measuring a target nucleic acid comprising generating a signal in the absence of a nucleic acid polymerase that demonstrates 5' to 3' exonuclease activity.

Further features and advantages of the invention will become more fully apparent in the following description of the embodiments and drawings thereof, and from the claims.

BRIEF DESCRIPTION OF DRAWINGS

FIG. 10 is a representation of a safety pin probe.

DESCRIPTION

Figure 1:
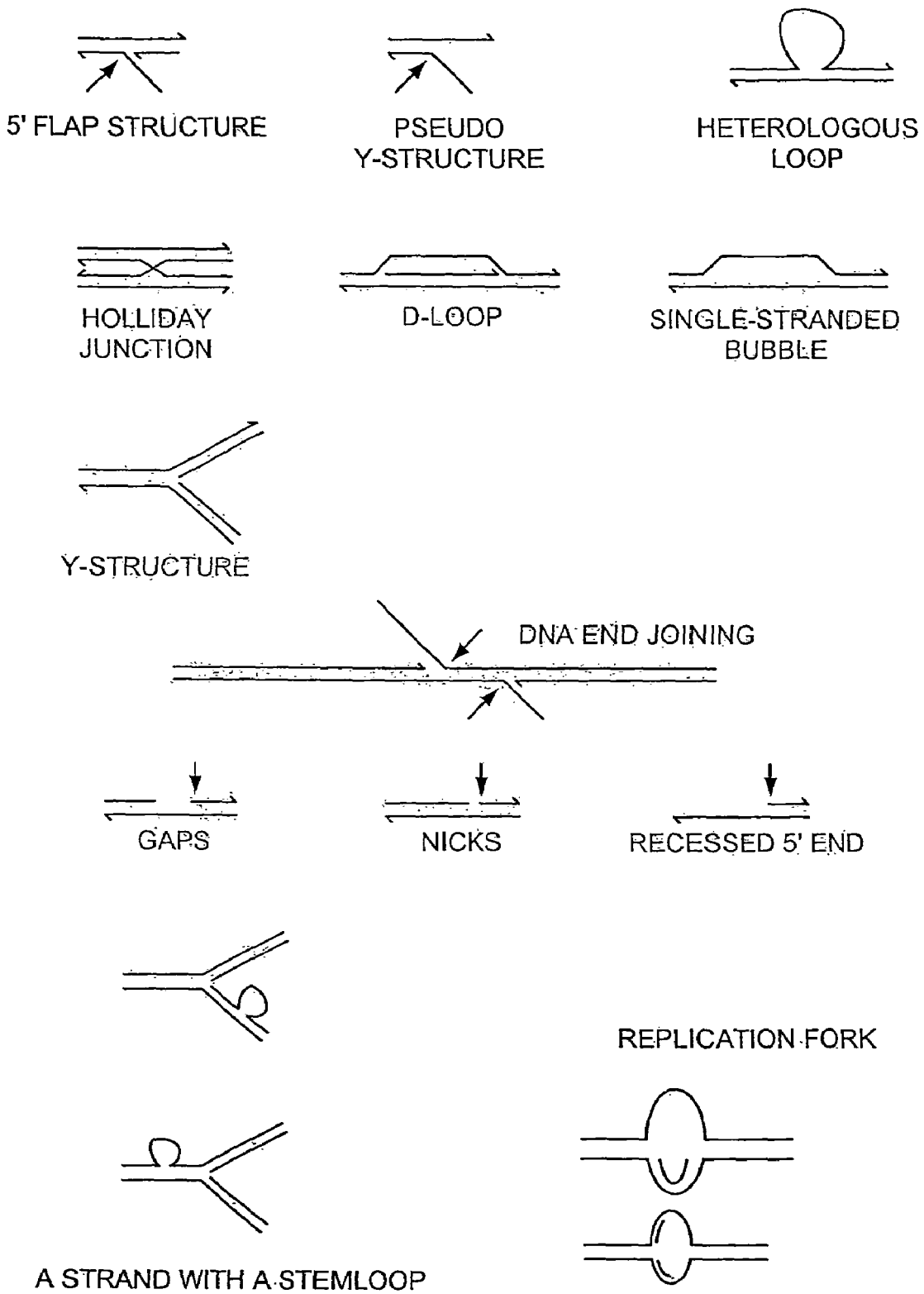
FIG. 1 demonstrates FEN nuclease cleavage structures.

The invention provides for a method of generating a signal to detect the presence of a target nucleic acid in a sample wherein a nucleic acid is treated with the combination of a nucleic acid polymerase and a FEN nuclease. The invention also provides for a process for detecting or measuring a nucleic acid that allows for concurrent amplification, cleavage and detection of a target nucleic acid sequence in a sample.

The practice of the present invention will employ, unless otherwise indicated, conventional techniques of molecular biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Hames & S. J. Higgins, eds., 1984); *A Practical Guide to Molecular*

*Cloning* (B. Perbal, 1984); and a series, *Methods in Enzymology* (Academic Press, Inc.). All patents, patent applications, and publications mentioned herein, both supra and infra, are hereby incorporated by reference.

I. FEN Nucleases

FEN-1 is an ~40 kDa divalent metal ion-dependent exo- and endonuclease that specifically recognizes the backbone of a 5' single-stranded flap strand and tracks down this arm to the cleavage site, which is located at the junction wherein the two strands of duplex DNA adjoin the single-stranded arm. Both the endo- and exonucleolytic activities show little sensitivity to the base at the most 5' position at the flap or nick. Both FEN-1 endo- and exonucleolytic substrate binding and cutting are stimulated by an upstream oligonucleotide (flap adjacent strand or primer). This is also the case for *E. coli* pol I. The endonuclease activity of the enzyme is independent of the 5' flap length, cleaving a 5' flap as small as one nucleotide. The endonuclease and exonuclease activities are insensitive to the chemical nature of the substrate, cleaving both DNA and RNA.

Both the endo- and exonucleolytic activities are inhibited by concentrations of salts in the physiological range. The exonuclease activity is inhibited 50-fold at 50 M NaCl as compared to 0 mM NaCl. The endonuclease activity is inhibited only sevenfold at 50 mM NaCl (Reviewed in Lieber 1997, supra).

Although a 5'-OH terminus is a good substrate for FEN-1 loading onto a 5' flap substrate, it serves as a very poor substrate when part of a nick in an otherwise double stranded DNA structure. The electrostatic repulsion by the terminal phosphate is likely to favor breathing of the substrate into a pseudo-flap configuration, providing the active form of the substrate for FEN-1. Such an explanation would indicate a single active site and a single mechanism of loading of FEN-1 onto the 5' ssDNA terminus of the flap or pseudo-flap configuration of the nick. Consistent with this model are observations that optimal activity at a nick requires very low $Mg^{2+}$ and monovalent salt concentrations, which destabilize base-pairing and would favor breathing of a nick to a flap. Higher $Mg^{2+}$ and monovalent salt concentrations would disfavor breathing and inhibit cutting of nicked or gapped structures that do require breathing to convert to a flap. Cleavage of stable flap structures is optimal at moderate $Mg^{2+}$ levels and does not decrease with increasing $Mg^{2+}$ concentration. This is because a flap substrate does not have to melt out base pairs to achieve its structure; hence, it is entirely insensitive to $Mg^{2+}$. Though the endonucleolytic activity decreases with monovalent salt, the decline is not nearly as sharp as that seen for the exonucleolytic activity. Furthermore, it has previously been shown that one-nucleotide flaps are efficient substrates. All of these observations are consistent with the fact that when FEN-1 has been interpreted to be functioning as an exonuclease, the size of the degradation products vary from one to several nucleotides in length. Breathing of nicks into flaps of varying length would be expected to vary with local sequence, depending on the G/C content. In summary, a nick breathing to form a transient flap means that the exonucleolytic activity of FEN-1 is the same as the endonucleolytic activity (Reviewed in Lieber, 1997, supra).

The endonuclease and exonuclease activities of FEN-1 cleave both DNA and RNA without requiring accessory proteins. At the replication fork, however, FEN-1 does interact with other proteins, including a DNA helicase and the proliferating cell nuclear antigen (PCNA), the processivity factor for DNA polymerases δ and ε. PCNA significantly stimulates FEN-1 endo- and exonucleolytic activity.

The FEN-1 enzymes are functionally related to several smaller bacteriophage 5'→3' exonucleases such as T5.5' exonuclease and T4 RNase H as well as to the larger eukaryotic nucleotide excision repair enzymes such as XPG, which also acts in the transcription-coupled repair of oxidative base damage. In eubacteria such as *Escherichia coli* and *Thermus aquaticus*, Okazaki processing is provided by the PolI 5'→3' exonuclease domain. These bacterial and phage enzymes share two areas of limited sequence homology with FEN-1, which are termed the N (N-terminal) and I (intermediate) regions, with the residue similarities concentrated around seven conserved acidic residues. Based on crystal structures of T4 Rnase H and T5 exonuclease as well as mutagenesis data, it has been proposed that these residues bind to two $Mg^{2+}$ ions that are required for affecting DNA hydrolysis; however, the role each metal plays in the catalytic cycle, which is subtly different for each enzyme, is not well understood (Reviewed in Hosfield et al., 1998b, supra).

fen-1 genes encoding FEN-1 enzymes useful in the invention include murine fen-1, human fen-1, rat fen-1, *Xenopus laevis* fen-1, and fen-1 genes derived from four archaebacteria *Archaeglobus fulgidus, Methanococcus jannaschii, Pyrococcus furiosus* and *Pyrococcus horikoshii*. cDNA clones encoding FEN-1 enzymes have been isolated from human (GenBank Accession Nos.: NM_004111 and L37374), mouse (GenBank Accession No.: L26320), rat (GenBank Accession No.: AA819793), *Xenopus laevis* (GenBank Accession Nos.: U68141 and U64563), and *P. furiosus* (GenBank Accession No.: AF013497). The complete nucleotide sequence for *P. horikoshii* flap endonuclease has also been determined (GenBank Accession No.: AB005215). The FEN-1 family also includes the *Saccharomyces cerevisiae*. RAD27 gene (GenBank Accession No.: Z28113 Y13137) and the *Saccharomyces pombe* RAD2 gene (GenBank Accession No.: X77041). The archaeal genome of *Methanobacterium thermautotrophiculum* has also been sequenced. Although the sequence similarity between FEN-1 and prokaryotic and viral 5'→3' exonucleases is low, FEN-1s within the eukaryotic kingdom are highly conserved at the amino acid level, with the human and *S. cerevisiae* proteins being 60% identical and 78% similar. The three archaebacterial FEN-1 proteins are also, highly homologous to the eukaryotic FEN-1 enzymes (Reviewed in Matsui et al., 1999, *J. Biol. Chem.*, 274:18297, Hosfield et al., 1998b, *J. Biol. Chem.*, 273:27154 and Lieber, 1997, *BioEssays*, 19:233).

The sequence similarities in the two conserved nuclease domains (N-terminal or N and intermediate or I domains) between human and other FEN-1 family members are 92% (murine), 79% (*S. cerevisiae*), 77% (*S. pombe*), 72% (*A. fulgidus*), 76% (*M. jannaschii*), and 74% (*P. furiosus*).

FEN-1 specifically recognizes the backbone of a 5' single-stranded flap strand and migrates down this flap arm to the cleavage site located at the junction between the two strands of duplex DNA and the single-stranded arm. If the strand upstream of the flap (sometimes called the flap adjacent strand or primer strand) is removed, the resulting structure is termed a pseudo-Y (see FIG. 1). This structure is cleaved by FEN-1, but at 20- to 100-fold lower efficiency. FEN-1 does not cleave 3' single-stranded flaps. However, FEN-1 acting as an exonuclease will hydrolyze dsDNA substrates containing a gap or nick (Reviewed in Hosfield et al., 1998a, supra, Hosfield et al., 1999b, supra and Lieber 1997, supra). Exonucleolytically, FEN-1 acts at a nick and, with lower efficiency, at a gap or a recessed 5' end on dsDNA. At gapped structures, the efficiency of FEN-1 binding and cutting decreases with increasing gap size up to approximately five nucleotides and then stabilizes at a level of cleavage that is equivalent to activity on a recessed 5' end within dsDNA. Blunt dsDNA, recessed 3' ends and ssDNA are not cleaved (Reviewed in Lieber 1997, supra).

FEN nucleases that are useful according to the invention have been isolated from a variety of organisms including human (GenBank Accession Nos.: NM_004111 and L37374), mouse (GenBank Accession No.: L26320), rat (GenBank Accession No.: AA819793), yeast (GenBank Accession No.: Z28113 Y13137 and GenBank Accession No.: X77041) and *xenopus laevis* (GenBank Accession Nos.: U68141 and U64563). Such enzymes can be cloned and overexpressed using conventional techniques well known in the art.

A FEN nuclease according to the invention is preferably thermrostable. Thermostable FEN nucleases have been isolated and characterized from a variety of thermostable organisms including four archeaebacteria. The cDNA sequence (GenBank Accession No.: AF013497) and the amino acid sequence (Hosfield et al., 1998a, supra and Hosfield et al., 1998b) for *P. furiosus* flap endonuclease have been determined. The complete nucleotide sequence (GenBank Accession No.: AB005215) and the amino acid sequence (Matsui et al., supra) for *P. horikoshii* flap endonuclease have also been determined. The amino acid sequence for *M. jannaschii* (Hosfield et al., 1998b and Matsui et al., 1999 supra) and *A. fulgidus* (Hosfield et al., 1998b) flap endonuclease have also been determined.

Thermostable FEN-1 enzymes can be cloned and overexpressed using techniques well known in the art and described in Hosfield et al., 1998a, supra, Hosfield et al., 1998b, Kaiser et al., 1999, J. Biol. Chem., 274: 21387 and Matusi et al., supra and herein in Example 2 entitled "Cloning Pfu FEN-1".

The endonuclease activity of a FEN enzyme can be measured by a variety of methods including the following.

A. FEN Endonuclease Activity Assay

Figure 2:
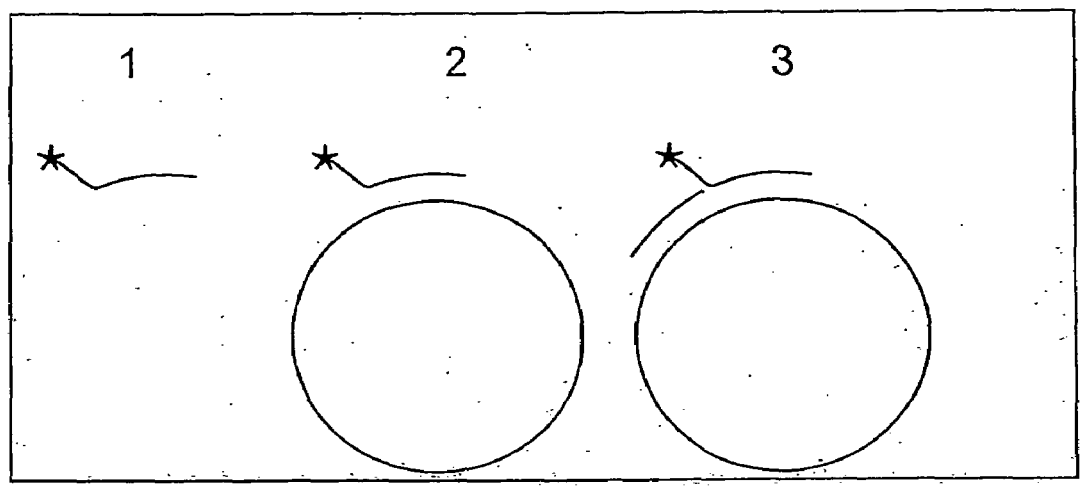
FIG. 2 demonstrates three templates (labeled 1, 2, and 3) that may be used to detect FEN nuclease activity.

1. Templates (for example as shown in FIG. 2) are used to evaluate the activity of a FEN nuclease according to the invention.

Template 1 is a 5' $^{33}$P labeled oligonucleotide (Heltest4) with the following sequence: 5'AAAATAAATAAAAAAAAT ACTGTTGGGAAGGGCGATCGGTGCG 3'. The underlined section of Heltest4 represents the region complementary to M13mp18+. The cleavage product is an 18 nucleotide fragment with the sequence AAAATAAATAAAAAAAAT.

Heltest4 binds to M13 to produce a complementary double stranded domain as well as a non-complementary 5' overhang. This duplex forms template 2 (FIG. 2) which is also used for helicase assays. Template 3 (FIG. 2) has an additional primer (FENAS) bound to M13 and is directly adjacent to Heltest 4. The sequence of FENAS is:

5'CCATTCGCCATTCAGGCTGCGCA 3'. In the presence of template 3, FEN binds the free 5' terminus of Heltest4, migrates to the junction and cleaves Heltest4 to produce an 18 nucleotide fragment. Templates 1 and 2 serve as controls, although template 2 can also serve as a template.

Templates are prepared as described below:

|  | Template 1 | Template 2 | Template 3 |
|---|---|---|---|
| Heltest4 | 14 µl | 14 µl | 14 µl |
| M13 | ** | 14 µl | 14 µl |
| FENAS | ** | ** | 14 µl |

-continued

|  | Template 1 | Template 2 | Template 3 |
|---|---|---|---|
| H$_2$O | 28 µl | 14 µl | ** |
| 10× Pfu Buff. | 4.6 µl | 4.6 µl | 4.6 µl |

10× Pfu buffer is available from Stratagene (Catalog #200536). According to the method of the invention, 10× Pfu buffer is diluted such that a reaction is carried out in the presence of 1× buffer.

M13 is M13mp18+ strand and is at a concentration of 200 ng/µL, $^{33}$P labeled Heltest4 is at an approximate concentration of 0.7 ng/µl, and FENAS is at a concentration of 4.3 ng/µl. Based on these concentrations, the Heltest4 and M13 are at approximately equal molar amounts (5× 10$^{-14}$) and FENAS is present in an approximately 10× molar excess (6× 10$^{-13}$).

The template mixture is heated at 95° C. for five minutes, cooled to room temperature for 45 minutes and stored at 4° C. overnight.

2 µl of FEN-1 or, as a control, H$_2$O are mixed with the three templates as follows:

| | |
|---|---|
| 3 µl | template |
| 0.7 µl | 10× cloned Pfu buffer |
| 0.56 µl | 100 mM MgCl$_2$ |
| 2.00 µl | enzyme or H$_2$O |
| 0.74 µl | H$_2$0 |
| 7.00 µl | total volume |

The reactions are allowed to proceed for 30 minutes at 50° C. and stopped by the addition of 2 µl formamide "Sequencing Stop" solution to each sample. Samples are heated at 95° C. for five minutes and loaded on a 6% acrylamide, 7M urea CastAway (Stratagene) gel.

Alternatively, FEN activity can be analyzed in the following buffer wherein a one hour incubation time is utilized.

10× FEN Buffer
500 mM Tris-HCl pH 8.0
100 mM MgCl$_2$

The reaction mixture below is mixed with 2 µl of FEN or, as a control, 2 µl of H$_2$O.

| | |
|---|---|
| 3 µl | template |
| 0.7 µl | 10× FEN buffer |
| 2.00 µl | enzyme or H$_2$O |
| 1.3 µl | H$_2$O |
| 7.00 µl | total volume |

Samples are incubated for one hour at 50° C. in a Robocyler 96 hot top thermal cycler. Following the addition of 2 µl of Sequencing Stop dye solution, samples are heated at 99° C. for five minutes. Samples are loaded on an eleven-inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix (15% methanol, 5% acetic acid) and then for 10 minutes in water. The gel is placed on Whatmann 3 mm paper, covered with plastic wrap and dried for 2 hours in a heated vacuum gel dryer. The gel is exposed overnight to X-ray film.

2. FEN endonuclease activity can also be measured according to the method of Kaiser et al., supra). Briefly, reactions are carried out in a 10 μl volume containing 10 mM MOPS, pH 7.5, 0.05% Tween 20, 0.05% Nonidet P-40, 10 μg/ml tRNA, and 200 mM KCl for TaqPol and TthPol or 50 mM KCl for all other enzymes. Reaction conditions can be varied depending on the cleavage structure being analyzed. Substrates (2 μM) and varying amounts of enzyme are mixed with the indicated (above) reaction buffer and overlaid with Chill-out (MJ Research) liquid wax. Substrates are heat denatured at 90° C. for 20 s and cooled to 50° C., then reactions are started by addition of $MgCl_2$ or $MnCl_2$ and incubated at 50° C. for the specified length of time. Reactions are stopped by the addition of 10 μl of 95% formamide containing 10 mM EDTA and 0.02% methyl violet (Sigma). Samples are heated to 90° C. for 1 min immediately before electrophoresis on a 20% denaturing acrylamide gel (19:1 cross-linked), with 7M urea, and in a buffer of 45 mM Tris borate, pH 8.3, 1.4 mM EDTA. Unless otherwise indicated, 1 μl of each stopped reaction is loaded per lane. Gels are scanned on an FMBIO-100 fluorescent gel scanner (Hitachi) using a 505-nm filter. The fraction of cleaved product is determined from intensities of bands corresponding to uncut and cut substrate with FMBIO Analysis software (version 6.0, Hitachi). The fraction of cut product should not exceed 20% to ensure that measurements approximate initial cleavage rates. The cleavage rate is defined as the concentration of cut product divided by the enzyme concentration and the time of the reaction (in minutes). For each enzyme three data points are used to determine the rate and experimental error.

3. FEN endonuclease activity can also be measured according to the method of Hosfield et al., 1998a, supra. Briefly, in a final volume of 13 μl, varying amounts of FEN and 1.54 pmol of labeled cleavage substrate are incubated at different temperatures for 30 min before the reaction is quenched with an equal volume of stop solution (10 mM EDTA, 95% deionized formamide, and 0.008% bromophenol blue and xylene cyanol). Samples are electrophoresed through denaturing 15% polyacrylamide gels, and the relative amounts of starting material and product are quantitated using the IPLabGel system (Stratagene) running MacBAS image analysis software. Most reactions are performed in standard assay buffer (10 mM Tris-HCl (pH 8.0), 10 mM $MgCl_2$, and 50 μg/ml bovine serum albumin); however, in a series of experiments the effect of different divalent metals and pH levels are studied by varying the standard buffer. For divalent metals, $MgCl_2$ is omitted, and different metal ions are used at a final concentration of 10 mM. To study the influence of pH, buffers containing different amounts of Tris-HCl, glycine, and sodium acetate are used at a final concentration of 10 mM to obtain a wide range of pH levels at 25° C.

4. FEN endonuclease activity can also be measured according to the method of Matusi et al., 1999, supra. Briefly, the enzyme are performed in a 15-μl reaction mixture containing 50 mM Tris-HCl (pH 7.4), 1.5 mM $MgCl_2$, 0.5 mM β-mercaptoethanol, 100 μg/ml bovine serum albumin, and 0.6 pmol of a labeled cleavage structure. After incubation for 30 min at 60° C., the reaction is terminated by adding 15 μl of 95% formamide containing 10 mM EDTA and 1 mg/ml bromophenol blue. The samples are heated at 95° C. for 10 min, loaded onto a 15% polyacrylamide gel (35 cm×42.5 cm) containing 7M urea and 10×TBE (89 mM Tris-HCl, 89 mM boric acid, 2 mM EDTA (pH 8.0)), and then electrophoresed for 2 h at 2000 V. Reaction products are visualized and quantified using a PhosphorImager (Bio-Rad). Size marker, oligonucleotides are 5' end-labeled with [γ-$^{32}$P] ATP and T4 polynucleotide kinase.

To determine the optimum pH, the reaction is performed in an assay mixture (15 μl) containing 1.5 mM $MgCl_2$, 0.5 mM β-mercaptoethanol, 100 μg/ml bovine serum albumin, and 0.6 pmol of 5' end-labeled cleavage structure in 50 mM of one of the following buffers at 60° C. for 30 min. Three different 50 mM buffers are used to obtain a wide pH range as follows: sodium acetate buffer (pH 4.0-5.5), phosphate buffer (pH 5.5-8.0), and borate buffer (pH 8.0-9.4).

B. FEN Exonuclease Activity Assay

The exonuclease activity of a FEN nuclease according to the invention can be measured by the method of measuring FEN-1 endonuclease activity described in Matsui et al., 1999, supra and summarized above.

Alternatively, the exonuclease activity of a FEN enzyme can be analyzed by the method described in Hosfield et al., 1998b, supra. Briefly, exonuclease activities are assayed using a nicked substrate of FEN under conditions identical to those described for the endonuclease assays (described above).

The precise positions of DNA cleavage in both the exonuclease and endonuclease experiments can be obtained by partial digestion of a 5' $^{32}$P-labeled template strand using the 3'-5' exonuclease activity of Klenow fragment.

Figure 3:
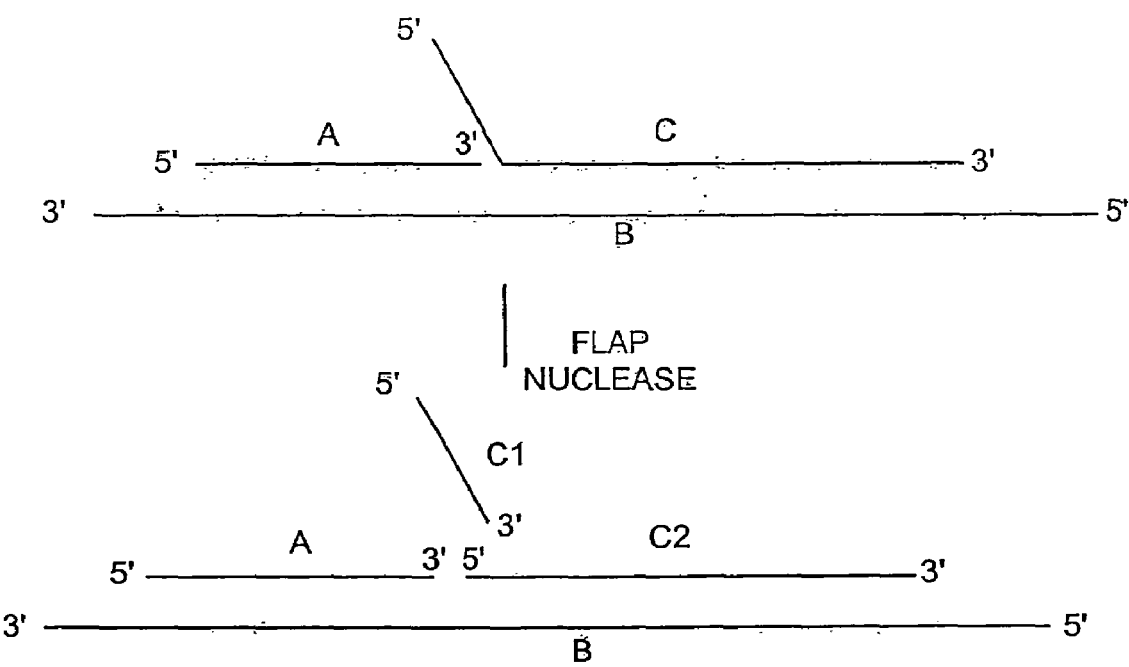
FIG. 3 is a diagram illustrating a synthesis and cleavage reaction to generate a signal according to the invention.

A cleavage structure according to the invention comprises a partially displaced 5' end of an oligonucleotide annealed to a target nucleic acid sequence. Another cleavage structure according to the invention comprises a target nucleic acid sequence (for example B in FIG. 3), an upstream oligonucleotide that is complementary to the target sequence (for example A in FIG. 3), and a downstream oligonucleotide that is complementary to the target sequence (for example C in FIG. 3). A cleavage structure according to the invention can be formed by overlap between the upstream oligonucleotide and the downstream probe, or by extension of the upstream oligonucleotide by the synthetic activity of a nucleic acid polymerase, and subsequent partial displacement of the 5' end of the downstream oligonucleotide. A cleavage structure of this type is formed according to the method described in the section entitled "Cleavage Structure".

Alternatively, a cleavage structure according to the invention is formed by annealing a target nucleic acid sequence to an oligonucleotide wherein the oligonucleotide comprises a complementary region that anneals to the target nucleic acid sequence, and a non-complementary region that does not anneal to the target nucleic acid sequence and forms a 5' flap. According to this embodiment, a cleavage structure comprises a 5' flap formed by a non-complementary region of the oligonucleotide.

A cleavage structure according to the invention also comprises an overlapping flap wherein the 3' end of an upstream oligonucleotide capable of annealing to a target nucleic acid sequence (for example A in FIG. 3) is complementary to 1 (or more) base pair of the downstream oligonucleotide (for example C in FIG. 3) that is annealed to a target nucleic acid sequence and wherein the 1 (or more) base pair overlap is directly downstream of the point of extension of the single stranded flap and is formed according to method described in the section entitled "Cleavage Structure".

II. Nucleic Acid Polymerases

The invention provides for nucleic acid polymerases. Preferably, the nucleic acid polymerase according to the invention is thermostable.

Known DNA polymerases include, for example, *E. coli* DNA polymerase I, *Thermus thermophilus* (Tth) DNA polymerase, *Bacillus stearothermophilus* DNA polymerase,

*Thermococcus litoralis* DNA polymerase, *Thermus aquaticus* (Taq) DNA polymerase and *Pyrococcus furiosus* (Pfu) DNA polymerase.

Nucleic acid polymerases substantially lacking 5' to 3' exonuclease activity useful according to the invention include but are not limited to Klenow and Klenow exo-, and T7 DNA polymerase (Sequenase).

Thermostable nucleic acid polymerases substantially lacking 5' to 3' exonuclease activity useful according to the invention include but are not limited to Pfu, exo-Pfu (a mutant form of Pfu that lacks 3' to 5' exonuclease activity), the Stoffel fragment of Taq, N-truncated Bst, N-truncated Bca, Genta, JdF3 exo-, Vent, Vent exo- (a mutant form of Vent that lacks 3' to 5' exonuclease activity), Deep Vent, Deep Vent exo- (a mutant form of Deep Vent that lacks 3' to 5' exonuclease activity), U1Tma, and ThermoSequenase.

Nucleic acid polymerases useful according to the invention include both native polymerases as well as polymerase mutants, which lack 5' to 3' exonuclease activity. Nucleic acid polymerases useful according to the invention can possess different degrees of thermostability. Preferably, a nucleic acid polymerase according to the invention exhibits strand displacement activity at the temperature at which it can extend a nucleic acid primer. In a preferred embodiment of the invention, a nucleic acid polymerase lacks both 5' to 3' and 3' to 5' exonuclease activity.

Additional nucleic acid polymerases substantially lacking 5' to 3' exonuclease activity with different degrees of thermostability useful according to the invention are listed below.

A. Bacteriophage DNA Polymerases (Useful for 37° C. Assays):

Bacteriophage DNA polymerases are devoid of 5' to 3' exonuclease activity, as this activity is encoded by a separate polypeptide. Examples of suitable DNA polymerases are T4, T7, and φ29 DNA polymerase. The enzymes available commercially are: T4 (available from many sources e.g., Epicentre) and T7 (available from many sources, e.g. Epicentre for unmodified and USB for 3' to 5' exo T7 "Sequenase" DNA polymerase).

B. Archaeal DNA Polymerases:

There are 2 different classes of DNA polymerases which have been identified in archaea: 1. Family B/pol α type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol α or pol II) can be derived from archaea with optimal growth temperatures that are similar to the desired assay temperatures. Examples of suitable archaea include, but are not limited to:

1. Thermolabile (useful for 37° C. assays)—e.g., *Methanococcus voltae*

2. Thermostable (useful for non-PCR assays)—e.g., *Sulfolobus solfataricus, Sulfolobus acidocaldarium, Methanococcus jannaschi, Thermoplasma acidophilum*. It is estimated that suitable archaea exhibit maximal growth temperatures of ≦80-85° C. or optimal growth temperatures of ≦70-80° C.

3. Thermostable (useful for PCR assays)—e.g., *Pyrococcus* species (*friosus*, species GB-D, species strain KOD1, *woesii, abysii, horikoshii*), *Thermococcus* species (*litoralis*, species 9° North-7, species JDF-3, *gorgonarius*), *Pyrodictium occultum*, and *Archaeoglobus fulgidus*. It is estimated that suitable archaea would exhibit maximal growth temperatures of ≧80-85° C. or optimal growth temperatures of ≧70-80° C. Appropriate PCR enzymes from the archaeal pol α DNA polymerase group are commercially available, including KOD (Toyobo), Pfx (Life Technologies, Inc.), Vent (New England BioLabs), Deep Vent (New England BioLabs), and Pwo (Boehringer-Mannheim).

Additional archaea related to those listed above are described in the following references: *Archaea: A Laboratory Manual* (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases.

There are a variety of commercially available Pol I DNA polymerases, some of which have been modified to reduce or abolish 5' to 3' exonuclease activity. Methods used to eliminate 5' to 3' exonuclease activity of pol I DNA polymerases include:

mutagenesis (as described in Xu et al., 1997, *J. Mol. Biol.*, 268:284 and Kim et al., 1997, *Mol. Cells*, 7:468).

N-truncation by proteolytic digestion (as described in Klenow et al., 1971, *Eur. J. Biochem.*, 22: 371), or N-truncation by cloning and expressing as C-terminal fragments (as described in Lawyer et al., 1993, *PCR Methods Appl.*, 2:275).

As for archaeal sources, the assay-temperature requirements determine which eubacteria should be used as a source of a DNA polymerase useful according to the invention (e.g., mesophiles, thermophiles, hyperthermophiles).

1. Mesophilic/thermolabile (Useful for 37° C. Assays)

i. DNA polymerases naturally substantially lacking 5' to 3' exonuclease activity: pol II or the pol III catalytic subunit from mesophilic eubacteria, such as *Escherichia coli, Streptococcus pneumoniae, Haemophilus influenza, Mycobacterium* species (*tuberculosis, leprae*)

ii. DNA polymerase mutants substantially lacking 5' to 3' exonuclease activity: Pol I DNA polymerases for N-truncation or mutagenesis can be isolated from the mesophilic eubacteria listed above (Ci). A commercially-available eubacterial DNA polymerase pol I fragment is the Klenow fragment (N-truncated *E. coli* pol I; Stratagene).

2. Thermostable (Useful for non PCR assays)

i. DNA polymerases naturally substantially lacking 5' to 3' exonuclease activity: Pol II or the pol III catalytic subunit from thermophilic eubacteria, such as *Bacillus* species (e.g., *stearothermophilus, caldotenax, caldovelox*)

ii. DNA polymerase mutants substantially lacking 5' to 3' exonuclease activity: Suitable pol I DNA polymerases for N-truncation or mutagenesis can be isolated from thermophilic eubacteria such as the *Bacillus* species listed above. Thermostable N-truncated fragments of *B. stearothermophilus* DNA polymerase pol I are commercially available and sold under the trade names Bst DNA polymerase I large fragment (Bio-Rad and Isotherm DNA polymerase (Epicentre)). A C-terminal fragment of *Bacillus caldotenax* pol I is available from Panvera (sold under the tradename Ladderman).

3. Thermostable (Useful for PCR assays)

i. DNA polymerases naturally substantially lacking 5' to 3' exonuclease activity: Pol II or pol III catalytic subunit from *Thermus* species (*aquaticus, thermophilus, flavus, ruber, caldophilus, filiformis, brokianus*) or from *Thermotoga maritima*. The catalytic pol III subunits from *Thermus thermophilus* and *Thermus aquaticus* are described in Yi-Ping et al., 1999, J. Mol. Evol., 48:756 and McHenry et al., 1997, J. Mol. Biol., 272:178.

ii. DNA polymerase mutants substantially lacking 5' to 3' exonuclease activity: Suitable pol I DNA polymerases for N-truncation or mutagenesis can be isolated from a variety of thermophilic eubacteria, including *Thermus* species and *Thermotoga maritima* (see above). Thermostable fragments of *Thermus aquaticus* DNA polymerase pol I (Taq) are commercially available and sold under the trade names KlenTaq1 (Ab Peptides), Stoffel fragment (Perkin-Elmer), and ThermoSequenase (Amersham). In addition to C-terminal fragments, 5' to 3' exonuclease Taq mutants are also commercially available, such as TaqFS (Hoffman-LaRoche). In addition to 5'-3' exonuclease versions of Taq, an N-truncated version of *Thermotoga maritima* DNA polymerase I is also commercially available (tradename UlTma, Perkin-Elmer).

Additional eubacteria related to those listed above are described in *Thermophilic Bacteria* (Kristjansson, J. K., ed.) CRC Press, Inc., Boca Raton, Fla., 1992.

D. Eukaryotic 5' to 3' Exonuclease DNA Polymerases (Useful for 37° C. Assays)

There are several DNA polymerases that have been identified in eukaryotes, including DNA pol α (replication/repair), δ (replication), ε (replication), β (repair) and γ (mitochondrial replication). Eukaryotic DNA polymerases are devoid of 5' to 3' exonuclease activity, as this activity is encoded by a separate polypeptide (e.g., mammalian FEN-1 or yeast RAD2). Suitable thermolabile DNA polymerases may be isolated from a variety of eukaryotes (including but not limited to yeast, mammalian cells, insect cells, *Drosophila*) and eukaryotic viruses (e.g., EBV, adenovirus).

It is possible that DNA polymerase mutants lacking 3'-5' exonuclease (proofreading) activity, in addition to lacking 5' to 3' exonuclease activity, could exhibit improved performance in FEN-based detection strategies. For example, reducing or abolishing inherent 3' to 5' exonuclease activity may lower background signals by diminishing non-specific exonucleolytic degradation of labeled probes. Three 3' to 5' exonuclease motifs have been identified, and mutations in these regions have been shown to abolish 3' to 5' exonuclease activity in Klenow, φ29, T4; T7, and Vent DNA polymerases, yeast Pol α, Pol β, and Pol γ, and *Bacillus subtilis* Pol III (reviewed in Derbeyshire et al., 1995, Methods. Enzymol. 262:363). Methods for preparing additional DNA polymerase mutants, with reduced or abolished 3' to 5' exonuclease activity, are well known in the art.

Commercially-available enzymes that lack both 5' to 3' and 3' to 5' exonuclease activities include Sequenase (exo⁻ T7; USB), Pfu exo⁻ (Stratagene), exo⁻ Vent (New England BioLabs), exo⁻ Deep Vent (New England BioLabs), exo⁻ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche).

If polymerases other than Pfu are used, buffers and extension temperatures are selected to allow for optimal activity by the particular polymerase useful according to the invention. Buffers and extension temperatures useful for polymerases according to the invention are know in the art and can also be determined from the Vendor's specifications.

III. Nucleic Acids

A. Nucleic Acid Sequences Useful in the Invention

The invention provides for methods of detecting or measuring a target nucleic acid sequence; and also utilizes oligonucleotides, primers and probes for forming a cleavage structure according to the invention and primers for amplifying a template nucleic acid sequence. As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

The complement of a nucleic acid sequence as used herein refers to an oligonucleotide which, when aligned with the nucleic acid sequence such that the 5' end of one sequence is paired with the 3' end of the other, is in "antiparallel association."

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its synthetic origin or manipulation: (1) is not associated with all or a portion of the polynucleotide with which it is associated in nature; and/or (2) is linked to a polynucleotide other than that to which it is linked in nature.

Oligonucleotides, according to the present invention, additionally comprise nucleic acid sequences which function as probes and can have secondary structure such as hairpins and stem-loops. Such oligonucleotide probes include, but are not limited to the molecular beacons, safteypins, scorpions, and sunrise/amplifluor probes described herein.

Because mononucleotides are reacted to make oligonucleotides in a manner such that the 5' phosphate of one mononucleotide pentose ring is attached to the 3' oxygen of its neighbor in one direction via a phosphodiester linkage, an end of oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the base pairs have disassociated.

B. Primers and Probes Useful According to the Invention

The invention provides for oligonucleotide primers and probes useful for detecting or measuring a nucleic acid, for amplifying a template nucleic acid sequence, and for forming a cleavage structure according to the invention.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleotide triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

Oligonucleotide primers useful according to the invention are single-stranded DNA or RNA molecules that are hybridizable to a template nucleic acid sequence and prime enzymatic synthesis of a second nucleic acid strand. The primer is complementary to a portion of a target molecule present in a pool of nucleic acid molecules. It is contemplated that oligonucleotide primers according to the invention are prepared by synthetic methods, either chemical or enzymatic. Alternatively, such a molecule or a fragment thereof is naturally-occurring, and is isolated from its natural source or purchased from a commercial supplier. Oligonucleotide primers and probes are 5 to 100 nucleotides in length, ideally from 17 to 40 nucleotides, although primers and probes of different length are of use. Primers for amplification are preferably about 17-25 nucleotides. Primers for the production of a cleavage structure according to the invention are preferably about 17-45 nucleotides. Primers useful according to the invention are also designed to have a particular melting temperature (Tm) by the method of melting temperature estimation. Commercial programs, including Oligo™, Primer Design and programs available on the internet, including Primer3 and Oligo Calculator can be used to calculate a Tm of a nucleic acid sequence useful according to the invention. Preferably, the Tm of an amplification primer useful according to the invention, as calculated for example by Oligo Calculator, is preferably between about 45 and 65° C. and more preferably between about 50 and 60° C. Preferably, the Tm of a probe useful according to the invention is 7° C. higher than the Tm of the corresponding amplification primers.

As used herein, "probe" refers to a labeled oligonucleotide that can be a primer, useful for preparation of a cleavage structure according to the invention. Pairs of single-stranded DNA primers can be annealed to sequences within a target nucleic acid sequence or can be used to prime amplifying DNA synthesis of a target nucleic acid sequence.

Typically, selective hybridization occurs when two nucleic acid sequences are substantially complementary (at least about 65% complementary over a stretch of at least 14 to 25 nucleotides, preferably at least about 7.5%, more preferably at least about 90% complementary). See Kanehisa, M., 1984, Nucleic Acids Res. 12: 203, incorporated herein by reference. As a result, it is expected that a certain degree of mismatch at the priming site is tolerated. Such mismatch may be small, such as a mono-, di- or tri-nucleotide. Alternatively, a region of mismatch may encompass loops, which are defined as regions in which there exists a mismatch in an uninterrupted series of four or more nucleotides.

Numerous factors influence the efficiency and selectivity of hybridization of the primer to a second nucleic acid molecule. These factors, which include primer length, nucleotide sequence and/or composition, hybridization temperature, buffer composition and potential for steric hindrance in the region to which the primer is required to hybridize, will be considered when designing oligonucleotide primers according to the invention.

A positive correlation exists between primer length and both the efficiency and accuracy with which a primer will anneal to a target sequence. In particular, longer sequences have a higher melting temperature ($T_M$) than do shorter ones, and are less likely to be repeated within a given target sequence, thereby minimizing promiscuous hybridization. Primer sequences with a high G-C content or that comprise palindromic sequences tend to self-hybridize, as do their intended target sites, since unimolecular, rather than bimolecular, hybridization kinetics are generally favored in solution. However, it is also important to design a primer that contains sufficient numbers of G-C nucleotide pairings since each G-C pair is bound by three hydrogen bonds, rather than the two that are found when A and T bases pair to bind the target sequence, and therefore forms a tighter, stronger bond. Hybridization temperature varies inversely with primer annealing efficiency, as does the concentration of organic solvents, e.g. formamide, that might be included in a priming reaction or hybridization mixture, while increases in salt concentration facilitate binding. Under stringent annealing conditions, longer hybridization probes, or synthesis primers, hybridize more efficiently than do shorter ones, which are sufficient under more permissive conditions. Stringent hybridization conditions typically include salt concentrations of less than about 1 M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of a single factor.

Oligonucleotide primers can be designed with these considerations in mind and synthesized according to the following methods.

1. Oligonucleotide Primer Design Strategy

The design of a particular oligonucleotide primer for the purpose of sequencing, PCR or for the preparation of a cleavage structure according to the invention, involves selecting a sequence that is capable of recognizing the target sequence, but has a minimal predicted secondary structure. The oligonucleotide sequence binds only to a single site in the target nucleic acid sequence. Furthermore, the Tm of the oligonucleotide is optimized by analysis of the length and GC content of the oligonucleotide. Furthermore, when designing a PCR primer useful for the amplification of genomic DNA, the selected primer sequence does not demonstrate significant matches to sequences in the GenBank database (or other available databases).

The design of a primer is facilitated by the use of readily available computer programs, developed to assist in the evaluation of the several parameters described above and the optimization of primer sequences. Examples of such programs are "PrimerSelect" of the DNAStar™ software package (DNAStar, Inc.; Madison, Wis.), OLIGO 4.0 (National Biosciences, Inc.), PRIMER, Oligonucleotide Selection Program, PGEN and Amplify (described in Ausubel et al., 1995, Short Protocols in Molecular Biology, 3rd Edition, John Wiley & Sons). In one embodiment, primers are designed with sequences that serve as targets for other primers to produce a PCR product that has known sequences on the ends which serve as targets for further amplification (e.g. to sequence the PCR product). If many different target nucleic acid sequences are amplified with specific primers that share a common 'tail' sequence', the PCR products from these distinct genes can subsequently be sequenced with a single set of primers. Alternatively, in order to facilitate subsequent cloning of amplified sequences, primers are designed with restriction enzyme site sequences appended to their 5' ends. Thus, all nucleotides of the primers are derived from a target nucleic acid sequence or sequences adjacent to a target nucleic acid sequence, except for the few nucleotides necessary to form a restriction enzyme site. Such enzymes and sites are well known in the art. If the genomic sequence of a target nucleic acid sequence and the sequence of the open reading frame of a target nucleic acid sequence are known, design of particular primers is well within the skill of the art.

It is well known by those with skill in the art that oligonucleotides can be synthesized with certain chemical and/or capture moieties, such that they can be coupled to solid supports. Suitable capture moieties include, but are not limited to, biotin, a hapten, a protein, a nucleotide sequence, or a chemically reactive moiety. Such oligonucleotides may either be used first in solution, and then captured onto a solid support, or first attached to a solid support and then used in a detection reaction. An example of the latter would be to couple a downstream probe molecule to a solid support, such that the 5' end of the downstream probe molecule comprised a fluorescent quencher. The same downstream probe molecule would also comprise a fluorophore in a location such that a FEN nuclease cleavage would physically separate the quencher from the fluorophore. For example, the target nucleic acid could hybridize with the solid-phase downstream probe oligonucleotide, and a liquid phase upstream primer could also hybridize with the target molecule, such that a FEN cleavage reaction occurs on the solid support and liberates the 5' quencher moiety from the complex. This would cause the solid support-bound fluorophore to be detectable, and thus reveal the presence of a cleavage event upon a suitably labeled or identified solid support. Different downstream probe molecules could be bound to different locations on an array. The location on the array would identify the probe molecule, and indicate the presence of the template to which the probe molecule can hybridize.

2. Synthesis

The primers themselves are synthesized using techniques that are also well known in the art. Methods for preparing oligonucleotides of specific sequence are known in the art, and include, for example, cloning and restriction digest analysis of appropriate sequences and direct chemical synthesis. Once designed, oligonucleotides are prepared by a suitable chemical synthesis method, including, for example, the phosphotriester method described by Narang et al., 1979, Methods in Enzymology, 68:90, the phosphodiester method disclosed by Brown et al., 1979, Methods in Enzymology; 68:109, the diethylphosphoramidate method disclosed in Beaucage et al., 1981, Tetrahedron Letters, 22:1859, and the solid support method disclosed in U.S. Pat. No. 4,458,066, or by other chemical methods using either a commercial automated oligonucleotide synthesizer (which is commercially available) or VLSIPS™ technology.

C. Probes

The invention provides for probes useful for forming a labeled cleavage structure as defined herein. Methods of preparing a labeled cleavage structure according to the invention are provided in the section entitled "Cleavage Structure" below.

As used herein, the term "probe" refers to a labeled oligonucleotide which forms a duplex structure with a sequence in the target nucleic acid, due to complementarity of at least one sequence in the probe with a sequence in the target region. Probe lengths useful in the invention are preferably 10-50 nucleotides, and more preferably 16-25 nucleotides. The probe, preferably, does not contain a sequence complementary to sequence(s) used in the primer extension(s). Generally the 3' terminus of the probe will be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as dideoxynucleotide.

Additionally, according to the present invention, a probe can be an oligonucleotide with secondary structure such as a hairpin or a stem-loop, and includes, but is not limited to molecular beacons, safety pins, scorpions, and sunrise/amplifluor probes.

Molecular beacon probes comprise a hairpin, or stem-loop structure which possesses a pair of interactive signal generating labeled moieties (e.g., a fluorophore and a quencher) effectively positioned to quench the generation of a detectable signal. The loop comprises a region that is complementary to a target nucleic acid. The loop is flanked by 5' and 3' regions ("arms") that reversibly interact with one another by means of complementary nucleic acid sequences when the region of the probe that is complementary to a nucleic acid target sequence is not bound to the target nucleic acid. Alternatively, the loop is flanked by 5' and 3' regions ("arms") that reversibly interact with one another by means of attached members of an affinity pair to form a secondary structure when the region of the probe that is complementary to a nucleic acid target sequence is not bound to the target nucleic acid. As used herein, "arms" refers to regions of a probe that reversibly interact with one another by means of complementary nucleic acid sequences when the region of the probe that is complementary to a nucleic acid target sequence is not bound to the target nucleic acid or regions of a probe that reversibly interact with one another by means of attached members of an affinity pair to form a secondary structure when the region of the probe that is complementary to a nucleic acid target sequence is not bound to the target nucleic acid. When a molecular beacon probe is not hybridized to target, the arms hybridize with one another to form a stem hybrid, which is sometimes referred to as the "stem duplex". This is the closed conformation. When a molecular beacon probe hybridizes to its target the "arms" of the probe are separated. This is the open conformation. In the open conformation an arm may also hybridize to the target. Such probes may be free in solution, or they may be tethered to a solid surface. When the arms are hybridized (e.g., form a stem) the quencher is very close to the fluorophore and effectively quenches or suppresses its fluorescence, rendering the probe dark. Such probes are described in U.S. Pat. Nos. 5,925,517 and 6,037,130.

As used herein, a molecular beacon probe that is an "allele-discriminating" probe will not hybridize sufficiently to a target-like nucleic acid sequence that contains one or more internally located nucleotide mismatches as compared to the target nucleic acid complementary sequence and thus will not convert conformationally to an open conformation in the presence of a target like nucleic acid sequence, and under conditions that would support hybridization of the allele discriminating probe to a target nucleic acid sequence. In other embodiments a molecular beacon probe will hybridize sufficiently to a target-like nucleic acid sequence that contains one or more internally located nucleotide mismatches as compared to the target nucleic acid complementary sequence and will convert conformationally to an open conformation in the presence of a target-like nucleic acid sequence, and under conditions that would support hybridization of the allele discriminating probe to a target nucleic acid sequence. Molecular beacon probes have a fluorophore attached to one arm and a quencher attached to the other arm. The fluorophore and quencher, for example, tetramethylrhodamine and DABCYL, need not be a FRET pair.

For stem loop probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region of the probe that is complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long. The stability of the interaction between the regions of a probe that reversibly interact with one another by means of complementary nucleic acid sequences is determined by routine experimentation to achieve proper functioning.

The oligonucleotide sequences of molecular beacon probes modified according to this invention may be DNA, RNA, cDNA or combinations thereof. Modified nucleotides may be included, for example nitropyrole-based nucleotides or 2'-O-methylribonucleotides. Modified linkages also may be included, for example phosphorothioates. Modified nucleotides and modified linkages may also be incorporated in wavelength-shifting primers according to this invention.

Figure 10:
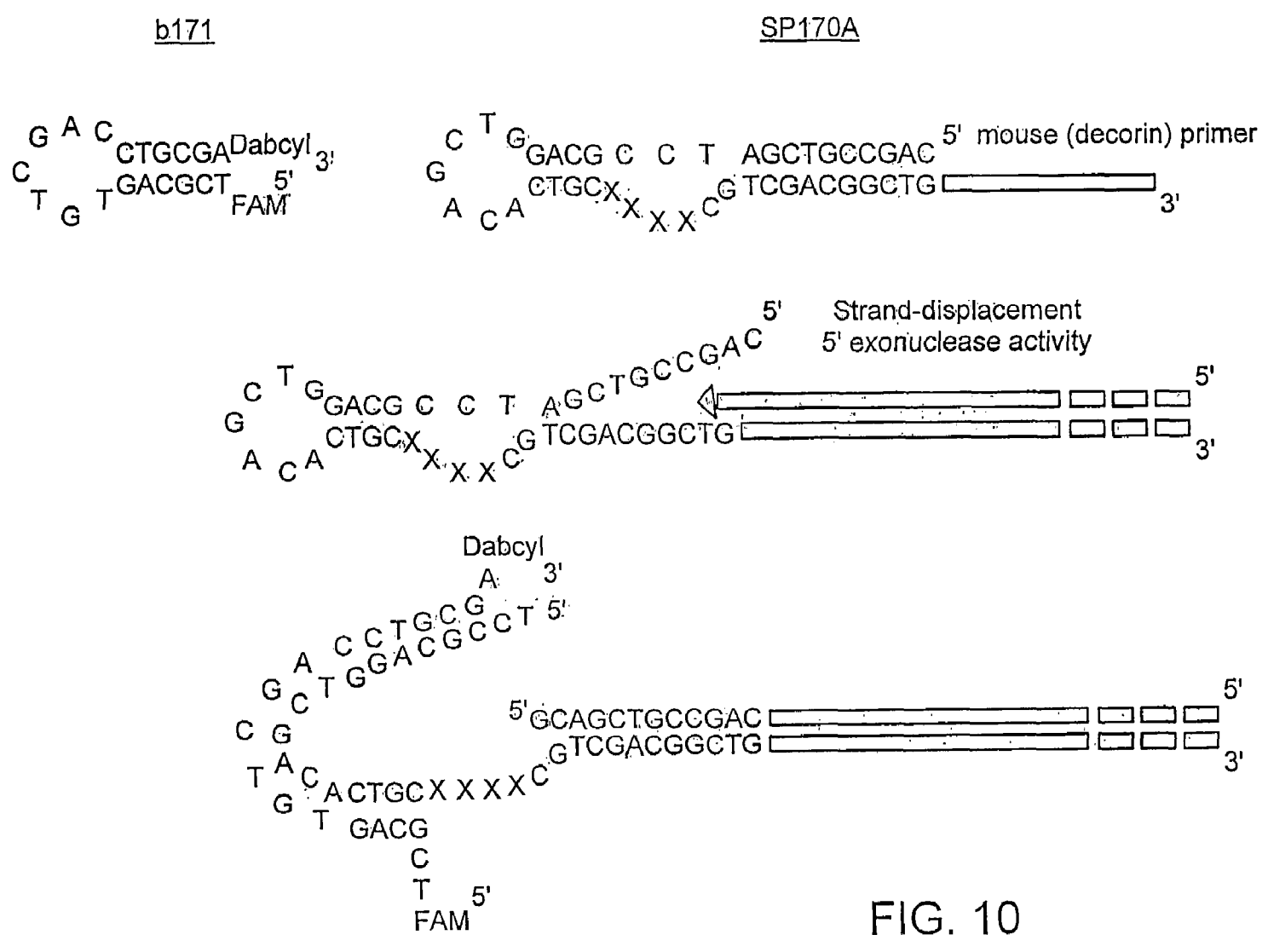

A safety pin probe, as utilized in the present invention, requires a "universal" hairpin probe 1 (FIG. 10, b171), comprising a hairpin structure, with a fluorophore (FAM) on the 5' arm of the hairpin and a quencher (Dabcyl) on the 3' arm, and a probe 2 (FIG. 10, SP170a) comprising a stem-loop comprising two domains: the 5' two thirds of probe 2 have a (universal) sequence complementary to the hairpin probe 1, and nucleotides that will stop the DNA polymerase, and the 3' one third of probe 2, which serves as the target specific primer. As the polymerase, primed from the reverse primer (that is, the 3' one third of probe 2) synthesizes the top strand, the 5' end of probe 2 will be displaced and degraded by the 5' exonucleolytic activity until the "stop nucleotides" are reached. At this time the remainder of probe 2 opens up or unfolds and serves as a target for hairpin probe 1, thereby separating the fluorophore from the quencher (FIG. 10).

Figure 11:
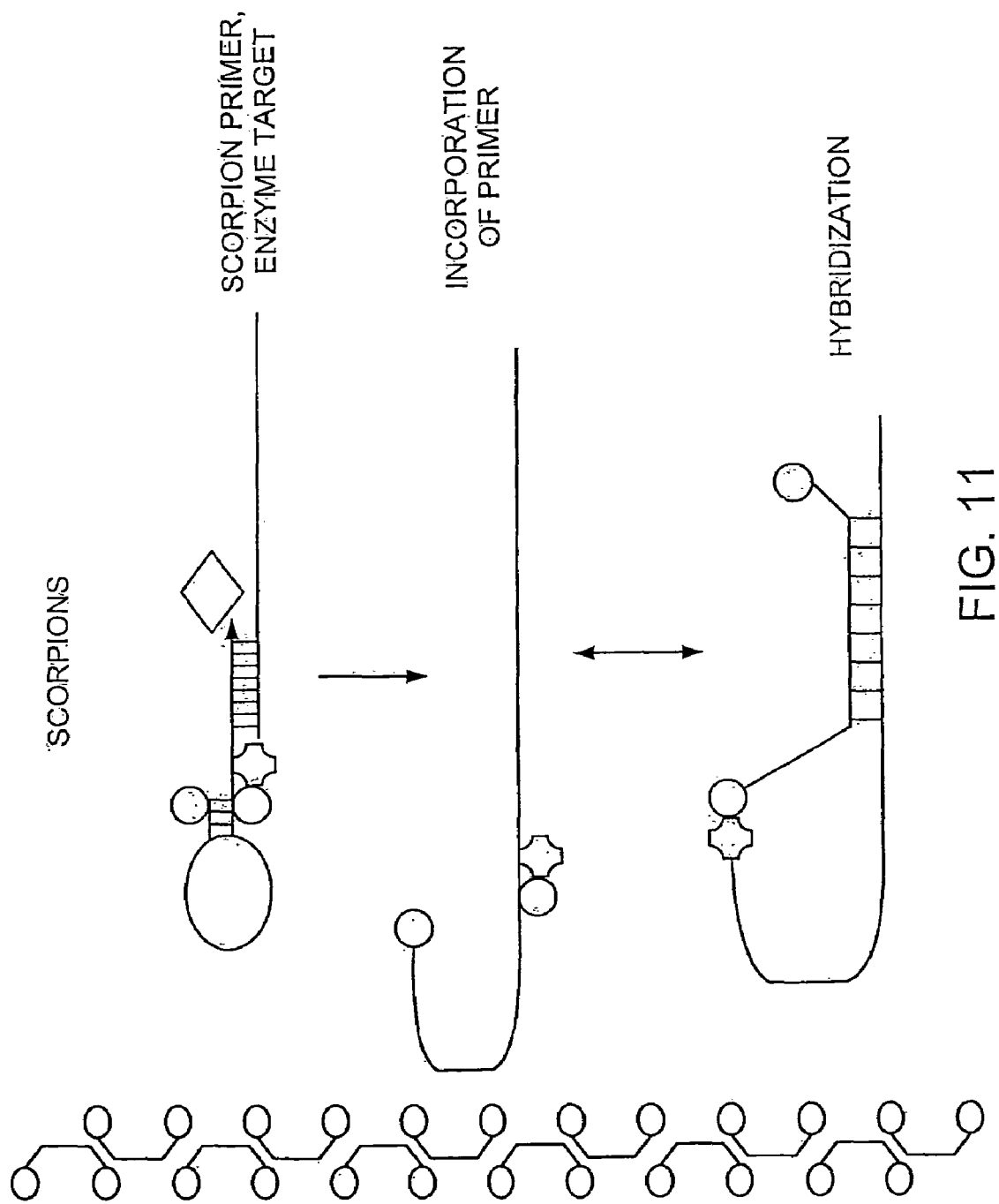
FIG. 11 is a representation of a scorpion probe.

Scorpion probes, as used in the present invention comprise a 3' primer with a 5' extended probe tail comprising a hairpin structure which possesses a fluorophore/quencher pair. The probe tail is "protected" from replication in the 5'→3' direction by the inclusion of hexethlyene glycol (HEG) which blocks the polymerase from replicating the probe. During the first round of amplification the 3' target-specific primer anneals to the target and is extended such that the scorpion is now incorporated into the newly synthesized strand, which possesses a newly synthesized target region for the 5' probe. During the next round of denaturation and annealing, the probe region of the scorpion hairpin loop will hybridize to the target, thus separating the fluorophore and quencher and creating a measurable signal. Such probes are described in Whitcombe et al., *Nature Biotechnology* 17: 804-807 (1999), and in FIG. 11.

Figure 12:
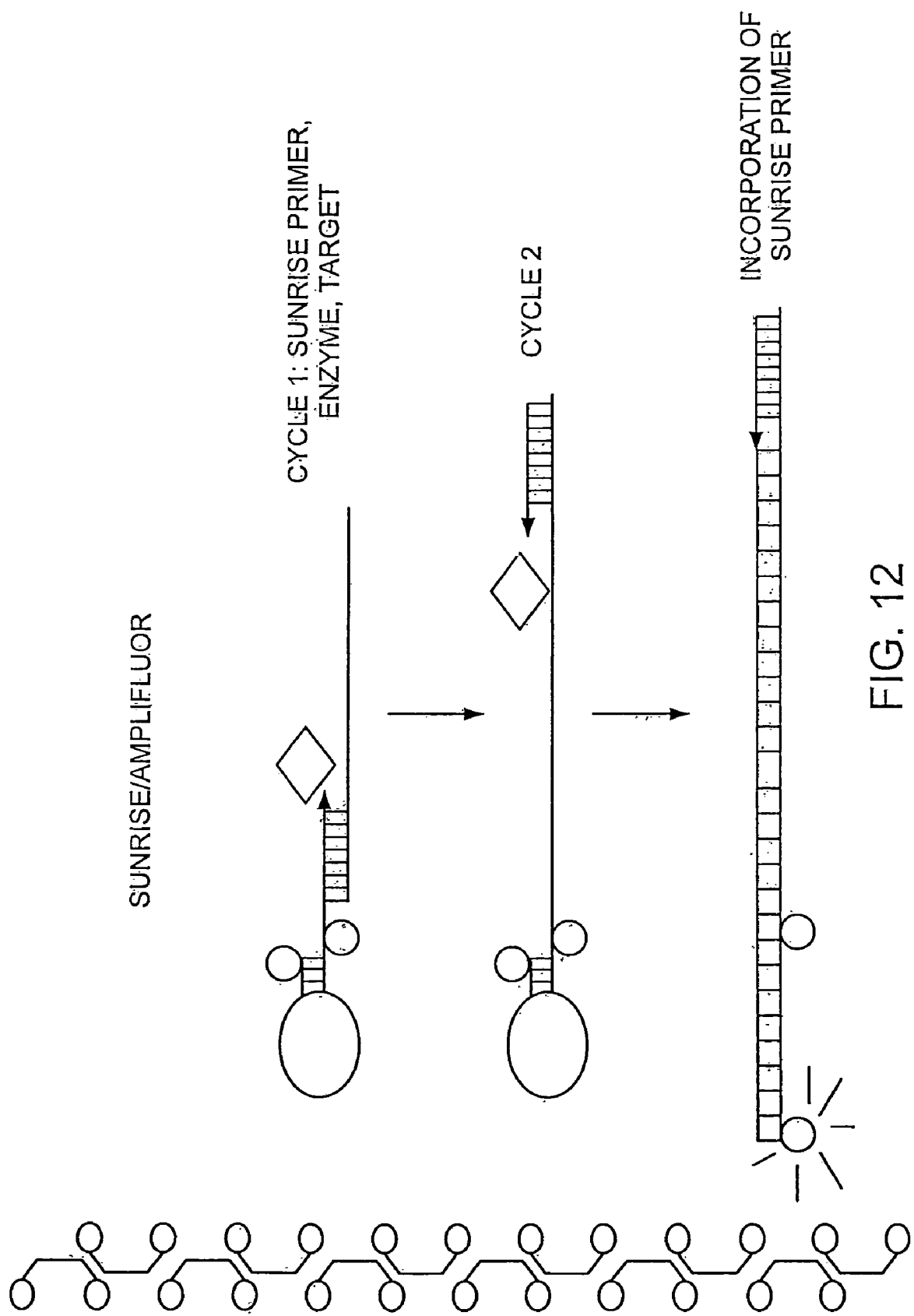
FIG. 12 is a representation of a sunrise/amplifluor probe

An additional oligonucleotide probe useful in the present invention is the sunrise/amplifluor probe. The sunrise/amplifluor probe is of similar construction as the scorpion probe with the exception that is lacks the HEG monomer to block the 5'→3' replication of the hairpin probe region. Thus, in the first round of amplification, the 3' target specific primer of the sunrise/amplifluor anneals to the target and is extended, thus incorporating the hairpin probe into the newly synthesized strand (sunrise strand). During the second round of amplification a second, non-labeled primer anneals to the 3' end of the sunrise strand (Cycle 2 in FIG. 12). However, as the polymerase reaches the 5' end of the hairpin, due to the lack of the HEG stop sequence, the polymerase will displace and replicate the hairpin, thus separating the fluorophore and quencher, and incorporating the linearized hairpin probe into the new strand. Probes of this type are described further in Nazarneko et al., *Nucleic Acid Res.* 25: 2516-2521 (1997), and in FIG. 12.

For probes useful in this invention, the length of the probe sequence that is complementary to the target, the length of the regions of a probe (e.g., stem hybrid) that reversibly interact with one another by means of complementary nucleic acid sequences when the region complementary to a nucleic acid target sequence is not bound to the target nucleic acid and the relation of the two is designed according to the assay conditions for which the probe is to be utilized. The lengths of the target-complementary sequences and the stem hybrid sequences for particular assay conditions can be estimated according to what is known in the art. The regions of a probe that reversibly interact with one another by means of complementary nucleic acid sequences when the region complementary to a nucleic acid target sequence is not bound to the target nucleic acid are in the range of 6 to 100, preferably 8 to 50 nucleotides and most preferably 8 to 25 nucleotides each. The length of the probe sequence that is complementary to the target is preferably 17-40 nucleotides, more preferably 17-30 nucleotides and most preferably 17-25 nucleotides long. The stability of the interaction between the regions of a probe that reversibly interact with one another by means of complementary nucleic acid sequences is determined by routine experimentation to achieve proper functioning. In addition to length, stability of the interaction the regions of a probe that reversibly interact with one another by means of complementary nucleic acid sequences between the regions of a probe that reversibly interact with one another by means of complementary nucleic acid sequences can be adjusted by altering the G-C content and inserting destabilizing mismatches. One of the regions of a probe that reversibly interact with one another by means of complementary nucleic acid sequences can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, or be free-floating.

A wide range of fluorophores may be used in probes and primers according to this invention. Available fluorophores include coumarin, fluorescein, tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges.

A quencher is a moiety that, when placed very close to an excited fluorophore, causes there to be little or no fluorescence. Suitable quenchers described in the art include particularly DABCYL and variants thereof, such as DABSYL, DABMI and Methyl Red. Fluorophores can also be used as quenchers, because they tend to quench fluorescence when touching certain other fluorophores. Preferred quenchers are either chromophores such as DABCYL or malachite green, or fluorophores that do not fluoresce in the detection range when the probe is in the open conformation.

Methods of labeling a probe according to the invention and suitable labels are described below in the section entitled "Cleavage Structure".

D. Production of a Nucleic Acid

The invention provides nucleic acids to be detected and or measured, for amplification of a target nucleic acid sequence and for formation of a cleavage structure.

The present invention utilizes nucleic acids comprising RNA, cDNA, genomic DNA, synthetic forms, and mixed polymers. The invention includes both sense and antisense strands of a nucleic acid. According to the invention, the nucleic acid may be chemically or biochemically modified or may contain non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which, peptide linkages substitute for phosphate linkages in the backbone of the molecule.

1. Nucleic Acids Comprising DNA a. Cloning

Nucleic acids comprising DNA can be isolated from cDNA or genomic libraries by cloning methods well known to those skilled in the art (Ausubel et al., supra). Briefly, isolation of a DNA clone comprising a particular nucleic acid sequence involves screening a recombinant DNA or cDNA library and identifying the clone containing the desired sequence. Cloning will involve the following steps. The clones of a particular library are spread onto plates, transferred to an appropriate substrate for screening, denatured, and probed for the presence of a particular nucleic acid. A description of hybridization conditions, and methods for producing labeled probes is included below.

The desired clone is preferably identified by hybridization to a nucleic acid probe or by expression of a protein that can be detected by an antibody. Alternatively, the desired clone is identified by polymerase chain amplification of a sequence defined by a particular set of primers according to the methods described below.

The selection of an appropriate library involves identifying tissues or cell lines that are an abundant source of the desired sequence. Furthermore, if a nucleic acid of interest contains regulatory sequence or intronic sequence a genomic library is screened (Ausubel et al., supra).

b. Genomic DNA

Nucleic acid sequences of the invention are amplified from genomic DNA. Genomic DNA is isolated from tissues or cells according to the following method.

To facilitate detection of a variant form of a gene from a particular tissue, the tissue is isolated free from surrounding normal tissues. To isolate genomic DNA from mammalian tissue, the tissue is minced and frozen in liquid nitrogen. Frozen tissue is ground into a fine powder with a prechilled mortar and pestle, and suspended in digestion buffer (100 mM NaCl, 10 mM Tris-HCl, pH 8.0, 25 mM EDTA, pH 8.0, 0.5% (w/v) SDS, 0:1 mg/ml proteinase K) at 1.2 ml digestion buffer per 100 mg of tissue. To isolate genomic DNA from mammalian tissue culture cells, cells are pelleted by centrifugation for 5 min at 500×g, resuspended in 1-10 ml ice-cold PBS, repelleted for 5 min at 500×g and resuspended in 1 volume of digestion buffer.

Samples in digestion buffer are incubated (with shaking) for 12-18 hours at 50° C., and then extracted with an equal volume of phenol/chloroform/isoamyl alcohol. If the phases are not resolved following a centrifugation step (10 min at 1700×g), another volume of digestion buffer (without proteinase K) is added and the centrifugation step is repeated. If a thick white material is evident at the interface of the two phases, the organic extraction step is repeated. Following extraction the upper, aqueous layer is transferred to a new tube to which will be added ½ volume of 7.5M ammonium acetate and 2 volumes of 100% ethanol. The nucleic acid is pelleted by centrifugation for 2 min at 1700×g, washed with 70% ethanol, air dried and resuspended in TE buffer (10 mM Tris-HCl, pH 8.0, 1 mM EDTA, pH 8.0) at 1 mg/ml. Residual RNA is removed by incubating the sample for 1 hour at 37° C. in the presence of 0.1% SDS and 1 μg/ml DNase-free RNase, and repeating the extraction and ethanol precipitation steps. The yield of genomic DNA, according to this method is expected to be approximately 2 mg DNA/1 g cells or tissue (Ausubel et al., supra). Genomic DNA isolated according to this method can be used for PCR analysis, according to the invention.

c. Restriction Digest (of cDNA or Genomic DNA)

Following the identification of a desired cDNA or genomic clone containing a particular target nucleic acid sequence, nucleic acids of the invention may be isolated from these clones by digestion with restriction enzymes.

The technique of restriction enzyme digestion is well known to those skilled in the art (Ausubel et al., supra). Reagents useful for restriction enzyme digestion are readily available from commercial vendors including Stratagene, as well as other sources.

d. PCR

Nucleic acids of the invention may be amplified from genomic DNA or other natural sources by the polymerase chain reaction (PCR). PCR methods are well-known to those skilled in the art.

PCR provides a method for rapidly amplifying a particular DNA sequence by using multiple cycles of DNA replication catalyzed by a thermostable, DNA-dependent DNA polymerase to amplify the target sequence of interest. PCR requires the presence of a target nucleic acid sequence to be amplified, two single stranded oligonucleotide primers flanking the sequence to be amplified, a DNA polymerase, deoxyribonucleoside triphosphates, a buffer and salts.

PCR, is performed as described in Mullis and Faloona, 1987, Methods Enzymol., 155: 335, herein incorporated by reference.

The polymerase chain reaction (PCR) technique, is disclosed in U.S. Pat. Nos. 4,683,202, 4,683,195 and 4,800,159. In its simplest form, PCR is an in vitro method for the enzymatic synthesis of specific DNA sequences, using two oligonucleotide primers that hybridize to opposite strands and flank the region of interest in the target DNA. A repetitive series of reaction steps involving template denaturation, primer annealing and the extension of the annealed primers by DNA polymerase results in the exponential accumulation of a specific fragment whose termini are defined by the 5' ends of the primers. PCR is reported to be capable of producing a selective enrichment of a specific DNA sequence by a factor of $10^9$. The PCR method is also described in Saiki et al., 1985, *Science* 230:1350.

PCR is performed using template DNA (at least 1 fg; more usefully, 1-1000 ng) and at least 25 pmol of oligonucleotide primers. A typical reaction mixture includes: 2 μl of DNA, 25 pmol of oligonucleotide primer, 2.5 μl of a suitable buffer, 0.4 μl of 1.25 μM dNTP, 2.5 units of Taq DNA polymerase (Stratagene) and deionized water to a total volume of 25 μl. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

Detection methods generally employed in standard PCR techniques use a labeled probe with the amplified DNA in a hybridization assay. Preferably, the probe is labeled, e.g., with $^{32}$P, biotin, horseradish peroxidase (HRP), etc., to allow for detection of hybridization.

Other means of detection include the use of fragment length polymorphism (PCR FLP), hybridization to allele-specific oligonucleotide (ASO) probes (Saiki et al., 1986, *Nature* 324:163), or direct sequencing via the dideoxy method (using amplified DNA rather than cloned DNA). The standard PCR technique operates (essentially by replicating a DNA sequence positioned between two primers, providing as the major product of the reaction a DNA sequence of discrete length terminating with the primer at the 5' end of each strand. Thus, insertions and deletions between the primers result in product sequences of different lengths, which can be detected by sizing the product in PCR-FLP. In an example of ASO hybridization, the amplified DNA is fixed to a nylon filter (by, for example, UV irradiation) in a series of "dot blots", then allowed to hybridize with an oligonucleotide probe labeled with HRP under stringent conditions. After washing, terramethylbenzidine (TMB) and hydrogen peroxide are added: HRP oxidizes the hydrogen peroxide, which in turn oxidizes the TMB to a blue precipitate, indicating a hybridized probe.

A PCR assay for detecting or measuring a nucleic assay according to the invention is described in the section entitled "Methods of Use".

2. Nucleic Acids Comprising RNA

The present invention also provides a nucleic acid comprising RNA.

Nucleic acids comprising RNA can be purified according to methods well known in the art (Ausubel et al., supra). Total RNA can be isolated from cells and tissues according to methods well known in the art (Ausubel et al., supra) and described below.

RNA is purified from mammalian tissue according to the following method. Following removal of the tissue of interest, pieces of tissue of ≦2 g are cut and quick frozen in liquid nitrogen, to prevent degradation of RNA. Upon the addition of a suitable volume of guanidinium solution (for example 20 ml guanidinium solution per 2 g of tissue), tissue samples are ground in a tissuiemizer with two or three 10-second bursts. To prepare tissue guanidinium solution (1 L) 590.8 g guanidinium isothiocyanate is dissolved in approximately 400 ml DEPC-treated H$_2$O. 25 ml of 2 M Tris-HCl, pH 7.5 (0.05 M final) and 20 ml Na$_2$EDTA (0.01 M final) is added, the solution is stirred overnight, the volume is adjusted to 950 ml, and 50 ml 2-ME is added.

Homogenized tissue samples are subjected to centrifugation for 10 min at 12,000×g at 12° C. The resulting supernatant is incubated for 2 min at 65° C. in the presence of 0.1 volume of 20% Sarkosyl, layered over 9 ml of a 5.7M CsCl solution (0.1 g CsCl/ml), and separated by centrifugation overnight at 113,000×g at 22° C. After careful removal of the supernatant, the tube is inverted and drained. The bottom of the tube (containing the RNA pellet) is placed in a 50 ml plastic tube and incubated overnight (or longer) at 4° C. in the presence of 3 ml tissue resuspension buffer (5 mM EDTA, 0.5%, (v/v) Sarkosyl, 5% (v/v) 2-ME) to allow complete resuspension of the RNA pellet. The resulting RNA solution is extracted sequentially with 25:24:1 phenol/chloroform/isoamyl alcohol, followed by 24:1 chloroform/isoamyl alcohol, precipitated by the addition of 3 M sodium acetate, pH 5.2, and 2.5 volumes of 100% ethanol, and resuspended in DEPC water (Chirgwin et al., 1979, *Biochemistry*, 18: 5294).

Alternatively, RNA is isolated from mammalian tissue according to the following single step protocol. The tissue of interest is prepared by homogenization in a glass teflon homogenizer in 1 ml denaturing solution (4M guanidinium thiosulfate, 25 mM sodium citrate, pH 7.0, 0.1M 2-ME, 0.5% (w/v) N-laurylsarkosine) per 100 mg tissue. Following transfer of the homogenate to a 5-ml polypropylene tube, 0.1 ml of 2 M sodium acetate, pH 4, 1 ml water-saturated phenol, and 0.2 ml of 49:1 chloroform/isoamyl alcohol are added sequentially. The sample is mixed after the addition of each component, and incubated for 15 min at 0-4° C. after all components have been added. The sample is separated by centrifugation for 20 min at 10,000×g, 4° C., precipitated by the addition of 1 ml of 100% isopropanol, incubated for 30 minutes at −20°

C. and pelleted by centrifugation for 10 minutes at 10,000×g, 4° C. The resulting RNA pellet is dissolved in 0.3 ml denaturing solution, transferred to a microfuge tube, precipitated by the addition of 0.3 ml of 100% isopropanol for 30 minutes at −20° C., and centrifuged for 10 minutes at 10,000×g at 4° C. The RNA pellet is washed in 70% ethanol, dried, and resuspended in 100-200 μl DEPC-treated water or DEPC-treated 0.5% SDS (Chomczynski and Sacchi, 1987, *Anal. Biochem.,* 162:156).

Nucleic acids comprising RNA can be produced according to the method of in vitro transcription.

The technique of in vitro transcription is well known to those of skill in the art. Briefly, the gene of interest is inserted into a vector containing an SP6, T3 or T7 promoter. The vector is linearized with an appropriate restriction enzyme that digests the vector at a single site located downstream of the coding sequence. Following a phenol/chloroform extraction, the DNA is ethanol precipitated, washed in 70% ethanol, dried and resuspended in sterile water. The in vitro transcription reaction is performed by incubating the linearized DNA with transcription buffer (200 mM Tris-HCl, pH 8.0, 40 mM $MgCl_2$, 10 mM spermidine, 250 NaCl [T7 or T3] or 200 mM Tris-HCl, pH 7.5, 30 mM $MgCl_2$, 10 mM spermidine [SP6]), dithiothreitol, RNase inhibitors, each of the four ribonucleoside triphosphates, and either SP6, T7 or T3 RNA polymerase for 30 min at 37° C. To prepare a radiolabeled polynucleotide comprising RNA, unlabeled UTP will be omitted and $^{35}$S-UTP will be included in the reaction mixture. The DNA template is then removed by incubation with DNaseI. Following ethanol precipitation, an aliquot of the radiolabeled RNA is counted in a scintillation counter to determine the cpm/μl (Ausubel et al., supra).

Alternatively, nucleic acids comprising RNA are prepared by chemical synthesis techniques such as solid phase phosphoramidite (described above).

3. Nucleic Acids Comprising Oligonucleotides

A nucleic acid comprising oligonucleotides can be made by using oligonucleotide synthesizing machines which are commercially available (described above).

IV. Cleavage Structure

The invention provides for a cleavage structure that can be cleaved by a FEN nuclease, and therefore teaches methods of preparing a cleavage structure. The invention also provides a labeled cleavage structure and methods of preparing a labeled cleavage structure.

A. Preparation of a Cleavage Structure

A cleavage structure according to the invention is formed by incubating a) an upstream, preferably extendable 3' end, preferably an oligonucleotide primer, b) an oligonucleotide probe located not more than 5000 nucleotides downstream of the upstream primer and c) an appropriate target nucleic acid sequence wherein the target sequence is complementary to both primers and d) a suitable buffer (for example Sentinel Molecular Beacon PCR core buffer (Catalog #600500) or 10× Pfu buffer available from Stratagene (Catalog #200536), under conditions that allow the nucleic acid sequence to hybridize to the oligonucleotide primers (for example 95° C. for 2-5 minutes followed by cooling to between approximately 50-60° C.). The optimal temperature will vary depending on the specific probe(s), primers and polymerases. In preferred embodiments of the invention a cleavage structure comprises an overlapping flap wherein the 3' end of an upstream oligonucleotide capable of hybridizing to a target nucleic acid sequence (for example A in FIG. 3) is complementary to 1 or more base pair(s) of the downstream oligonucleotide (for example C in FIG. 3) that is annealed to a target nucleic acid sequence and wherein the 1 base pair overlap is directly downstream of the point of extension of the single stranded flap.

The 3' end of the upstream oligonucleotide primer is extended by the synthetic activity of a polymerase according to the invention such that the newly synthesized 3' end of the upstream oligonucleotide primer partially displaces the 5' end of the downstream oligonucleotide probe. Extension is preferably carried out in the presence of 1× Sentinel Molecular beacon core buffer or 1× Pfu buffer for 15 seconds at 72° C. In one embodiment of the invention, a cleavage structure according to the invention can be prepared by incubating a target nucleic acid sequence with a partially complementary oligonucleotide primer such that the 3' complementary region anneals to the target nucleic acid sequence and the non-complementary 5' region that does not anneal to the target nucleic acid sequence forms a 5' flap. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer or 1× Pfu buffer.

B. How to Prepare a Labeled Cleavage Structure

In the present invention, a label is attached to an oligonucleotide primer comprising the cleavage structure, thereby forming a probe. Thus, the cleaved mononucleotides or small oligonucleotides which are cleaved by the endonuclease activity of the flap-specific nuclease can be detected.

A labeled cleavage structure according to the invention is formed by incubating a) an upstream extendable 3' end, preferably an oligonucleotide primer, b) a labeled probe located not more than 500 nucleotides downstream of the upstream primer and c) an appropriate target nucleic acid sequence wherein the target sequence is complementary to the oligonucleotides and d) a suitable buffer (for example 1× Sentinel Molecular beacon core buffer or 1× Pfu buffer), under conditions that allow the nucleic acid sequence to hybridize to the oligonucleotide primers (for example 95° C. for 2-5 minutes followed by cooling to between approximately 50-60° C.). A cleavage structure according to the invention also comprises an overlapping flap wherein the 3' end of an upstream oligonucleotide capable of hybridizing to a target nucleic acid sequence (for example A in FIG. 3) is complementary to 1 base pair of the downstream oligonucleotide (for example C in FIG. 3) that is annealed to a target nucleic acid sequence and wherein the 1 base pair overlap is directly downstream of the point of extension of the single stranded flap. The 3' end of the upstream primer is extended by the synthetic activity of a polymerase such that the newly synthesized 3' end of the upstream primer partially displaces the labeled 5' end of the downstream probe. Extension is preferably carried out in the presence of 1× Sentinel Molecular beacon core buffer or 1× Pfu buffer for 15 seconds at 72° C. A cleavage structure according to the invention can be prepared by incubating a target nucleic acid sequence with a probe comprising a non-complementary, labeled, 5' region that does not anneal to the target nucleic acid sequence and forms a 5' flap, and a complementary 3' region that anneals to the target nucleic acid sequence. Annealing is preferably carried out under conditions that allow the nucleic acid sequence to hybridize to the oligonucleotide primer (for example 95° C. for 2-5 minutes followed by cooling to between approximately 50-60° C.) in the presence a suitable buffer (for example 1× Sentinel Molecular beacon core buffer or 1× Pfu buffer).

Subsequently, any of several strategies may be employed to distinguish the uncleaved labeled nucleic acid from the cleaved fragments thereof. In this manner, the present invention permits identification of those samples that contain a target nucleic acid sequence.

The oligonucleotide probe is labeled, as described below, by incorporating moieties detectable by spectroscopic, photochemical, biochemical, immunochemical, enzymatic or chemical means. The method of linking or conjugating the label to the oligonucleotide probe depends, of course, on the type of label(s) used and the position of the label on the probe. Preferably a probe is labeled at the 5' end although probes labeled at the 3' end or labeled throughout the length of the probe are also useful in particular embodiments of the invention.

A variety of labels that would be appropriate for use in the invention, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origen™ (Igen), that may interact with each other to enhance, alter, or diminish a signal. Of course, if a labeled molecule is used in a PCR based assay carried out using a thermal cycler instrument, the label must be able to survive the temperature cycling required in this automated process.

Among radioactive atoms, $^{33}P$ or, $^{32}P$ is preferred. Methods for introducing $^{33}P$ or, $^{32}P$ into nucleic acids are known in the art, and include, for example, 5' labeling with a kinase, or random insertion by nick translation. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. The above description is not meant to categorize the various labels into distinct classes, as the same label may serve in several different modes. For example, $^{125}I$ may serve as a radioactive label or as an electron-dense reageant. HRP may serve as an enzyme or as antigen for a monoclonal antibody. Further, one may combine various labels for desired effect. For example, one might label a probe with biotin, and detect the presence of the probe with avidin labeled with $^{125}I$, or with an anti-biotin monoclonal antibody labeled with HRP. Other permutations and possibilities will be readily apparent to those of ordinary skill in the art and are considered as equivalents within the scope of the instant invention.

Fluorophores for use as labels in constructing labeled probes of the invention include rhodamine and derivatives (such as Texas Red), fluorescein and derivatives (such as 5-bromomethyl fluorescein), Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromorimethyl-ammoniobimane. In general, fluorophores with wide Stokes shifts are preferred, to allow using fluorimeters with filters rather than a monochromometer and to increase the efficiency of detection.

Probes labeled with fluorophores can readily be used in FEN mediated cleavage of a cleavage structure comprising a labeled probe according to the invention. If the label is on the 5'-end of the probe, the FEN generated labeled fragment is separated from the intact, hybridized probe by procedures well known in the art. The fluorescence of the released label is then compared to the label remaining bound to the target. It is not necessary to separate the FEN generated fragment and the probe that remains bound to the target after cleavage in the presence of FEN if the probe is synthesized with a fluorophore, usually at the 5'-end, and a quencher, usually about 20 nucleotides downstream of the dye. Such a dual labeled probe will not fluoresce when intact because the light emitted from the dye is quenched by the quencher. Thus, any fluorescence emitted by an intact probe is considered to be background fluorescence. When a labeled probe is cleaved by a FEN nuclease, dye and quencher are separated and the released fragment will fluoresce. The amount of fluorescence is proportional to the amount of nucleic acid target sequence present in a sample.

In some situations, one can use two interactive labels on a single oligonucleotide with due consideration given for maintaining an appropriate spacing of the labels on the oligonucleotide to permit the separation of the labels during oligonucleotide hydrolysis. Preferred interactive labels useful according to the invention include, but are not limited to rhodamine and derivatives, fluorescein and derivatives, Texas Red, coumarin and derivatives, crystal violet and include, but are not limited to DABCYL, TAMRA and NTB (nitrothiazole blue).

In another embodiment of the invention, detection of the hydrolyzed, labeled probe can be accomplished using, for example, fluorescenrce polarization, a technique to differentiate between large and small molecules based on molecular tumbling. Large molecules (i.e., intact labeled probe) tumble in solution much more slowly than small molecules. Upon linkage of a fluorescent moiety to the molecule of interest (e.g., the 5' end of a labeled probe), this fluorescent moiety can be measured (and differentiated) based on molecular tumbling, thus differentiating between intact and digested probe.

In yet another embodiment, two labeled nucleic acids are used, each complementary to separate regions of separate strands of a double-stranded target sequence, but not to each other, so that a labeled nucleic acid anneals downstream of each primer. For example, the presence of two probes can potentially double the intensity of the signal generated from a single label and may further serve to reduce product strand reannealing, as often occurs during PCR amplification. The probes are selected so that the probes bind at positions adjacent (downstream) to the positions at which primers bind.

One can also use multiple probes in the present invention to achieve other benefits. For instance, one could test for any number of pathogens in a sample simply by putting as many probes as desired into the reaction mixture; the probes could each comprise a different label to facilitate detection.

One can also achieve allele-specific or species-specific discrimination using multiple probes in the present invention, for instance, by using probes that have different T$_m$s and conducting the annealing/cleavage reaction at a temperature specific for only one probe/allele duplex. One can also achieve allele specific discrimination by using only a single probe and examining the types of cleavage products generated. In this embodiment of the invention, the probe is designed to be exactly complementary, at least in the 5' terminal region, to one allele but not to the other allele(s). With respect to the other allele(s), the probe will be mismatched in the 5' terminal region of the probe so that a different cleavage product will be generated as compared to the cleavage product generated when the probe is hybridized to the exactly complementary allele.

Although probe sequence can be selected to achieve important benefits, one can also realize important advantages by selection of probe labels(s). The labels may be attached to the oligonucleotide directly or indirectly by a variety of techniques. Depending on the precise type of label used, the label can be located at the 5' or 3' end of the probe, located internally in the probe, or attached to spacer arms of various sizes and compositions to facilitate signal interactions. Using commercially available phosphoramidite reagents, one can produce oligomers containing functional groups (e.g., thiols or primary amines) at either the 5'- or the 3'-terminus via an appropriately protected phosphoramidite, and can label them using protocols described in, for example, PCR Protocols: A Guide to Methods and Applications, Innis et al., eds. Academic Press, Ind., 1990.

Methods for introducing oligonucleotide functionalizing reagents to introduce one or more sulfhydryl, amino or hydroxyl moieties into the oligonucleotide probe sequence, typically at the 5' terminus, are described in U.S. Pat. No. 4,914,210. A 5' phosphate group can be introduced as a radioisotope by using polynucleotide kinase and gamma-$^{32}$P-ATP or gamma-$^{33}$P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin$^{35}$S-dATP, and biotinylated dUTP.

Oligonucleotide derivatives are also available labels. For example, etheno-dA and etheno-A are known fluorescent adenine nucleotides that can be incorporated into a nucleic acid probe. Similarly, etheno-dC or 2-amino purine deoxyriboside is another analog that could be used in probe synthesis. The probes containing such nucleotide derivatives may be hydrolyzed to release much more strongly fluorescent mononucleotides by flap-specific nuclease activity.

C. Cleaving a Cleavage Structure and Generating a Signal

A cleavage structure according to the invention can be cleaved by the methods described in the section above, entitled "FEN Nucleases".

D. Detection of Released Labeled Fragments

Detection or verification of the labeled fragments may be accomplished by a variety of methods well known in the art and may be dependent on the characteristics of the labeled moiety or moieties comprising a labeled cleavage structure.

In one embodiment of the invention, the reaction products, including the released labeled fragments, are subjected to size analysis. Methods for determining the size of a labeled fragment are known in the art and include, for example, gel electrophoresis, sedimentation in gradients, gel exclusion chromatography, mass spectroscopy, and homochromatography.

During or after amplification, separation of the released labeled fragments from, for example, a PCR mixture can be accomplished by, for example, contacting the PCR with a solid, phase extractant (SPE). For example, materials having an ability to bind nucleic acids on the basis of size, charge, or interaction with the nucleic acid bases can be added to the PCR mixture, under conditions where labeled, uncleaved nucleic acids are bound and short, labeled fragments are not. Such SPE materials include ion exchange resins or beads, such as the commercially available binding particles Nensorb (DuPont Chemical Co.), Nucleogen (The Nest Group), PEI, BakerBond™ PEI, Amicon PAE 1,000, Selectacel™ PEI, Boronate SPE with a 3'-ribose probe, SPE containing sequences complementary to the 3'-end of the probe, and hydroxylapatite. In a specific embodiment, if a dual labeled oligonucleotide comprising a 3' biotin label separated from a 5' label by a nuclease susceptible cleavage site is employed as the signal means, the reaction mixture, for example a PCR amplified mixture can be contacted with materials containing a specific binding partner such as avidin or streptavidin, or an antibody or monoclonal antibody to biotin. Such materials can include beads and particles coated with specific binding partners and can also include magnetic particles.

Following the step in which a reaction mixture, for example a PCR mixture has been contacted with an SPE, the SPE material can be removed by filtration, sedimentation, or magnetic attraction, leaving the labeled fragments free of uncleaved labeled oligonucleotides and available for detection.

IV. Methods of Use

The invention provides for a method of generating a signal indicative of the presence of a target nucleic acid sequence in a sample comprising the steps of forming a labeled cleavage structure by incubating a target nucleic acid sequence with a nucleic acid polymerase, and cleaving the cleavage structure with a FEN nuclease. The method of the invention can be used in a PCR based assay as described below.

A labeled cleavage structure comprising an upstream oligonucleotide primer (for example A, FIG. 3), a 5' end labeled downstream oligonucleotide probe (for example C in FIG. 3) and a target nucleic acid sequence (for example B in FIG. 3) is formed as described above in the section entitled "Cleavage Structure". Briefly, a cleavage structure is formed and cleaved in the presence of a target nucleic acid sequence, an upstream primer (for example A, FIG. 3), a labeled downstream probe (for example C, FIG. 3) amplification primers specific for the target nucleic acid sequence, a nucleic acid polymerase deficient in 5' to 3' exonuclease activity, a FEN nuclease and an appropriate buffer (for example 10× Pfu buffer, Stratagene, Catalog# 200536) in a PCR reaction with the following thermocycling parameters: 95° C. for 2 minutes and 40 cycles of 95° C. for 15 sec (denaturation step), 60° C. for 60 sec (annealing step)and 72° C. for 15 sec (extension step). During this reaction an upstream oligonucleotide (for example A, FIG. 3) is extended such that oligonucleotide A partially displaces the 5' labeled end of a downstream oligonucleotide that is annealed to a target nucleic acid sequence (for example oligonucleotide C, FIG. 3) and the resulting labeled structure is cleaved with a FEN nuclease according to the invention.

The methods of the invention can also be used in non-PCR based applications to detect a target nucleic acid sequence, where such target that may be immobilized on a solid support. Methods of immobilizing a nucleic acid sequence on a solid support are known in the art and are described in Ausubel FM et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports useful according to the invention, CPG, Inc. A solid support useful according to the invention includes but is not limited to silica based matrices, membrane based matrices and beads comprising surfaces including, but not limited to styrene, latex or silica based materials and other polymers. Magnetic beads are also useful according to the invention. Solid supports can be obtained from the above manufacturers and other known manufacturers.

The invention also provides for a non-PCR based assay for detecting a target nucleic acid sequence in solution. The method of the invention can be used to detect naturally occurring target nucleic acid sequences in solution including but not limited to RNA and DNA that is isolated and purified from cells, tissues, single cell organisms, bacteria or viruses. The method of the invention can also be used to detect synthetic targets in solution, including but not limited to RNA or DNA oligonucleotides, and peptide nucleic acids (PNAs). Non-PCR assays include but are not limited to detection assays involving isothermal linear or exponential amplification, where the amount of nucleic acid synthesized by the 3'-5' synthetic activity increases linearly or exponentially, and a FEN nuclease is used to cleave the displaced strand during synthesis. One such example utilizes rolling circle amplification.

Detection of a nucleic acid target sequence that is either immobilized or in solution can be performed by incubating an immobilized nucleic acid target sequence or a target nucleic acid sequence in solution with an upstream oligonucleotide primer that is complementary to the target nucleic acid sequence (for example A, FIG. 3) and a downstream oligonucleotide probe that is complementary to the target nucleic acid sequence (for example C, FIG. 3), a FEN nuclease and a nucleic acid polymerase lacking 5' to 3' exonuclease activity. The downstream probe is either end labeled at the 5' or 3' end, or is labeled internally. Detection of a released labeled fragment involves isotopic, enzymatic, or colorimetric methods appropriate for the specific label that has been incorporated into the probe. Labels useful according to the invention and methods for the detection of labels useful according to the invention are described in the section entitled "Cleavage Structure". Alternatively, the downstream probe comprises a pair of interactive signal generating labeled moieties (for example a dye and a quencher) that are positioned such that when the probe is intact, the generation of a detectable signal is quenched, and wherein the pair of interactive signal generating moieties are separated by a FEN nuclease cleavage site. Upon cleavage by a FEN nuclease, the two signal generating moieties are separated from each other and a detectable signal is produced. Nucleic acid polymerases that are useful for detecting an immobilized nucleic acid target sequence or a nucleic acid target sequence in solution according to the method of the invention include mesophilic, thermophilic or hyper-thermophilic DNA polymerases lacking 5' to 3' exonucleolytic activity (described in the section entitled, "Nucleic Acid Polymerases)".

According to this non-PCR based method, the amount of a target nucleic acid sequence that can be detected is preferably about 1 pg to 1 μg, more preferably about 1 pg to 10 ng and most preferably about 1 pg to 10 pg. Alternatively, this non-PCR based method can measure or detect preferably about 1 molecule to $10^{20}$ molecules, more preferably about 100 molecules to $10^{17}$ molecules and most preferably about 1000 molecules to $10^{14}$ molecules.

The invention also provides for a method of detecting a target nucleic acid sequence in a sample wherein a cleavage structure is formed as described in the section entitled, "Cleavage Structure", and the target nucleic acid sequence is amplified by a non-PCR based method including but not limited to an isothermal method, for example rolling circle, Self-sustained Sequence Replication Amplification (3SR), Transcription based amplification system (TAS), and Strand Displacement Amplification (SDA) and a non-isothermal method, for example Ligation chain reaction (LCR). A FEN nuclease useful for non-PCR amplification methods will be active at a temperature range that is appropriate for the particular amplification method that is employed.

In the amplification protocols described below, samples which need to be prepared in order to quantify the target include: samples, no-template controls, and reactions for preparation of a standard curve (containing dilutions over the range of six orders of magnitude of a solution with a defined quantity of target).

Strand Displacement Amplification (SDA) is based on the ability of a restriction enzyme to nick the unmodified strand of a hemiphosphorothioate form of its recognition site. The appropriate DNA polymerase will initiate replication at this nick and displace the downstream non-template strand (Walker, 1992, Proc. Natl. Acad. Sci. USA, 89: 392, and PCR Methods and Applications 3: 1-6, 1993). The polymerases (Bca and Bst) which are used according to the method of SDA can also be used in FEN directed cleavage according to the invention. According to the method of the invention, a molecular beacon is replaced by a FEN nuclease active at 42° C. and a cleavable probe comprising a cleavage structure according to the invention.

A molecular beacon (Mb) is a fluorogenic probe which forms a stem-loop structure is solution. Typically: 5'-fluorescent dye (e.g. FAM), attached to the 5'-stem region (5-7 nt), the loop region (complementary to the target, 20 to 30 nt), the 3'-stem region (complementary to the 5'-stem region), and the quencher (e.g. DABCYL). If no target is present, the MB forms its stem, which brings dye and quencher into close proximity, and therefore no fluorescence is emitted. When an MB binds to its target, the stem is opened, dye is spatially separated from the quencher, and therefore the probe emits fluorescence (Tyagi S and Kramer F R, Nature Biotechnology 14: 303-308 (1996) and U.S. Pat. No. 5,925,517).

Strand Displacement Amplification (SDA) is essentially performed as described by Spargo et al., Molecular and Cellular Probes 10: 247-256 (1996). The enzymes used include restriction endonuclease BsoBI (New England Biolabs), DNA polymerase 5'-exo-Bca (Pan Vera Corporation). The target is an insertion-like element (IS6110) found in the *Mycobacterium tuberculosis* (Mtb) genome. The primers used are B1: cgatcgagcaagcca, B2: cgagccgctcgctg, S1: accgcatcgaatgcatgtctcgggtaaggcgtactcgacc and S2: cgattccgctccagacttctcgggtgtactgagatcccct. The *Mycobacterium tuberculosis* genomic DNA is serially diluted in human placental DNA. SDA is performed in 50 ul samples containing 0 to 1000 Mtb genome equivalents, 500 ng human placental DNA, 160 units BsoB1, 8 units of 5'-exo-Bca, 1.4 mM each dCTPalphaS, TTP, dGTP, dATP, 35 mM $K_2PO_4$, pH 7.6 0.1 mg/ml acetylated bovine serum albumin (BSA), 3 mM Tris-HCl, 10 mM $MgCl_2$, 11 mM NaCl, 0.3 mM DTT, 4 mM KCl, 4% glycerol, 0.008 mM EDTA, 500 nM primers S1 and S2 and 50 nM primers B1 and B2 (KCl, glycerol and EDTA are contributed by the BsoB1 storage solution). The samples (35 μl) were heated in a boiling water bath for 3 minutes before the addition of BsoB1 and 5'-exo Bca (10.7 units/μl BsoB1 and 0.53 units/μl 5'-exo Bca in 15 μl of New England Biolabs Buffer 2 (20 mM Tris-HCl pH 7.9, 10 mM $MgCl_2$, 50 mM NaCl, 1 mM DTT). Incubation is at 60° C. for 15 minutes, followed by 5 minutes in a boiling water bath.

Five μl of each sample in duplicate are removed for detection. Each reaction contains 1× Cloned Pfu buffer, 3.0 mM $MgCl_2$, 200 uM of each dNTP, 5 units exo-Pfu, 23 ng Pfu FEN-1, 1 ng PEF, 300 nM each upstream primer: aaggcgtactcgacctgaaa and fluorogenic probe (for example FAM-DABCYL): accatacggataggggatctc. The reactions are subjected to one cycle in a thermal cycler: 2 minutes at 95° C., 1 minute at 55° C., 1 minute at 72° C. The fluorescence is then determined in a fluorescence plate reader, such as Stratagene's FluorTracker or PE Biosystems' 7700 Sequence Detection System in Plate-Read Mode.

According to the method of nucleic acid sequence-based amplification (NASBA), molecular beacons are used for quantification of the NASBA RNA amplicon in real-time analysis (Leone, et al., 1998, *Nucleic Acids Res*. 26: 2150). According to the method of the invention, NASBA can be carried out wherein the molecular beacon probe is replaced by a FENnuclease cleavable probe comprising a cleavage structure according to the invention and a FEN nuclease active at 41° C.

NASBA amplification is performed essentially as described by Leone G, et al., Nucleic Acids Res. 26: 2150-2155 (1998). Genomic RNA from the potato leafroll virus (PLRV) is amplified using the PD415 or PD416 (antisense) and the PD417 (sense) primers, which are described in detail in Leone G et al., J. Virol. Methods 66: 19-27 (1997). Each NASBA reaction contains a premix of 6 µl of sterile water, 4 µl of 5× NASBA buffer (5× NASBA buffer is 200 mM Tris-HCl, pH 8.5, 60 mM MgCl$_2$, 350 mM KCl, 2.5 mM DTT, 5 mM each of dNTP, 10 mM each of ATP, UTP and CTP, 7.5 mM GTP and 2.5 mM ITP), 4 µl of 5× primer mix (75% DMSO and 1 µM each of antisense and sense primers). The premix is divided into 14 µl aliquots, to which 1 µl of PLRV target is added. After incubation for 5 minutes at 65° C. and cooling to 41° C. for 5 minutes, 5 µl of enzyme mix is added (per reaction 375 mM sorbitol, 2.1 µg BSA, 0.08 units of RNase H (Pharmacia), 32 units of T7 RNA polymerase (Pharmacia) and 6.4 units of AMV-RT (Seigakaku)). Amplification is for 90 minutes at 41° C.

Five µl of each sample in duplicate are removed for detection. Each reaction contains 1× Cloned Pfu buffer, 3.0 mM MgCl$_2$, 200 uM of each dNTP, 5 units exo-Pfu, 23 ng Pfu FEN-1, 1 ng PEF, 300 nM each upstream primer PD415 or PD416 and the fluorogenic probe (for example FAM-DAB-CYL) gcaaagtatcatcctccag. The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Biosystems' 7700 Sequence Detection System in Plate-Read Mode.

Generally, according to these methods wherein amplification occurs by a non-PCR based method, amplification may be carried out in the presence of a FEN nuclease, and amplification and cleavage by the FEN nuclease occur simultaneously. Detection of released labeled fragments is performed as described in the section entitled "Cleavage Structure" and may occur concurrently with (real time) or after (end-point) the amplification and cleavage process have been completed.

End point assays can be used to quantify amplified target produced by non-PCR based methods wherein the amplification step is carried out in the presence of a FEN nuclease (described above).

Endpoint assays include, but are not limited to the following.

A. Ligation chain reaction (LCR), as described in Landegren, et al., 1988; *Science*, 241: 1077 and Barany, PCR Methods and Applications 1: 5-16 (1991). An LCR product useful according to the invention will be long enough such that the upstream primer and the labeled downstream probe are separated by a gap larger than 8 nucleotides to allow for efficient cleavage by a FEN nuclease.

B. Self-sustained sequence replication amplification (3SR) Fahy, et al. PCR Methods and Applications 1: 25-33 (1991). Self-Sustained Sequence Replication Amplification (3SR) is a technique which is similar to NASBA. Ehricht R, et al., Nucleic Acids Res. 25: 4697-4699 (1997) have evolved the 3SR procedure to a cooperatively coupled in vitro amplification system (CATCH). Thus, in CATCH, a molecular beacon probe is used for real-time analysis of an RNA amplicon. The synthetic target amplified has the sequence: cctctgcagactactattacataatacgactcactataggggatc tgcacgtattagcctatagtgagtcgtattaataggaaacaccaaagatgatatttcgtcacagcaagaattcagg. The 3SR reactions contain 40 mM Tris-HCl pH 8.0, 5 mM KCl, 30 mM MgCl$_2$, 1 mM of each dNTP, 1 nM of the double stranded target, 2 µM P1: cctctgcagactactattac and P2:cctgaattcttgct-gtgacg, 5 mM DTT, 2 mM spermidine, 6 units/ul His tagged HIV-1 reverse transcriptase, 3 units/ul T7-RNA polymerase and 0.16 units/ul *Escherichia coli* RNase H. The 100 ul reactions are incubated for 30 minutes at 42° C.

Five µl of each sample in duplicate are removed for detection. Each reaction contains 1× Cloned Pfu buffer, 3.0 mM MgCl$_2$, 200 uM of each dNTP, 5 units exo-Pfu, 23 ng Pfu FEN-1, 1 ng PEF, 300 nM each upstream primer P1 and fluorogenic probe (for example FAM-DABCYL): taggaaa-caccaaagatgatattt. The reactions are subjected to one cycle in a thermal cycler: 2 minutes at 95° C., 1 minute at 55° C., 1 minute at 72° C. The fluorescence in then determined in a fluorescence plate reader, such as Stratagene's FluorTracker or PE Biosystems' 7700 Sequence Detection System in Plate-Read Mode.

C. Rolling circle amplification is described in U.S. Pat. No. 5,854,033 and the related Ramification-Extension Amplification Method (RAM) (U.S. Pat. No. 5,942,391). Rolling circle amplification adapted to the invention is described in Example 3 below.

Real-time assays can also be used to quantify amplified target produced by non-PCR based methods wherein the amplification step is carried out in the presence of a FEN nuclease (described above). The method of rolling circle amplification (U.S. Pat. No. 5,854,033) is adapted to include secondary primers for amplification and detection, in conjunction with a FEN nuclease and a cleavable probe comprising a cleavage structure according to the invention and is carried out at temperatures between 50-60° C.

The cleavage pattern of a FEN nuclease can be altered by the presence of a single mismatched base located anywhere between 1 and 15 nucleotides from the 5' end of the primer wherein the DNA primer is otherwise fully annealed. Typically, on a fully annealed substrate, a FEN nuclease will exonucleolytically cleave the 5' most nucleotide. However, a single nucleotide mismatch up to 15 nucleotides in from the 5' end promotes endonucleolytic cleavages. This constitutes a 5' proofreading process in which the mismatch promotes the nuclease action that leads to its removal. Thus, the mechanism of FEN nuclease cleavage is shifted from predominantly exonucleolytic cleavage to predominantly endonucleolytic cleavage simply by the presence of a single mismatched base pair. Presumably this occurs because a mismatch allows a short flap to be created (Rumbaugh et al., 1999, *J. Biol. Chem.*, 274:14602).

The method of the invention can be used to generate a signal indicative of the presence of a sequence variation in a target nucleic acid sequence, wherein a labeled cleavage structure comprising a fully annealed DNA primer is formed by incubating a target nucleic acid sequence with a nucleic acid polymerase (as described in the section entitled, "Cleavage Structure") and cleaving the labeled cleavage structure with a FEN nuclease wherein the release of labeled fragments comprising endonucleolytic cleavage products is indicative of the presence of a sequence variation. Released labeled fragments are detected as described in the section entitled, "Cleavage Structure".

V. Samples

The invention provides for a method of detecting or measuring a target nucleic acid sequence in a sample, as defined herein. As used herein, "sample" refers to any substance containing or presumed to contain a nucleic acid of interest (a target nucleic acid sequence) or which is itself a target nucleic acid sequence containing or presumed to contain a target nucleic acid sequence of interest. The term "sample" thus includes a sample of target nucleic acid sequence (genomic DNA, cDNA or RNA), cell, organism, tissue, fluid or substance including but not limited to, for example, plasma, serum, spinal fluid, lymph fluid, synovial fluid, urine, tears, stool, external secretions of the skin, respiratory, intestinal and genitourinary tracts, saliva, blood cells, tumors, organs, tissue, samples of in vitro cell culture constituents, natural isolates (such as drinking water, seawater, solid materials,) microbial specimens, and objects or specimens that have been "marked" with nucleic acid tracer molecules.

EXAMPLES

The invention is illustrated by the following nonlimiting examples wherein the following materials and methods are employed. The entire disclosure of each of the literature references cited hereinafter are incorporated by reference herein.

Example 1

A target nucleic acid sequence can be detected and/or measured by the following method. A labeled cleavage structure is formed prior to the addition of a FEN nuclease by heating at 95° C. for 5 minutes and then cooling to approximately 50-60° C. (a) a sample containing a target nucleic acid sequence (B in FIG. 3) with (b) an upstream oligonucleotide that specifically hybridizes to the target nucleic acid sequence, (A, in FIG. 3), and (c) a downstream, 5' end labeled oligonucleotide (C in FIG. 3) that specifically hybridizes to a region of the target nucleic acid sequence that is downstream of the hybridizing region of oligonucleotide A. A polymerase that lacks a 5' to 3' exonuclease activity but that possesses a 3' to 5' DNA synthetic activity, such as the enzyme a) Yaq exo-, (prepared by mutagenesis using the Stratagene QuikChange Site-Directed Mutagenesis kit, catalog-number #200518, to modify Taq polymerase (Tabor and Richardson, 1985, Proc. Natl. Acad. Sci. USA, 82:1074)), a mutant form of Taq polymerase that lacks 5' to 3' exonuclease activity, b) Pfu, or c) a mutant form of Pfu polymerase that lacks 3' to 5' exonuclease activity (exo-Pfu) is added and incubated under conditions that permit the polymerase to extend oligonucleotide A such that it partially displaces the 5' end of oligonucleotide C (for example 72° C. in 1×Pfu buffer (Stratagene) for 5 minutes to 1 hour. The displaced region of oligonucleotide C forms a 5' flap that is cleaved upon the addition of a FEN nuclease.

A mutant form of Taq polymerase that lacks a 5' to 3' exonuclease activity but that possesses a 3' to 5' DNA synthetic activity comprises the following mutation: D144S/F667Y Taq wherein D144S eliminates 5' to 3' exonuclease activity and F667Y improves ddNTP incorporation.

Exo-mutants of PolI polymerase can be prepared according to the method of Xu et al., 1997, J. Mol. Biol., 268: 284.

A labeled cleavage structure according to the invention is cleaved with a preparation of PfuFEN-1 (i.e. cloned *Pyrococcus furiosus* FEN-1 that is prepared as described below in Example 2). Cleavage is carried out by adding 2 µl of PfuFEN-1 to a 7 µl reaction mixture containing the following:

| | |
|---|---|
| 3 µl | cleavage structure (10 ng-10 µg) |
| 0.7 µl | 10× FEN nuclease buffer (10× FEN nuclease buffer contains 500 mM Tris-HCl pH 8.0, 100 mM MgCl$_2$) |
| 2.00 µl | PfuFEN-1 enzyme or H$_2$O |
| 1.3 µl | H$_2$O |
| 7.00 µl | total volume |

Samples are incubated for one hour at 50° C. in a Robocyler 96 hot top thermal cycler. Following the addition of 2 µl of Sequencing Stop dye solution (included in the Stratagene Cyclist DNA sequencing kit, catalog #200326, and described in example 3), samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3mm paper, covered with plastic wrap and dried for 2 hours in a heated vacuum gel dryer (~80° C.). The gel is exposed overnight to X-ray film to detect the presence of a signal that is indicative of the presence of a target nucleic acid sequence.

Example 2

Cloning Pfu FEN-1

A thermostable FEN nuclease enzyme useful according to the invention can be prepared according to the following method.

The thermostable FEN nuclease gene can be isolated from genomic DNA derived from *P. furiosus* (ATCC#43587) according to methods of PCR cloning well known in the art. The cloned PfuFEN-1 can be overexpressed in bacterial cells according to methods well known in the art and described below.

The following pCAL-n-EK cloning oligonucleotides were synthesized and purified:

a.
5' GACGACGACAAGATGGGTGTCCCAATTGGTGAGATTATACCAAGAAA AG 3'
and b.
5' GGAACAAGACCCGTTTATCTCTTGAACCAACTTTCAAGGGTTGATTG TTTTCCACT 3'.

The Affinity® Protein Expression and Purification System was obtained from Stratagene and used according to the manufacturer's protocols.

Amplification

The insert DNA was prepared by PCR amplification with gene-specific primers (oligonucleotides a and b, described above) that include 12 and 13-nucleotide sequences at the 5' ends that are complementary to the pCAL-n-EK vector single-stranded tails, thus allowing for directional cloning. The FEN-1 sequence was amplified from genomic DNA derived from *P. furiosus* by preparing amplification reactions (five independent 100 µl reactions) containing:

| | |
|---|---|
| 50 µl | 10× cPfu Buffer (Stratagene) |
| 7.5 µl | Pfu Genomic DNA (approx. 100 ng/µl) |
| 7.5 µl | PfuTurbo(2.5 u/µl), (Stratagene, Catalog # 600250) |
| 15 µl | mixed primer pair (100 ng/µl each) (oligonucleotides a and b, described above) |
| 4 µl | 100 mM dNTP |
| 416 µl | H$_2$O |
| 500 µl | total | and carrying out the amplification under the following conditions using a Stratagene Robocycler 96 hot top thermal cycler:

| Window 1 | 95° C. | 1 minute | 1 cycle |
| Window 2 | 95° C. | 1 minute | |
| | 50° C. | 1 minute | 30 cycles |
| | 72° C. | 3 minutes | |

The PCR products from each of the five reactions were combined into one tube, purified using StrataPrep PCR and eluted in 50 µl 1 mM Tris-HCl pH 8.6. The FEN-1 PCR product was analyzed on a gel and was determined to be approximately 1000 bp.

The PCR product comprising the fen-1 gene was cloned into the pCALnEK LIC vector (Stratagene) by creating ligation independent cloning termini (LIC), annealing the PCR product comprising the fen-1 gene to the pCALnEK LIC vector (Stratagene), and transforming cells with the annealing mixture according to the following method. Briefly, following PCR amplification, the PCR product is purified and treated with Pfu. DNA polymerase in the presence of dATP (according to the manual included with the Affinity® Protein Expression and Purification System, Stratagene, catalog #200326). In the absence of dTTP, dGTP and dCTP, the 3' to 5'-exonuclease activity of Pfu DNA polymerase removes at least 12 and 13 nucleotides at the respective 3' ends of the PCR product. This activity continues until the first adenine is encountered, producing a DNA fragment with 5'-extended single-stranded tails that are complementary to the single-stranded tails of the pCAL-n-EK vector.

Creating LIC Termini

LIC termini were created by preparing the following mixture:

45 µl purified PCR product (~0.5 µg/µl)
2.5 µl 10 mM dATP
5 µl 10× cPfu buffer
1 µl cPfu (2.5 u/µl)
0.5 µl H$_2$O cPfu and cPfu buffer can be obtained from Stratagene (cPfu, Stratagene Catalog #600153 and cPfu buffer, Stratagene Catalog #200532).

Samples were incubated at 72° C. for 20 minutes and products were cooled to room temperature. To each sample was added 40 ng prepared pCALnEK LIC vector (the prepared vector is available commercially from Stratagene in the Affinity, LIC Cloning and Protein Purification Kit (214405)). The vector and insert DNA are combined, allowed to anneal at room temperature and transformed into highly competent bacterial host cells (Wyborski et al., 1997, *Strategies*, 10:1).

Preparing Cells for Production of FEN

Two liters of LB-AMP was inoculated with 20 ml of an overnight culture of a FEN-1 clone (clone 3). Growth was allowed to proceed for approximately 11 hours at which point cells had reached an OD$_{600}$=0.974. Cells were induced overnight (about 12 hours) with 1 mM IPTG. Cells were collected by centrifugation and the resulting cell paste was stored at –20° C.

Purification of Tagged FEN-1,

Cells were resuspended in 20 ml of Calcium binding buffer

CaCl$_2$ Binding Buffer
50 mM Tris-HCl (pH 8.0)
150 mM NaCl
1.0 mM MgOAc
2 mM CaCl$_2$ The samples were sonicated with a Branson Sonicator using a microtip. The output setting was 5 and the duty cycle was 90%. Samples were sonicated three times and allowed to rest on ice during the intervals. The sonicate was centrifuged at 26,890×g. Cleared supernatants were mixed with 1 ml of washed (in CaCl$_2$ binding buffer) calmodulin agarose (CAM agarose) in a 50 ml conical tube and incubated on a slowly rotating wheel in a cold room (4° C.) for 5 hours. The CAM agarose was collected by light centrifugation (5000 rpm in a table top centrifuge).

Following removal of the supernatant, the CAM agarose was washed with 50 ml CaCl$_2$ binding buffer and transferred to a disposable drip column. The original container and pipet were rinsed thoroughly to remove residual agarose. The column was rinsed with approximately 200 ml of CaCl$_2$ binding buffer.

Elution was carried out with 10 ml of 50 mM NaCl elution buffer (50 mM NaCl, 50 mM Tris-HCl pH 8.0, 2 mM EGTA). 0.5 ml fractions were collected. A second elution step was carried out with 1M NaCl elution buffer wherein 0.5 ml fractions were collected.

Evaluation of Purified Tagged FEN-1

Figure 4:
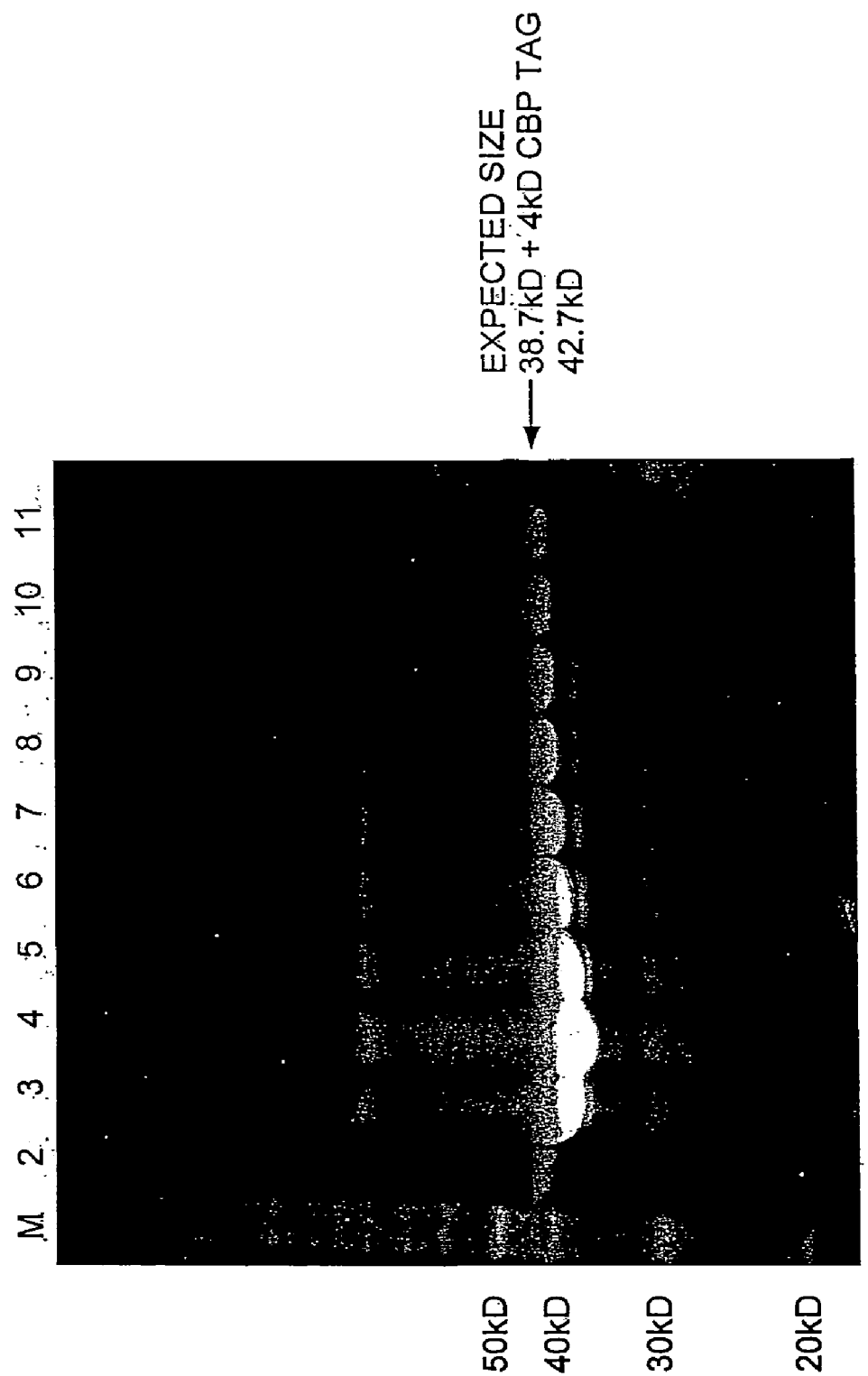
FIG. 4 is a Sypro Orange stained polyacrylamide gel demonstrating CBP-tagged Pfu FEN-1 protein.

Fractions containing CBP-tagged Pfu FEN-1 eluted in 1M NaCl were boiled in SDS and analyzed by SDS-PAGE on a 4-20% gel stained with Sypro Orange (FIG. 4).

The protein concentration of uncleaved FEN-1 was determined to be approximately 150 ng/microliter (below).

Enterokinase Protease (EK) Cleavage of the Purified FEN-1

Fractions 3-9 were dialyzed in 50 mM NaCl, 50 mM Tris-HCl pH 8.0 and 2 mM CaCl$_2$ overnight at 4° C.

An opaque, very fine precipitate appeared in the dialyzed FEN-1. When the sample was diluted ½0 the precipitate was removed. When the sample was diluted ⅓ insoluble material was still detectable. The ⅓ diluted material was heated at 37° C. for 2 minutes and mixed with Tween 20 to a final concentration of 0.1%. Upon the addition of the Tween 20, there was an almost immediate formation of "strings" and much coarser solids in the solution which could not be reversed even after the solution was adjusted to 1M NaCl.

EK cleavage was carried out using as a substrate the sample that was diluted ½0 as well as with a dilute sample prepared by rinsing the dialysis bag with 1× EK buffer.

EK cleavage was carried out by the addition of 1 µl EK (1 u/µl) overnight at room temperature (about 16 hours).

100 µl of STI agarose combined with 100 µl of CAM agarose were rinsed twice with 10 ml of 1×STI buffer (50 mM Tris-HCl pH 8.0, 200 mM NaCl, 2 mM CaCl$_2$, 0.1% Tween 20). NaCl was added to the two EK samples to bring the final concentration to 200 mM NaCl. The two samples were combined and added to the rinsed agarose. The samples were rotated slowly on a wheel at 4° C. for three hours and separated by light centrifugation in a table top centrifuge (as described). The supernatant was removed and the resin was rinsed twice with 500 µl 1× STI. The two rinses were combined and saved separately from the original supernatant. Samples were analyzed by SDS-PAGE on a 4-20% gel.

The concentration of digested product was approximately 23 ng/µl as determined by comparison to a Pfu standard at a concentration of approximately 50 ng/ml.

Example 3

FEN Nuclease Activity

The endonuclease activity of a FEN nuclease and the cleavage structure requirements of a FEN nuclease prepared as described in Example 2 can be determined according to the methods described either in the section entitled "FEN nucleaes" or below.

Briefly, three templates (FIG. 2) are used to evaluate the activity of a FEN nuclease according to the invention. Template 1 is a 5' $^{33}$P labeled oligonucleotide (Heltest4) with the following sequence:
5'                     AAAATAAATAAAAAAAAT<u>ACTGTTGGGAAGGGCGATCGGTGCG</u>3'.

The underlined section of Heltest4 represents the region complementary to M13mp18+. The cleavage product is an 18 nucleotide fragment with the sequence AAAATAAATAAAAAAAAT. Heltest4 binds to M13 to produce a complementary double stranded domain as well as a non-complementary 5' overhang. This duplex forms template 2 (FIG. 2). Template 3 (FIG. 2) has an additional primer (FENAS) bound to M13 which is directly adjacent to Heltest4. The sequence of FENAS is: 5' CCATTCGCCATTCAG-GCTGCGCA 3'. In the presence of template 3, a FEN nuclease binds the free 5' terminus of Heltest4, migrates to the junction and cleaves Heltest4 to produce an 18 nucleotide fragment. The resulting cleavage products are separated on a 6% acrylamide, 7M urea sequencing gel.

Templates are prepared as described below:

|  | Template 1 | Template 2 | Template 3 |
|---|---|---|---|
| Heltest4 | 14 µl | 14 µl | 14 µl |
| M13 | ** | 14 µl | 14 µl |
| FENAS | ** | ** | 14 µl |
| H$_2$O | 28 µl | 14 µl | ** |
| 10× Pfu Buff. | 4.6 µl | 4.6 µl | 4.6 µl |

Pfu buffer can be obtained from Stratagene (Catalog #200536).

The template mixture is heated at 95° C. for five minutes, cooled to room temperature for 45 minutes and stored at 4° C. overnight.

The enzyme samples are as follows:

| A. | H$_2$O (control) |
| B. | 2 µl undiluted uncleaved FEN-1 (~445 ng/µl) |
| C. | 2 µl ¹⁄₁₀ dilution of uncleaved FEN-1 (~44.5 ng/µl) |
| D. | 2 µl enterokinase protease (EK) cleaved PEN-1 (~23 ng/µl) |

The four reaction mixtures are mixed with the three templates as follows:

| 3 µl | template 1, template 2 or template 3 |
| 0.7 µl | 10× cloned Pfu buffer |
| 0.6 µl | 100 mM MgCl$_2$ |
| 2.00 µl | FEN-1 or H$_2$O |
| 0.7 µl | H$_2$O |
| 7.00 µl | total volume |

The reactions are allowed to proceed for 30 minutes at 50° C. and stopped by the addition of 2 µl formamide "Sequencing Stop" solution to each sample. Samples are heated at 95° C. for five minutes and loaded on a 6% acrylamide 7M urea Castway gel (Stratagene).

Alternatively, FEN nuclease activity can be analyzed in the following buffer wherein a one hour incubation time is utilized.

10× FEN Nuclease Buffer
500 mM Tris-HCl pH 8.0
100 mH MgCl$_2$
The reaction mixture is as follows:

| 3 µl | template 1, template 2 or template 3 |
| 0.7 µl | 10× FEN nuclease buffer |
| 2.00 µl | FEN-1 or H$_2$O (A-D, above) |
| 1.3 µl | H$_2$O |
| 7.00 µl | total volume |

Samples are incubated for one hour at 50° C. in the Robocyler 96 hot top thermal cycler. Following the addition of 2 µl of Sequencing Stop (95% formamide, 20 mM EDTA, 0.05% bromophenol blue, 0.05% xylene cyanol, available from Stratagene) dye solution, samples are heated at 99° C. for five minutes. Samples are loaded on an eleven inch long, hand-poured, 20% acrylamide/bis acrylamide, 7M urea gel. The gel is run at 20 watts until the bromophenol blue has migrated approximately ⅔ the total distance. The gel is removed from the glass plates and soaked for 10 minutes in fix solution (15% methanol, 5% acetic acid) and then for 10 minutes in water. The gel is placed on Whatmann 3 mm paper, covered with plastic wrap and dried for 2 hours in a heated vacuum gel dryer (~800 C). The gel is exposed overnight to X-ray film.

Figure 5:
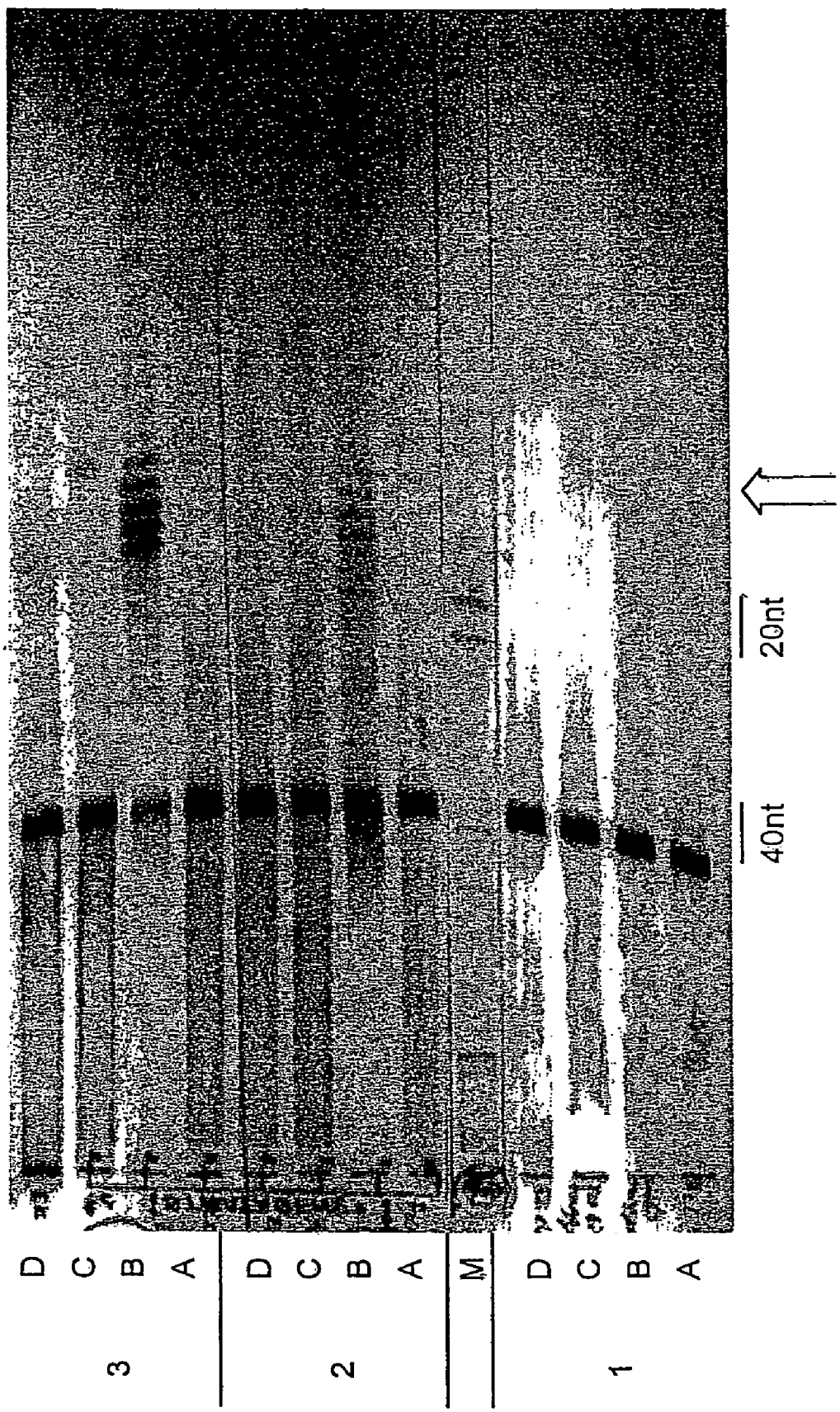
FIG. 5 is an autoradiograph of a FEN-1 nuclease assay.

An autoradiograph of a FEN-1 nuclease assay wherein templates 1, 2 and 3 (prepared as described above) are cleaved by the addition of:

| A. | H$_2$O |
| B. | 2 µl 1 of CBP-tagged Pfu FEN-1 |
| C. | 2 µl 1 of CBP-tagged Pfu FEN-1 diluted (1:10) |
| D. | 2 µl 1 of EK cleaved Pfu FEN-1 | is presented in FIG. 5.

The lanes are as follows. Lanes 1A, 1B, 1C and 1D represent template 1 cleaved with H$_2$O, undiluted CBP-tagged Pfu FEN-1, a 1:10 dilution of CBP-tagged Pfu FEN-1 and EK cleaved Pfu FEN-1, respectively. Lanes 2A, 2B, 2C and 2D represent template 2 cleaved with H$_2$O, undiluted CBP-tagged Pfu FEN-1, a 1:10 dilution of CBP-tagged Pfu FEN-1 and EK cleaved Pfu FEN-1, respectively. Lanes 3A, 3B, 3C and 3D represent template 3 cleaved with H$_2$O, undiluted CBP-tagged Pfu FEN-1, a 1:10 dilution of CBP-tagged Pfu FEN-1 and EK cleaved Pfu FEN-1, respectively.

Tagged Pfu FEN-1 contains the N-terminal CBP affinity purification tag. Any differences in activity between tagged and untagged versions of FEN-1 are due to differences in protein concentration (concentrations of enzyme samples are provided above) since the amounts of tagged versus untagged FEN-1 are not equivalent. Both tagged and untagged Pfu FEN-1 demonstrate cleavage activity.

FIG. 5 demonstrates the background level of cleavage in the absence of FEN-1 (lanes 1A, 2A and 3A). Further, this figure demonstrates that tagged Pfu FEN-1 cleaves more of template 2 as compared to template 1. In particular, the greatest amount of template 2 is cleaved in the presence of undiluted, tagged Pfu FEN-1 (lane 2B). Analysis of template 3 demonstrates that the greatest amount of template 3 is cleaved by undiluted, tagged Pfu FEN-1 and the least amount of template 3 is cleaved by diluted tagged FEN-1. Labeled probe migrates as a 40-43 nucleotide band. FEN-1 preferentially cleaves template 3 (which comprises an upstream primer) as compared to template 2. The cleavage product bands are the major bands migrating at 16-20 nucleotides. Heterogeneity in the labeled cleavage products is the result of heterogeneity in the labeled substrate, which was not gel-purified prior to use.

Example 4

PCR Amplification and Detection of β-Actin in the Presence of a FEN-1 Nuclease and a Taq Polymerase Deficient in 5' to 3' Exonuclease Activity A PCR assay is used to detect a target nucleic acid sequence. According to the method of this assay, a PCR reaction is carried out in the presence of a Taq polymerase deficient in 5' to 3' exonuclease activity (for example Yaq exo-), and a thermostable FEN-1 nuclease (e.g. Pfu FEN-1, prepared as described in Example 2). Detection of the release of fluorescently labeled fragments indicates the presence of the target nucleic acid sequence.

Duplicate PCR reactions containing 1× Sentinel Molecular beacon core buffer, 3.5 mM $MgCl_2$, 200 μM of each dNTP, a Taq polymerase deficient in 5' to 3' exonuclease activity (~1.45 U), Pfu FEN-1 (~23 ng), PE Biosystems β-Actin primers (300 nM each) (CATALOG #600500) and β-actin specific fluorogenic probe (200 nM; 5' FAM-3'TAMRA—PE Biosystems catalog #P/N 401846) were prepared. 10 ng of human genomic DNA (Promega) was used as the target nucleic acid sequence in each reaction. This reaction was performed in a 50 μl volume. Negative control reactions containing either Pfu FEN-1 alone, a Taq polymerase deficient in 5' to 3' exonuclease activity alone or reaction mixtures containing all components except a human genomic DNA template were prepared. Positive control reactions comprising 2.5 Units of Taq 2000 were also prepared. Reactions were assayed in a spectrofluorometric thermocycler (ABI 7700). Thermocycling parameters were 95° C. for 2 min and 40 cycles of 95° C. for 15 sec, 60° C. for 60 sec and 72° C. for 15 sec. Samples were interrogated during the annealing step.

Figure 6:
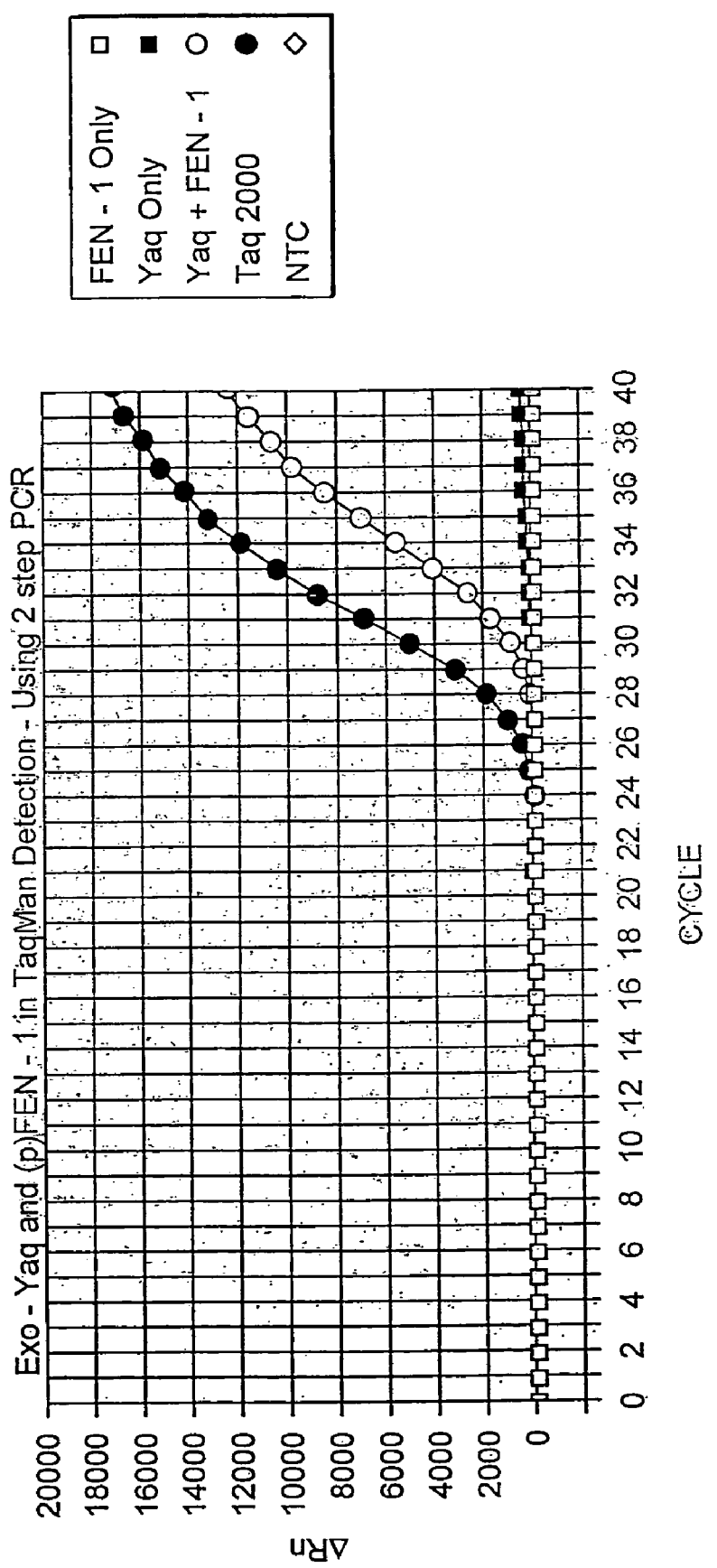
FIG. 6 is a graph representing detection of β-actin sequences in genomic DNA using fluorescently labeled β-actin probe in the presence of FEN-1 and a Taq polymerase deficient in 5' to 3' exonuclease activity.

As demonstrated in FIG. 6, no signal was generated in the presence of either Pfu FEN-1 alone or a Taq polymerase deficient in 5' to 3' exonuclease activity alone. In the presence of both a Taq polymerase deficient in 5' to 3' exonuclease activity and Pfu FEN-1 a signal was generated with a threshold cycle (Ct) of 26 and a final fluorescence intensity (FI) of 12,000 units. In the presence of Taq 2000 (a nucleic acid polymerase which has 5' to 3' exonuclease activity) (Taqman) a signal was generated with a Ct of 23 and a FI of 17,000 units.

These results demonstrate that β-actin DNA sequences can be detected by a PCR assay wherein a signal is generated in the presence of a Taq polymerase deficient in 5' to 3' exonuclease activity and a thermostable FEN-1 nuclease. Further, the 5' to 3' exonuclease activity that is absent in the Taq polymerase deficient in 5' to 3' exonuclease activity can be restored, in trans by the addition of Pfu FEN-1.

Example 5

PCR Amplification and Detection of β-Actin in the Presence of a FEN-1 Nuclease and a Pfu Polymerase Deficient in 5' to 3' Exonuclease Activity A PCR assay is used to detect a target nucleic acid sequence. According to the method of this assay, a PCR reaction is carried out in the presence of a Pfu polymerase (naturally lacking 5' to 3' exonuclease activity) or, in addition, Pfu polymerase deficient in 3' to 5' exonuclease activity as well (for example exo-Pfu), and a thermostable FEN-1 nuclease (Pfu FEN-1). Detection of the release of fluorescently labeled fragments indicates the presence of the target nucleic acid sequence.

Duplicate PCR reactions containing 1× Cloned Pfu buffer (available from Stratagene, Catalog #200532), 3.0 mM $MgCl_2$, 200 μM of each dNTP, 5 units of a Pfu polymerase deficient in 3' to 5' exonuclease activity, tagged or untagged Pfu FEN-1 (~23 ng), PEF (1 ng) (described in WO 98/42860), PE Biosystems β-Actin primers (300 nM each) (CATALOG #600500), and fluorogenic probe (200 nM; 5' FAM-3'TAMRA—PE Biosystems catalog #P/N 401846) were prepared. 10 ng of human genomic DNA (Promega) was used as the target nucleic acid sequence in each reaction. Reactions were performed in a 50 μl volume. Negative control reactions comprising a Pfu polymerase deficient in both 5' to 3' and 3' to 5' exonuclease activities alone or containing all of the components except the human genomic DNA template were also prepared. A reaction mixture containing 2.5 Units of Taq 2000 was prepared and used as a positive control. Reactions were analyzed in a spectrofluorometric thermocycler (ABI 7700). Thermocycling parameters where 95° C. for 2 min and 40 cycles of 95° C. for 15 sec, 60° C. for 60 sec and 72° C. for 15 sec.

Figure 7:
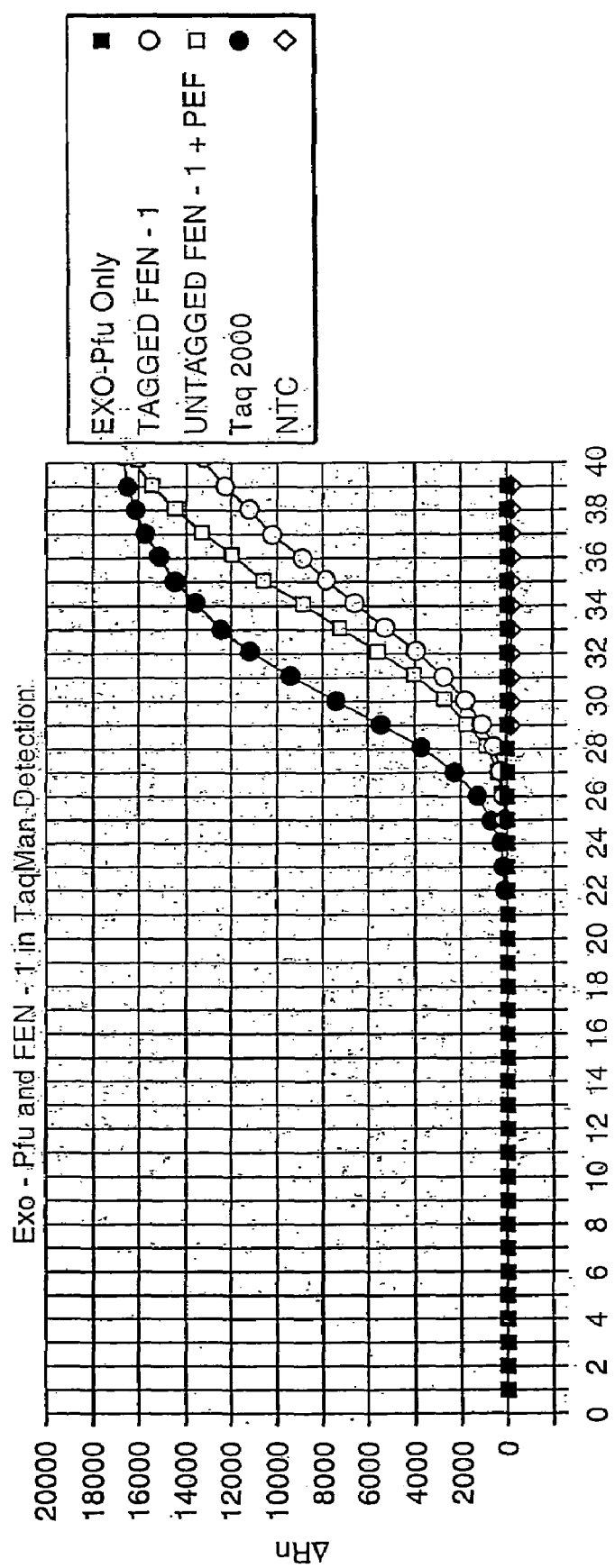
FIG. 7 is a graph representing detection of β-actin sequences in genomic DNA using fluorescently labeled β-actin probe in the presence of FEN-1 and a Pfu polymerase deficient in 3' to 5' exonuclease activity.

As demonstrated in FIG. 7, no signal was generated in the presence of a Pfu polymerase, naturally deficient in 5' to 3' exonuclease activity alone. In the presence of both a Pfu polymerase deficient in 5' to 3' exonuclease activity and tagged Pfu FEN-1 a signal was generated with a threshold cycle (Ct) of 23 and a final fluorescence intensity (FI) of 20,000 units. In the presence of a Pfu polymerase deficient in 5' to 3' exonuclease activity and untagged Pfu FEN-1 a signal was generated with a Ct of 21 and a final FI of 20,000 units. In the presence of Taq 2000, a signal was generated with a Ct of 21 and a FI of 19,000 units (TaqMan).

These results demonstrate that the presence of β-actin target can be detected by a PCR assay wherein a signal is generated in the presence of a Pfu polymerase deficient in 5' to 3' exonuclease activity and a thermostable FEN-1 nuclease. This signal is comparable to the signal generated in the presence of Taq 2000 in the absence of FEN-1. Further, the 5' to 3' exonuclease activity that is absent in a Pfu polymerase can be restored in trans by the addition of Pfu FEN-1.

Example 6

Figure 8A:
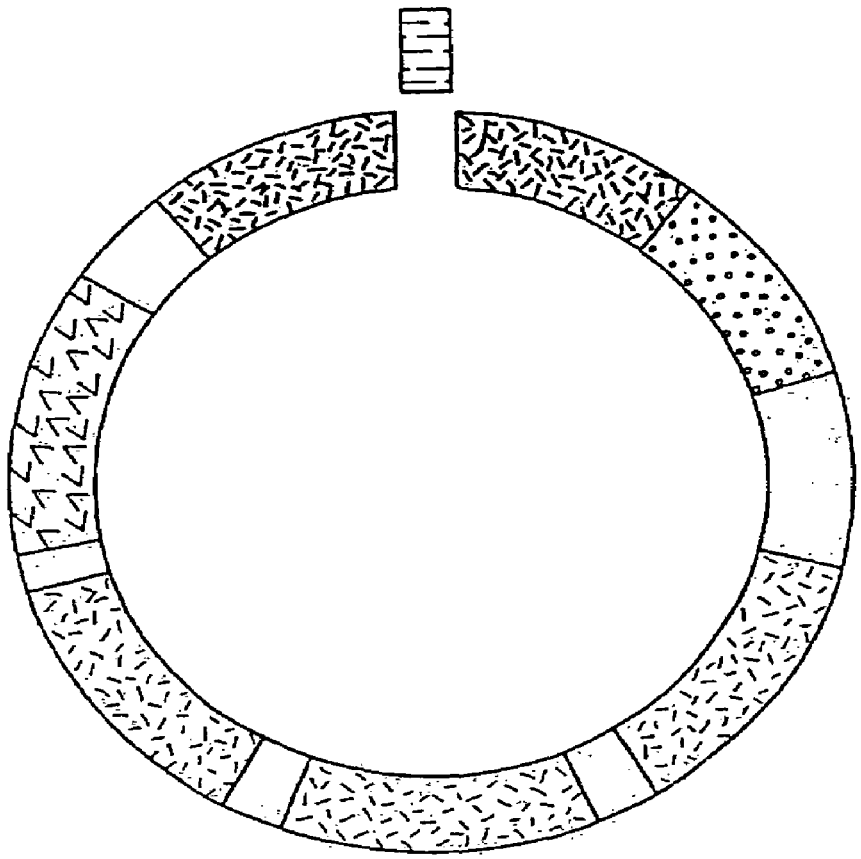
FIG. 8 is a representation of an open circle probe for rolling circle amplification.
Figure 8B:
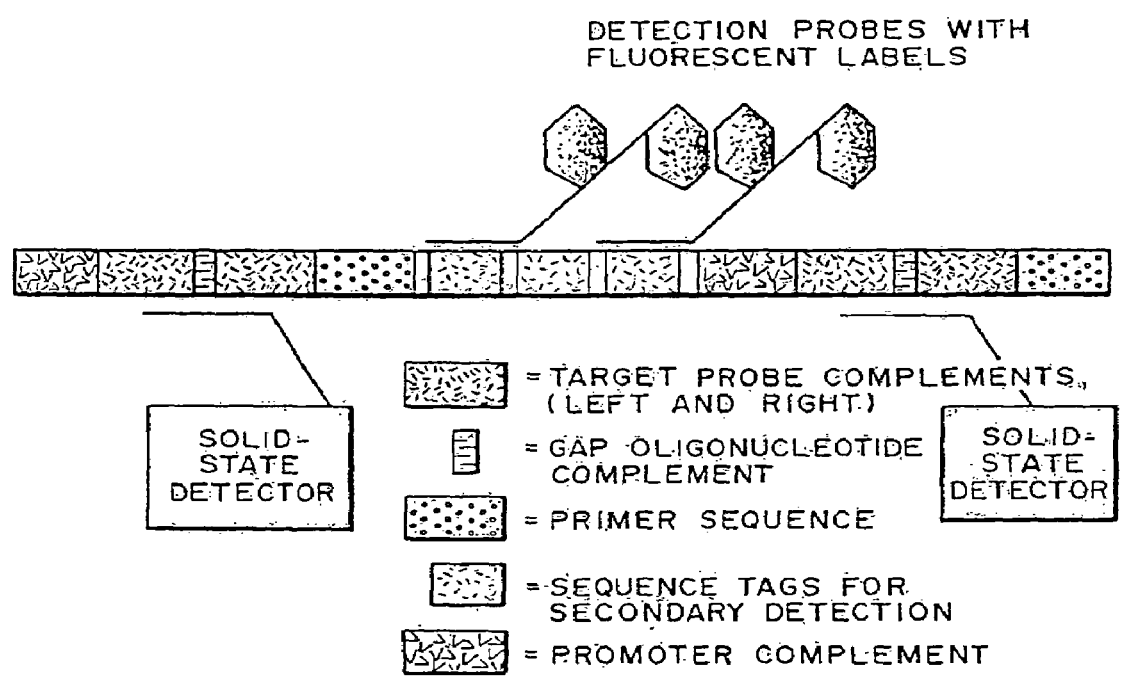
Figure 9A:
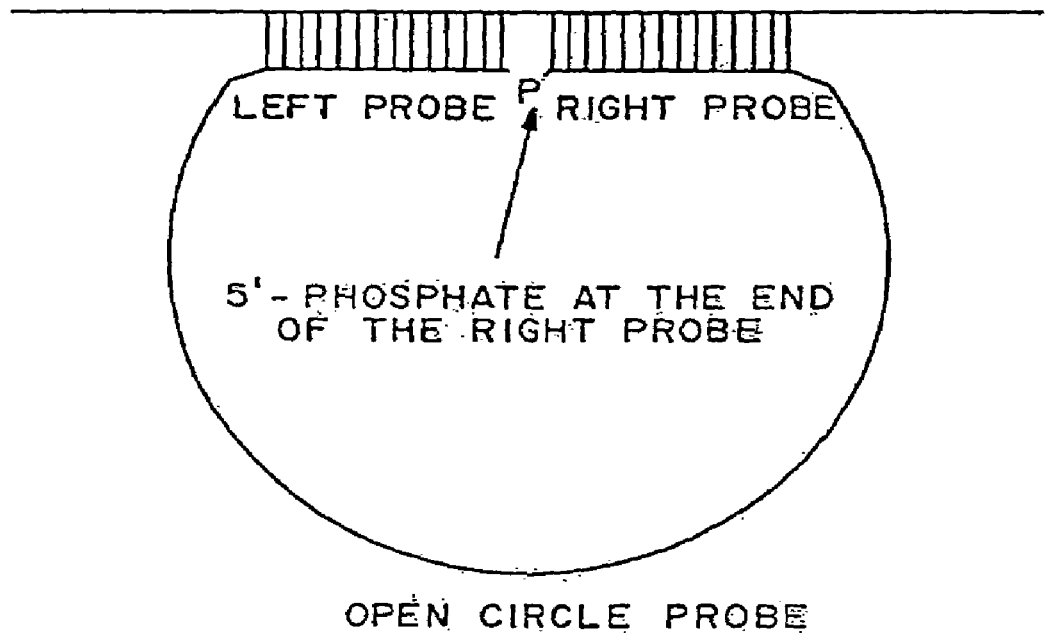
FIG. 9 is a representation of rolling circle amplification.
Figure 9A:
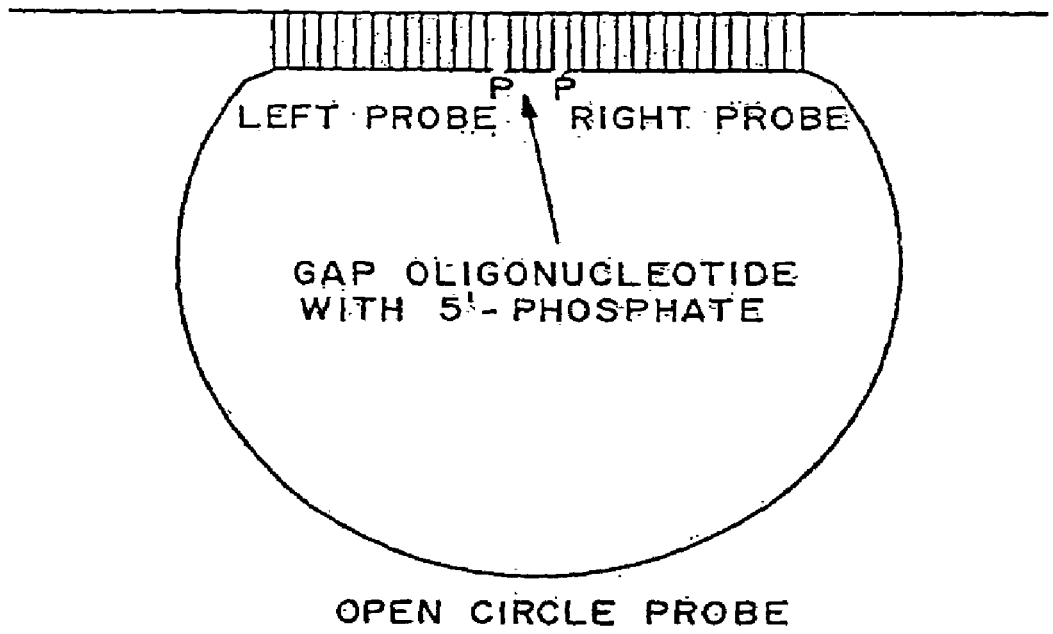
Figure 9B:
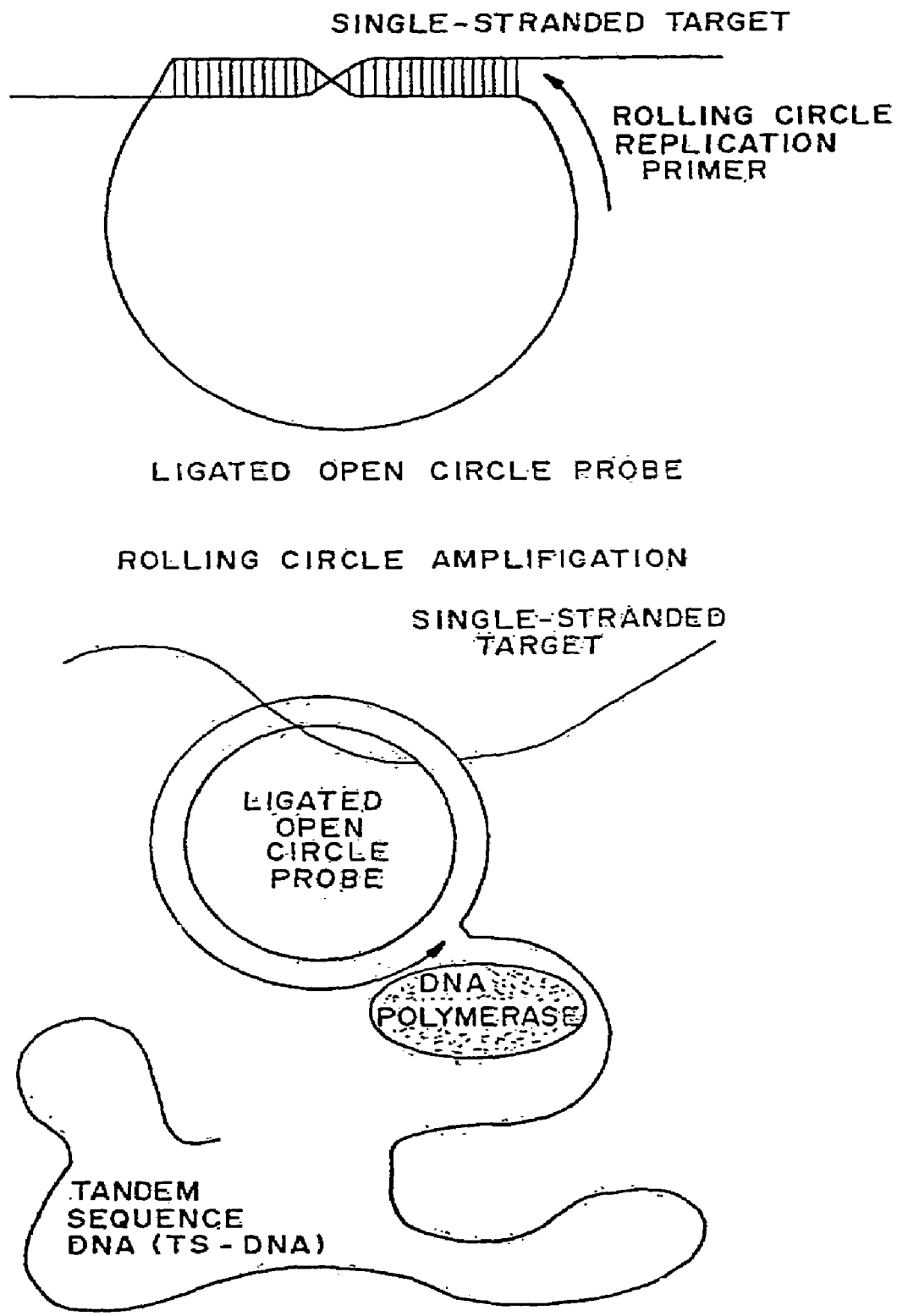

An assay according to the invention involving rolling circle amplification is performed using the human ornithine transcarbamylase gene as a target, which is detected in human DNA extracted from buffy coat by standard procedures. Target (400 ng) is heat-denatured for 4 minutes at 97° C., and incubated under ligation conditions in the presence of two 5'-phosphorylated oligonucleotides, an open circle probe and one gap oligonucleotide. The open circle probe has the sequence: gaggagaataaaagtttctca taagactcgtcatgtctcagcagct-tctaacggtcactaatacgactcactataggttctgcctctgggaacac, the gap nucleotide for the wild-type sequence is: tagtgatc. FIGS. 8 and 9 depict rolling circle probes and rolling circle amplification. The reaction buffer (40 ul) contains 5 units/μl of T4 DNA ligase (New England Biolabs), 10 mM Tris-HCl, pH 7.5, 0.2 M NaCl, 10 mM $MgCl_2$, 4 mM ATP, 80 nM open circle probe and 100 nM gap oligonucleotide. After incubation for 25 minutes at 37° C., 25 ul are removed and added to 25 ul of a solution containing 50 mM Tris-HCl, pH 7.5, 10 mM $MgCl_2$, 1 mM DTT, 400 μM each of dTTP, dATP, dGTP, dCTP, 0.2 μM rolling circle replication primer: gctgagacat-gacgagtc, phi29 DNA polymerase (160 ng/50 ul). The sample is incubated for 30 minutes at 30° C.

RNA is produced from a T7 promoter present in the open circle probe, by the addition of a compensating buffer (a stock solution or concentrate) that is diluted to achieve the following concentration of reagents: 35 mM Tris-HCl, pH 8.2, 2 mM spermidine, 18 mm $MgCl_2$, 5 mM GMP, 1 mM of ATP, CTP, GTP, 333 uM UTP, 667 uM Biotin-16-UTP, 0.03% Tween 20, 2 units per ul of T7 RNA polymerase. RNA production is performed as described in U.S. Pat. No. 5,858,033. The incubation is allowed to proceed for 90 minutes at 37° C.

Five µl of each sample (the actual test sample, a (−) ligase control sample, a (−) phi29 DNA polymerase control and a (−)T7 RNA polymerase control) in duplicate are removed for detection. The reverse transcription process includes the steps of A) ligating the open circle, B) synthesizing rolling circle single stranded DNA, C) making RNA (from a T7 promoter present in the open circle probe), D) reverse transcribing the RNA to make cDNA, and E) performing PCR amplification of the cDNA using primers and probes for generation of an detection of FEN cleavage structures, according to the invention. For reverse transcription, the reagents and protocols supplied with the Stratagene Sentinel Single-Tube RT-PCR Core Reagent Kit (Cat#600505) are used, except for the substitution of equal amounts of Yaq DNA polymerase for the Taq 2000 DNA polymerase which is recommended by the manufacturer. Each reaction contains 1× Sentinel molecular beacon RT-PCR core buffer, 3.5 mM $MgCl_2$, 200 µM of each dNTP, 5 units, exo-Pfu, 23 ng Pfu FEN-1, 1 ng PEF, 500 nM each of the upstream primer: aagtttctcataagactcgtcat, the reverse primer: aggcagaacctatagtgagtcgt, and the fluorogenic probe (for example FAM-DABCYL): agcttctaacggtcactaatacg. The reactions are subjected to incubation for 30 minutes at 45° C., 3 minutes at 95° C., followed by one cycle in a thermal cycler: 2 minutes at 95° C., 1 minute at 50° C., 1 minute at 72° C. The fluorescence in then determined in a fluorescence plate reader, such as Stratagene's FluorTracker or PE Biosystems' 7700 Sequence Detection System in Plate-Read Mode.

A crosscheck for the efficiency of detection is possible because of the incorporation of Biotin-16-UTP in the rolling circle amplification RNA product. An aliquot of the reactions is captured on glass slides (or alternatively in microwell plates) using an immobilized capture probe. Detection of the captured RNA amplicon is described in detail in U.S. Pat. No. 5,854,033, hereby incorporated by reference.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A kit for generating a signal indicative of the presence of a target nucleic acid sequence in a sample, comprising a thermostable Fen nuclease consisting of a 5' to 3' exonuclease and/or endonuclease activity, a nucleic acid polymerase that substantially lacks 5' to 3' exonuclease activity, a nucleic acid primer, and a labeled nucleic acid complementary to said target nucleic acid sequence.

2. The kit of claim 1, comprising one or more dNTPs.

3. The kit of claim 1 or 2, wherein said nucleic acid polymerase has less than 10% of the exonuclease activity of a wild type polymerase.

4. The kit of claim 3, wherein said nucleic acid polymerase has less than 5% of the exonuclease activity of a wild type polymerase.

5. The kit of claim 4, wherein said nucleic acid polymerase has less than 1% of the exonuclease activity of a wild type polymerase.

6. The kit of claim 1 or 2, wherein said nucleic acid polymerase is thermostable.

7. The kit of claim 6, wherein said Fen nuclease is selected from the group consisting of Fen nuclease enzyme of *Archaeglobus fulgidus, Methanococcus jannaschii, Pyrococcus furiosus*, and *Pyrococcus horikoshii*.

8. The kit of claim 6, wherein said nucleic acid polymerase is selected from the group consisting of Pfu, Pfu-exo, Taq, Taq-exo, Deep vent and Deep vent exo.

9. The kit of claim 1 or 2, wherein said labeled complementary nucleic acid comprises a label comprising a first member of a pair of interactive labels effectively positioned to quench the generation of a detectable signal, the first and second members of said pair being separable by a site susceptible to Fen nuclease cleavage, thereby allowing the nuclease activity of the Fen nuclease to separate the first interactive signal generating labeled moiety from the second interactive signal generating labeled moiety by cleaving at said site susceptible to Fen nuclease, thereby generating a signal.

10. The kit of claim 9, wherein said pair of interactive labels comprises a quencher moiety and a fluorescent moiety.

11. A composition comprising an isolated thermostable nucleic acid polymerase substantially lacking 5' to 3' exonuclease activity, a isolated thermostable Fen nuclease consisting of a 5' to 3' exonuclease and/or endonuclease activity, and a nucleic acid primer.

12. The composition of claim 11, comprising one or more dNTPs.

13. The composition of claim 11 or 12, wherein said Fen nuclease is selected from the group consisting of a Fen nuclease enzyme of *Archaeglobus fulgidus, Methanococcus jannaschii, Pyrococcus furiosus*, and *Pyrococcus horikoshii*.

14. The composition of claim 11 or 12, wherein said nucleic acid polymerase is selected from the group consisting of Pfu, Pfu-exo, Taq, Tag-exo, Deep vent and Deep vent exo.

15. The composition of claim 12, wherein said nucleic acid polymerase has less than 10% of the exonuclease activity of a wild type polymerase.

16. The composition of claim 15, wherein said nucleic acid polymerase has less than 5% of the exonuclease activity of a wild type polymerase.

17. The composition of claim 16, wherein said nucleic acid polymerase has less than 1% of the exonuclease activity of a wild type polymerase.

18. The composition of claim 12, further comprising a labeled nucleic acid complementary to a target nucleic acid sequence in a sample comprising a target nucleic acid.

19. The composition of claim 18, wherein said labeled complementary nucleic acid comprises a label comprising a first member of a pair of interactive labels effectively positioned to quench the generation of a detectable signal, the first and second members of said pair being separable by a site susceptible to Fen nuclease cleavage, thereby allowing the nuclease activity of the Fen nuclease to separate the first interactive signal generating labeled moiety from the second interactive signal generating labeled moiety by cleaving at said site susceptible to Fen nuclease, thereby generating a signal.

20. The composition of claim 19, wherein said pair of interactive labels comprises a quencher moiety and a fluorescent moiety, 21. The composition of claim 11, 12 or 18, further comprising said target nucleic acid.

22. The kit of claim 1, wherein said nucleic acid primer is between about 10 to 100 nucleotides in length.

23. The kit of claim 1, wherein said nucleic acid primer is between about 17-50 nucleotides in length.

24. The kit of claim 1, wherein said nucleic acid primer is between about 17-45 nucleotides in length.

25. The composition of claim 11, wherein said nucleic acid primer is between about 10 to 100 nucleotides in length.

26. The composition of claim 11, wherein said nucleic acid primer is between about 17-50 nucleotides in length.

27. The composition of claim 11, wherein said nucleic acid prime is between about 17-45 nucleotides in length.

28. The kit of claim 1, wherein said Fen nuclease is a Fen-1 nuclease.

29. The composition of claim 11, wherein said Fen nuclease is a Fen-1 nuclease.

30. The kit of claim 5, wherein said nucleic acid polymerase is thermostable.

31. The kit of claim 6, wherein said labeled complementary nucleic acid comprises a label comprising a first member of a pair of interactive labels effectively positioned to quench the generation of a detectable signal, the first and second members of said pair being separable by a site susceptible to Fen nuclease cleavage, thereby allowing the nuclease activity of the Fen nuclease to separate the first interactive signal generating labeled moiety from the second interactive signal generating labeled moiety by cleaving at said site susceptible to Fen nuclease, thereby generating a signal.

32. The kit of claim 30, wherein said labeled complementary nucleic acid comprises a label comprising a first member of a pair of interactive labels effectively positioned to quench the generation of a detectable signal, the first and second members of said pair being separable by a site susceptible to Fen nuclease cleavage, thereby allowing the nuclease activity of the Fen nuclease to separate the first interactive signal generating labeled moiety from the second interactive signal generating labeled moiety by cleaving at said site susceptible to Fen nuclease, thereby generating a signal.

* * * * *

SEQUENCE LISTING

```
<160> NUMBER OF SEQ ID NOS: 21

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaataaata aaaaaaatac tgttgggaag ggcgatcggt gcg                    43

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaataaata aaaaaaat                                                18

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccattcgcca ttcaggctgc gca                                          23
```

```
<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgatcgagca agcca                                                       15

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgagccgctc gctg                                                        14

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
accgcatcga atgcatgtct cgggtaaggc gtactcgacc                            40

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgattccgct ccagacttct cgggtgtact gagatcccct                            40

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaggcgtact cgacctgaaa                                                  20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
accatacgga tagggatct c                                                 21

<210> SEQ ID NO 10
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
gcaaagtatc atccctccag                                                     20

<210> SEQ ID NO 11
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cctctgcaga ctactattac ataatacgac tcactatagg gatctgcacg tattagccta         60
tagtgagtcg tattaatagg aaacaccaaa gatgatattt cgtcacagca agaattcagg        120

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cctctgcaga ctactattac                                                     20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cctgaattct tgctgtgacg                                                     20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
taggaaacac caaagatgat attt                                                24

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gacgacgaca agatgggtgt cccaattggt gagattatac caagaaaag                     49

<210> SEQ ID NO 16
<211> LENGTH: 56
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaacaagac ccgtttatct cttgaaccaa ctttcaaggg ttgattgttt tccact        56

<210> SEQ ID NO 17
<211> LENGTH: 95
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
gaggagaata aagtttctc ataagactcg tcatgtctca gcagcttcta acggtcacta    60
atacgactca ctataggttc tgcctctggg aacac                              95

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctgagacat gacgagtc                                                 18

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagtttctca taagactcgt cat                                           23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggcagaacc tatagtgagt cgt                                           23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
agcttctaac ggtcactaat acg                                           23
```